(12) United States Patent
Unverdorben et al.

(10) Patent No.: US 10,889,645 B2
(45) Date of Patent: *Jan. 12, 2021

(54) ENGINEERED T CELL RECEPTORS AND IMMUNE THERAPY USING THE SAME

(71) Applicant: Immatics Biotechnologies GmbH, Tuebingen (DE)

(72) Inventors: Felix Unverdorben, Stuttgart (DE); Sebastian Bunk, Tuebingen (DE); Martin Hofmann, Tuebingen (DE); Dominik Maurer, Moessingen (DE); Meike Hutt, Stuttgart (DE); Claudia Wagner, Tuebingen (DE); Leonie Alten, Tuebingen (DE)

(73) Assignee: IMMATICS BIOTECHNOLOGIES GMBH, Tuebingen (DE)

(*) Notice: Subject to any disclaimer, the term of this patent is extended or adjusted under 35 U.S.C. 154(b) by 0 days.

This patent is subject to a terminal disclaimer.

(21) Appl. No.: 16/736,337

(22) Filed: Jan. 7, 2020

(65) Prior Publication Data

US 2020/0207849 A1 Jul. 2, 2020

Related U.S. Application Data

(63) Continuation of application No. 16/180,980, filed on Nov. 5, 2018, now Pat. No. 10,618,956.

(60) Provisional application No. 62/582,202, filed on Nov. 6, 2017.

(30) Foreign Application Priority Data

Nov. 6, 2017 (DE) .................. 10 2017 125 888

(51) Int. Cl.
| C07K 14/725 | (2006.01) |
| C07K 16/28 | (2006.01) |
| C07K 16/18 | (2006.01) |
| C07K 14/78 | (2006.01) |
| A61P 35/00 | (2006.01) |
| C07K 14/775 | (2006.01) |
| C12N 5/0783 | (2010.01) |
| C12N 15/62 | (2006.01) |

(52) U.S. Cl.
CPC .............. *C07K 16/28* (2013.01); *A61P 35/00* (2018.01); *C07K 14/7051* (2013.01); *C07K 14/775* (2013.01); *C07K 14/78* (2013.01); *C07K 16/18* (2013.01); *C07K 16/2809* (2013.01); *C12N 5/0636* (2013.01); *C12N 15/62* (2013.01); *C07K 2317/31* (2013.01); *C07K 2317/55* (2013.01); *C07K 2317/622* (2013.01); *C07K 2317/73* (2013.01); *C07K 2317/92* (2013.01); *C07K 2319/03* (2013.01); *C07K 2319/33* (2013.01); *C12N 2510/00* (2013.01)

(58) Field of Classification Search
None
See application file for complete search history.

(56) References Cited

U.S. PATENT DOCUMENTS

| 5,545,806 | A | 8/1996 | Lonberg et al. |
| 9,101,585 | B2 | 8/2015 | Fritsche et al. |
| 9,717,774 | B2 | 8/2017 | Fritsche et al. |
| 9,895,415 | B2 | 2/2018 | Fritsche et al. |
| 9,993,523 | B2 | 6/2018 | Fritsche et al. |
| 10,064,913 | B2 | 9/2018 | Weinschenk et al. |
| 10,357,540 | B2 | 7/2019 | Fritsche et al. |
| 10,420,816 | B1 | 9/2019 | Fritsche et al. |
| 2002/0197266 | A1 | 12/2002 | Debinski |
| 2011/0229504 | A1 | 9/2011 | Fritsche et al. |
| 2013/0045191 | A1 | 2/2013 | Weinschenk et al. |
| 2015/0147347 | A1 | 5/2015 | Fritsche et al. |
| 2017/0204372 | A1 | 7/2017 | Mohler et al. |
| 2017/0304399 | A1 | 10/2017 | Fritsche et al. |
| 2017/0312336 | A1 | 11/2017 | Fritsche et al. |
| 2018/0000896 | A1 | 1/2018 | Fritsche et al. |
| 2018/0051080 | A1 | 2/2018 | Leonie et al. |
| 2018/0125929 | A1 | 5/2018 | Fritsche et al. |
| 2018/0319884 | A1 | 11/2018 | Leonie et al. |
| 2019/0290727 | A1 | 9/2019 | Fritsche et al. |

FOREIGN PATENT DOCUMENTS

| DE | 102016115246 B3 | 12/2017 |
| WO | 2011113819 A2 | 9/2011 |
| WO | 2016011210 A2 | 1/2016 |
| WO | 2016156202 A1 | 10/2016 |
| WO | 2018033291 A1 | 2/2018 |

OTHER PUBLICATIONS

International Search Report issued in counterpart application No. PCT/EP2018/080176, dated Jan. 17, 2019.
Hickman et al., "Antigen Selection for Enhanced Affinity T-Cell Receptor-Based Cancer Therapies" Journal of Biomolecular Screening. (2016) vol. 21(8) 769-785.
German Search Report of German Patent Application No. 102017125888.4 dated Oct. 12, 2018.

(Continued)

*Primary Examiner* — Zachary S Skelding
(74) *Attorney, Agent, or Firm* — McBee Moore & Vanik IP, LLC

(57) ABSTRACT

The present invention pertains to antigen recognizing constructs against COL6A3 antigens. The invention in particular provides novel engineered T cell receptor (TCR) based molecules which are selective and specific for the tumor expressing antigen COL6A3. The TCR of the invention, and COL6A3 antigen binding fragments derived therefrom, are of use for the diagnosis, treatment and prevention of COL6A3 expressing cancerous diseases. Further provided are nucleic acids encoding the antigen recognizing constructs of the invention, vectors comprising these nucleic acids, recombinant cells expressing the antigen recognizing constructs and pharmaceutical compositions comprising the compounds of the invention.

20 Claims, 35 Drawing Sheets
(7 of 35 Drawing Sheet(s) Filed in Color)
Specification includes a Sequence Listing.

(56) References Cited

OTHER PUBLICATIONS

Smith, M. J. et al., "Analysis of differential gene expression in colorectal cancer and stroma using fluorescence-activated cell sorting purification," British Journal of Cancer BJC, vol. 100, pp. 1452-1464, 2009.
Tilman, Gaëlle et al., "Human periostin gene expression in normal tissues, tumors and melanoma: evidences for periostin production by both stromal and melanoma cells," Molecular Cancer, vol. 6, pp. 1-13, 2007.
Qiao, Jie, et al., "Stroma derived COL6A3 is a potential prognosis marker of colorectal carcinoma revealed by quantitative proteomics," OncoTarget, vol. 6, pp. 29929-29946, 2015.
Köhler, G., et al., "Derivation of specific antibody-producing tissue culture and tumor lines by cell fusion," European Journal of Immunology, vol. 7, pp. 511-519, 1976.
Haskard, D.O., et al., "The Production of Human Monoclonal Autoantibodies from Patients with Rheumatoid Arthritis by the EBV-Hybridoma Technique," Journal of Immunological Methods, vol. 74, pp. 361-367, 1984.
Huse, William D., et al., "Generation of a Large Combinatorial Library of the Immunoglobulin Repertoire in Phage Lambda," Science, vol. 246, pp. 1275-1281, 1989.

Figure 4 cont.
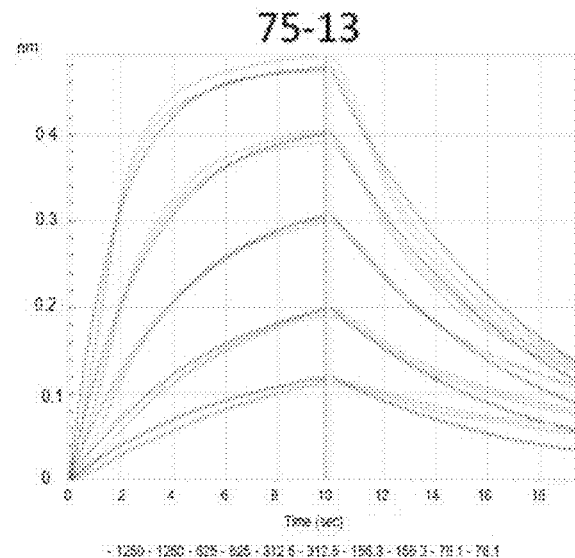
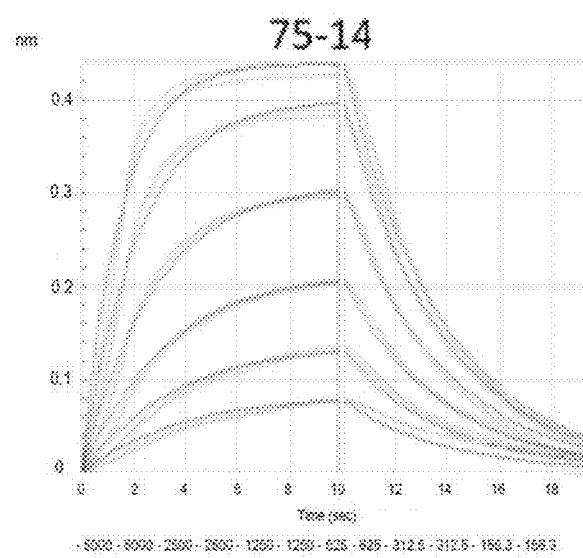
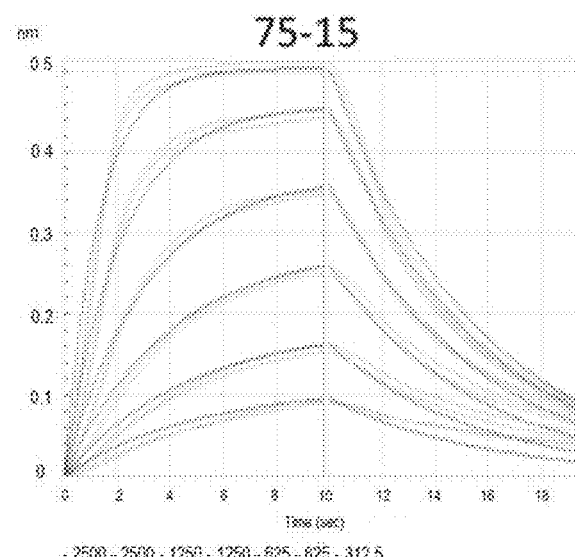
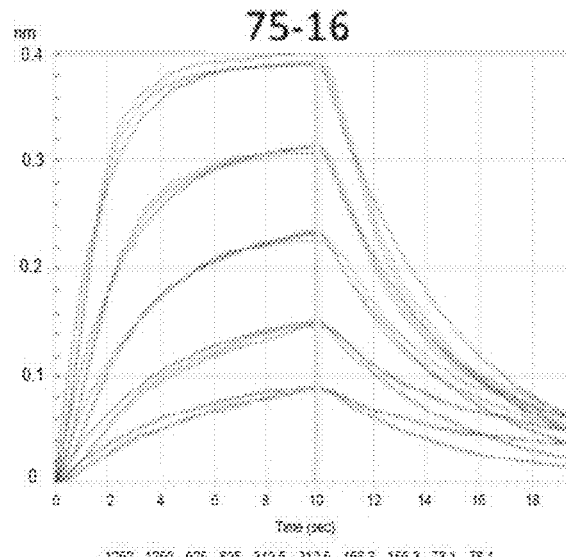

Figure 4 cont.
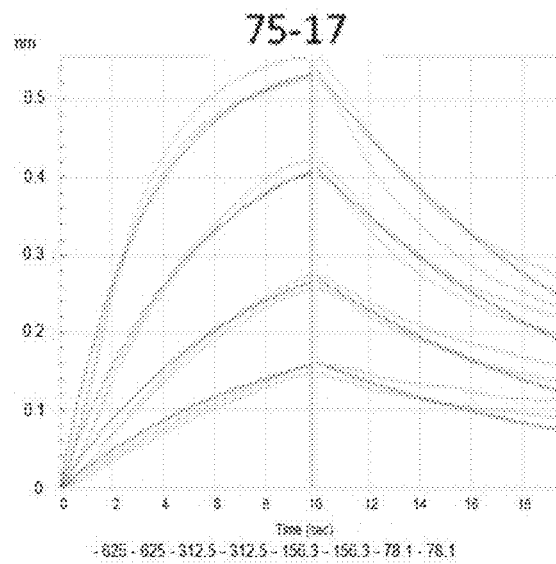
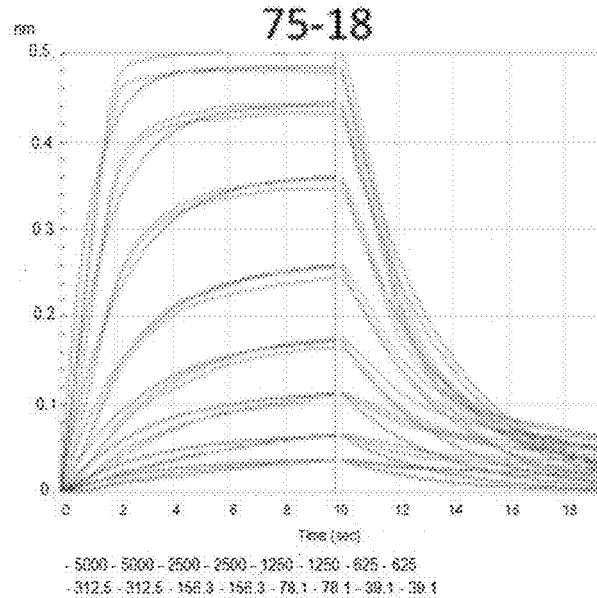
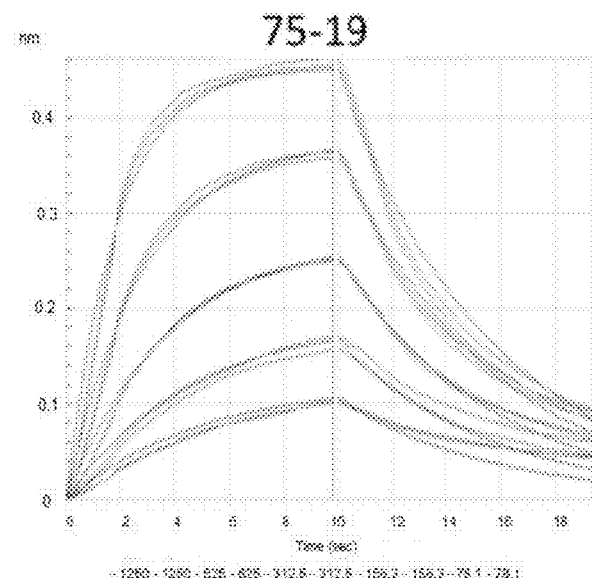
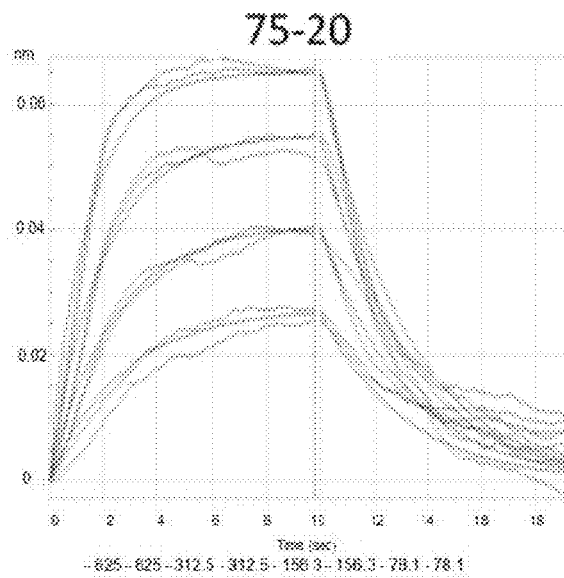

Figure 6 cont.
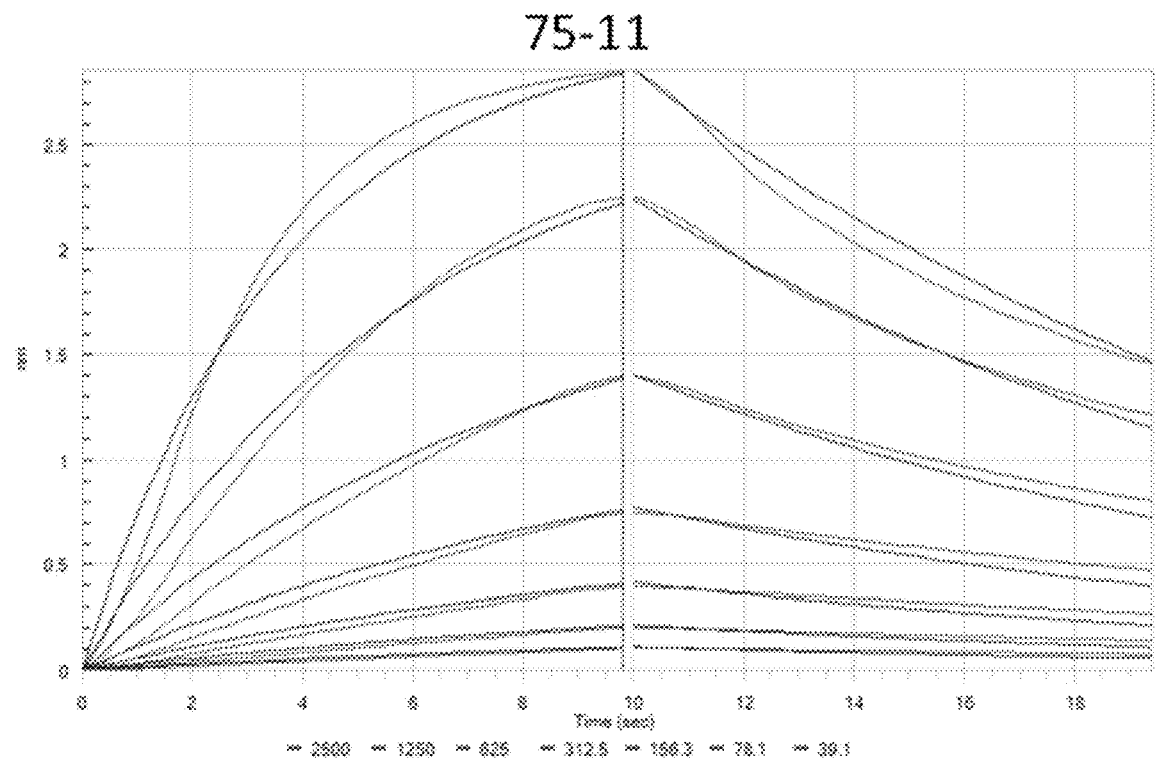
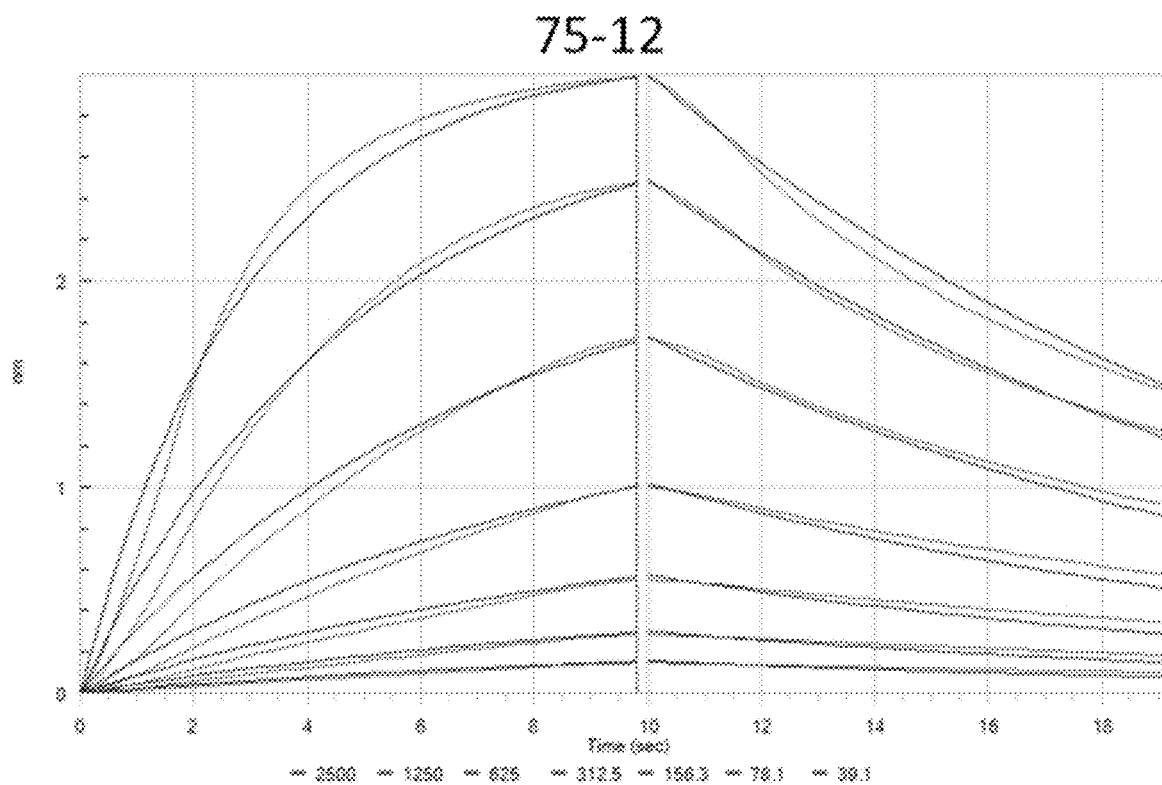

Figure 6 cont.
75-13
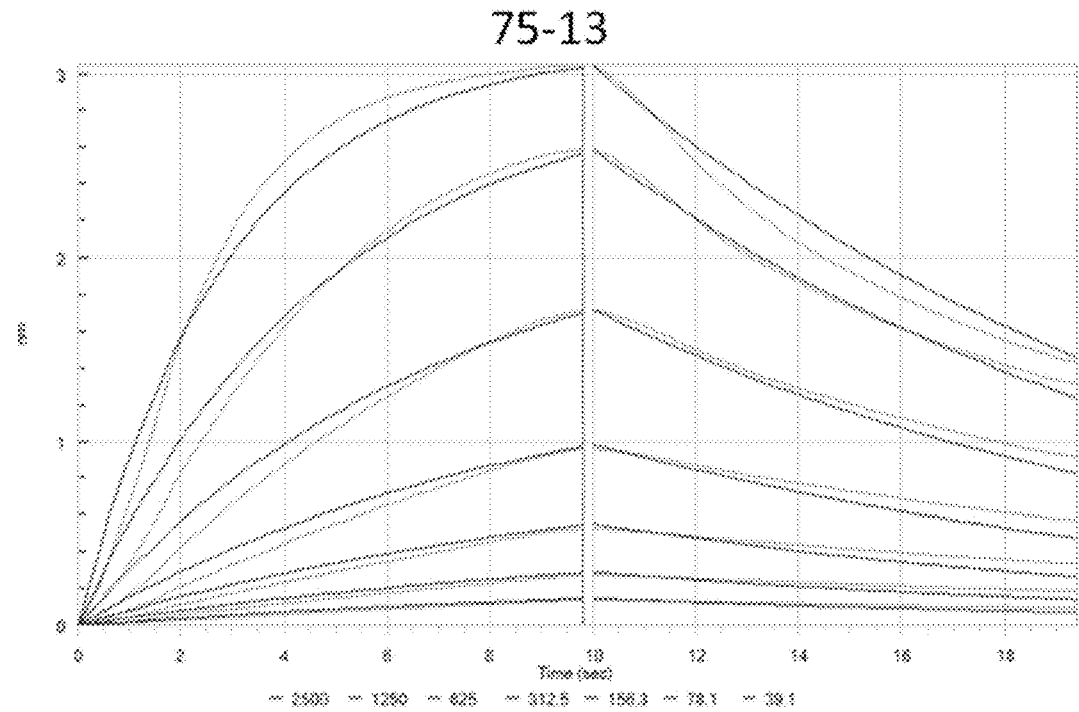
75-17
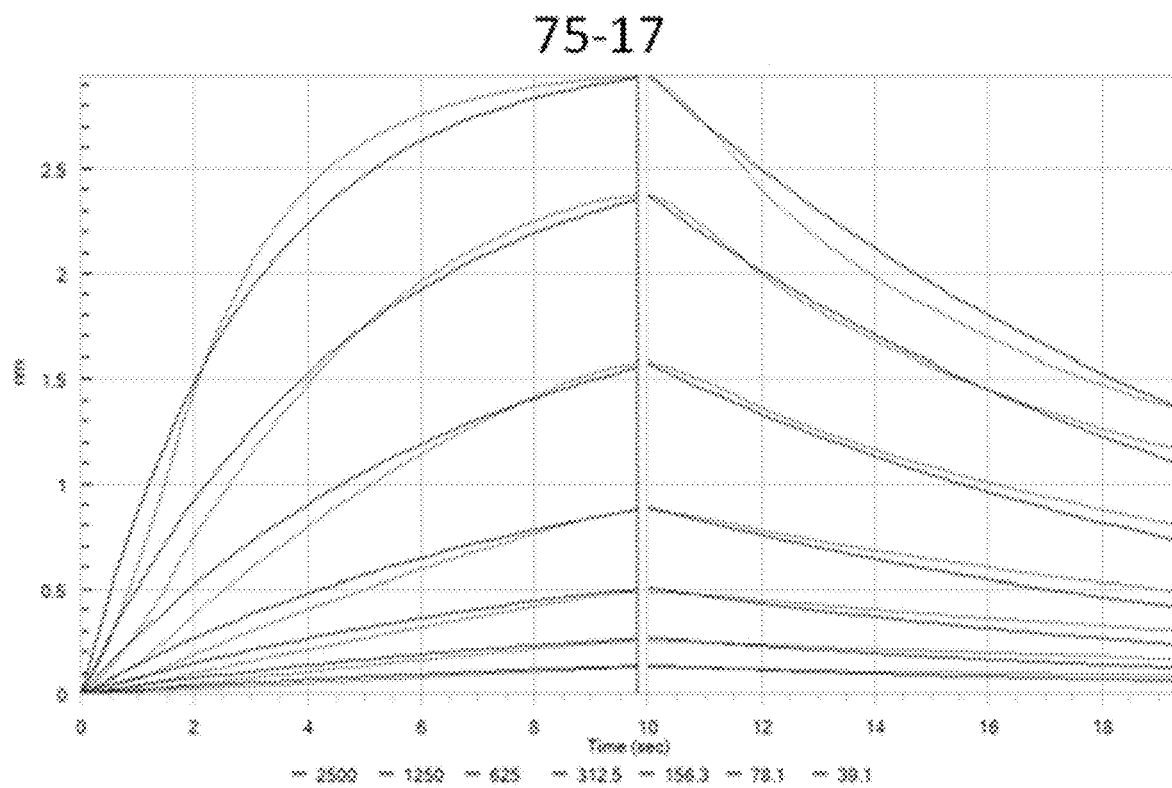

Figure 6 cont.
75-23
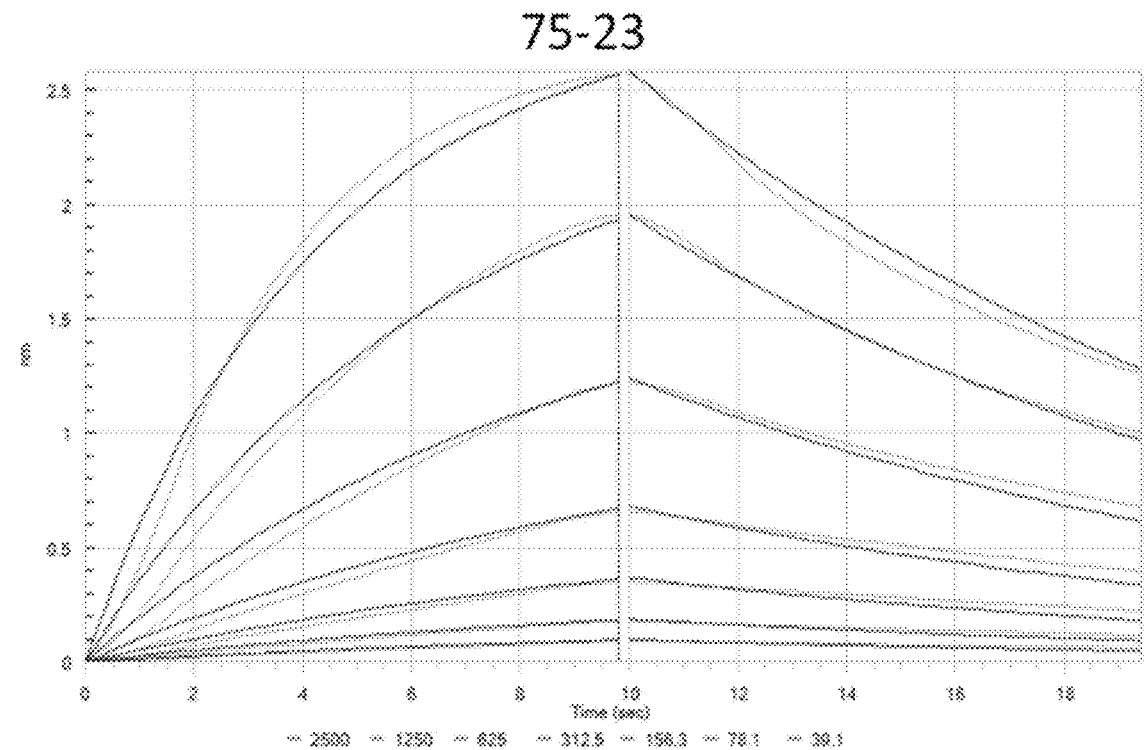
HLA-A*02/COL6A1-001
75-10
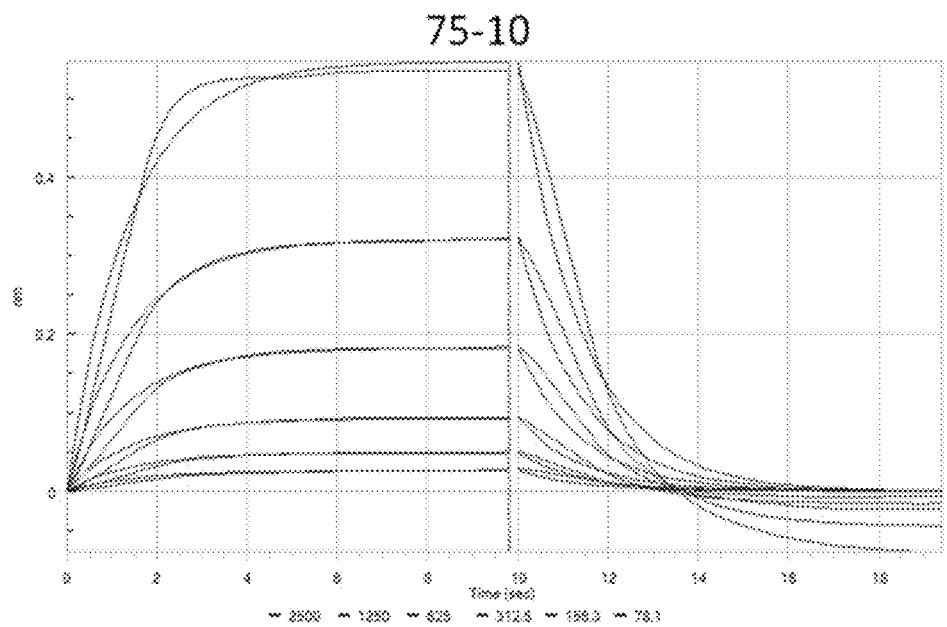

Figure 6 cont.
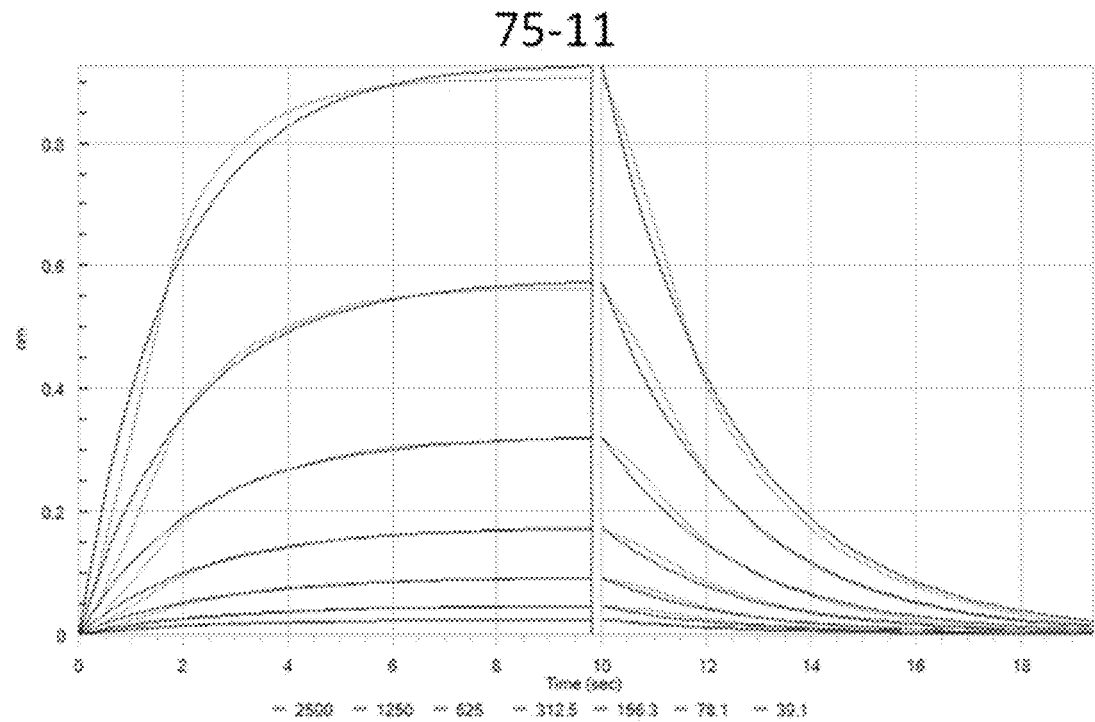
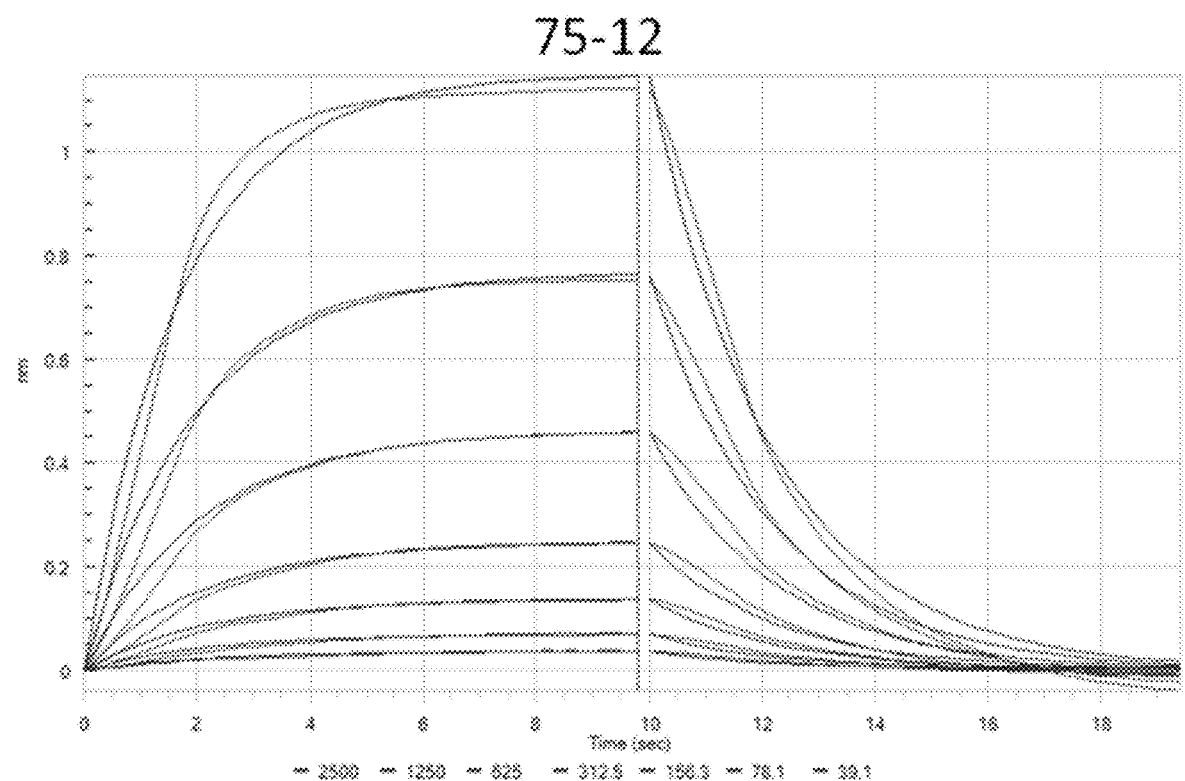

Figure 6 cont.
75-13
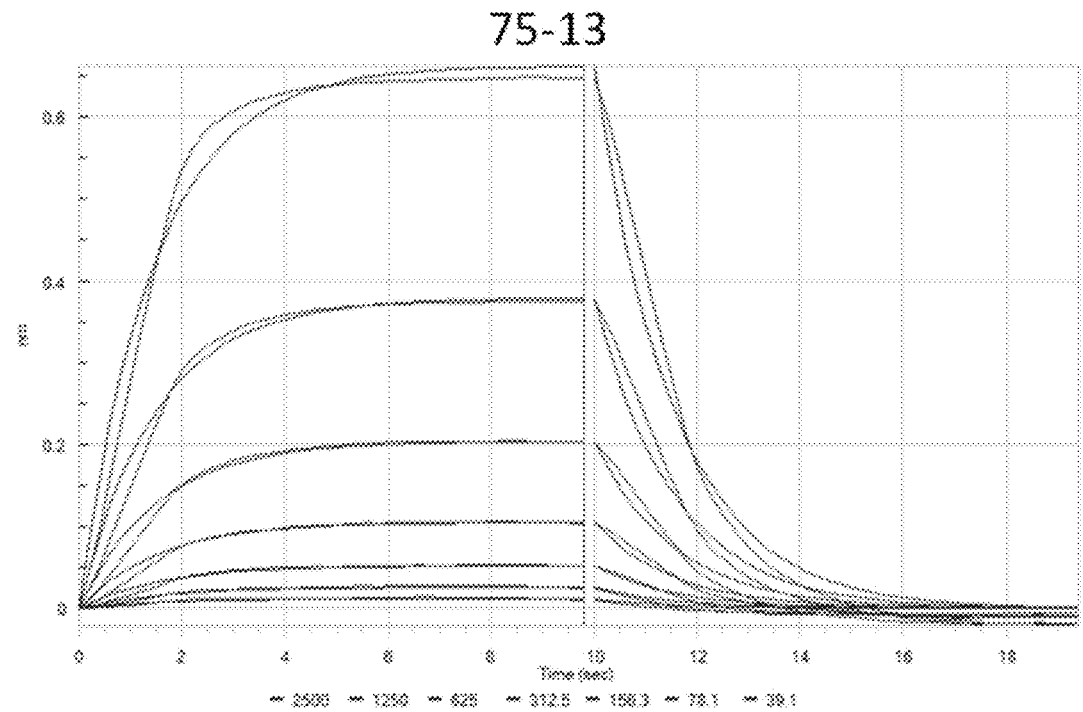
75-17
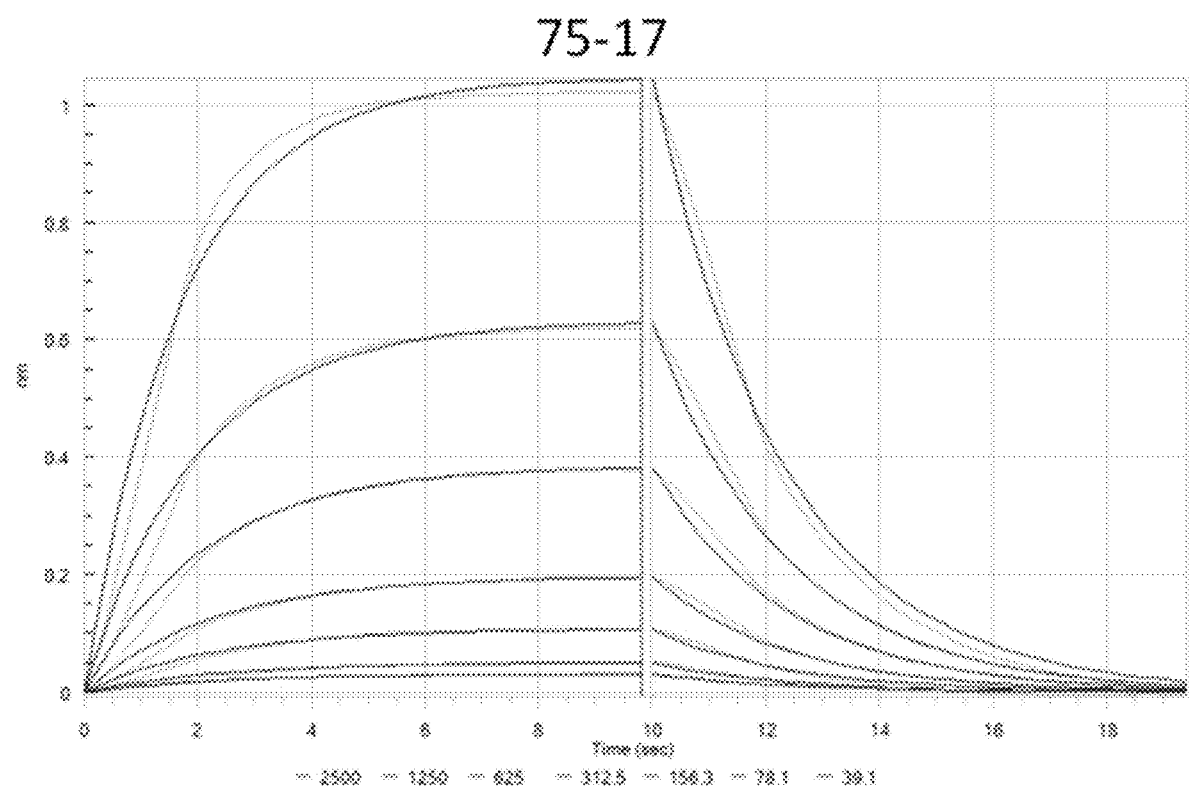

SEQUENCE LISTING

<160> NUMBER OF SEQ ID NOS: 66

<210> SEQ ID NO 1
<211> LENGTH: 9
<212> TYPE: PRT
<213> ORGANISM: Homo sapiens

<400> SEQUENCE: 1

Phe Leu Leu Asp Gly Ser Ala Asn Val
1               5

<210> SEQ ID NO 2
<211> LENGTH: 274
<212> TYPE: PRT
<213> ORGANISM: Homo sapiens

<400> SEQUENCE: 2

Met Lys Ser Leu Arg Val Leu Val Ile Leu Trp Leu Gln Leu Ser
1               5                   10                  15

Trp Val Trp Ser Gln Gln Lys Glu Val Glu Gln Asn Ser Gly Pro Leu
                20                  25                  30

Ser Val Pro Glu Gly Ala Ile Ala Ser Leu Asn Cys Thr Tyr Ser Asp
            35                  40                  45

Arg Gly Ser Gln Ser Phe Phe Trp Tyr Arg Gln Tyr Ser Gly Lys Ser
        50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Ala
            100                 105                 110

Tyr Ser Gly Ala Gly Ser Tyr Gln Leu Thr Phe Gly Lys Gly Thr Lys
        115                 120                 125

Leu Ser Val Ile Pro Asn Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser

<210> SEQ ID NO 3
<211> LENGTH: 21
<212> TYPE: PRT
<213> ORGANISM: Homo sapiens

-continued

```
<400> SEQUENCE: 3

Met Lys Ser Leu Arg Val Leu Leu Val Ile Leu Trp Leu Gln Leu Ser
1               5                   10                  15

Trp Val Trp Ser Gln
            20

<210> SEQ ID NO 4
<211> LENGTH: 112
<212> TYPE: PRT
<213> ORGANISM: Homo sapiens

<400> SEQUENCE: 4

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Phe Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Ala Tyr Ser Gly Ala Gly
                85                  90                  95

Ser Tyr Gln Leu Thr Phe Gly Lys Gly Thr Lys Leu Ser Val Ile Pro
            100                 105                 110

<210> SEQ ID NO 5
<211> LENGTH: 6
<212> TYPE: PRT
<213> ORGANISM: Homo sapiens

<400> SEQUENCE: 5

Asp Arg Gly Ser Gln Ser
1               5

<210> SEQ ID NO 6
<211> LENGTH: 5
<212> TYPE: PRT
<213> ORGANISM: Homo sapiens

<400> SEQUENCE: 6

Tyr Ser Asn Gly Asp
1               5

<210> SEQ ID NO 7
<211> LENGTH: 13
<212> TYPE: PRT
<213> ORGANISM: Homo sapiens

<400> SEQUENCE: 7

Cys Ala Ala Tyr Ser Gly Ala Gly Ser Tyr Gln Leu Thr
1               5                   10

<210> SEQ ID NO 8
<211> LENGTH: 141
<212> TYPE: PRT
<213> ORGANISM: Homo sapiens

<400> SEQUENCE: 8
```

-continued

```
Asn Ile Gln Asn Pro Asp Pro Ala Val Tyr Gln Leu Arg Asp Ser Lys
 1               5                  10                  15

Ser Ser Asp Lys Ser Val Cys Leu Phe Thr Asp Phe Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
 50                  55                  60

Trp Ser Asn Lys Ser Asp Phe Ala Cys Ala Asn Ala Phe Asn Asn Ser
 65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
130                 135                 140
```

<210> SEQ ID NO 9
<211> LENGTH: 4
<212> TYPE: PRT
<213> ORGANISM: Homo sapiens

<400> SEQUENCE: 9

```
Asn Ile Gln Asn
 1
```

<210> SEQ ID NO 10
<211> LENGTH: 308
<212> TYPE: PRT
<213> ORGANISM: Homo sapiens

<400> SEQUENCE: 10

```
Met Gly Phe Arg Leu Cys Cys Val Ala Phe Cys Leu Leu Gly Ala
 1               5                  10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
 50                  55                  60

Leu Ile Gln Tyr Tyr Asn Gly Glu Glu Arg Ala Lys Gly Asn Ile Leu
 65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Val Glu Ser Ser Tyr Gly Tyr Thr Phe Gly Ser Gly Thr Arg Leu
        115                 120                 125

Thr Val Val Glu Asp Leu Asn Lys Val Phe Pro Pro Glu Val Ala Val
130                 135                 140

Phe Glu Pro Ser Glu Ala Glu Ile Ser His Thr Gln Lys Ala Thr Leu
145                 150                 155                 160

Val Cys Leu Ala Thr Gly Phe Phe Pro Asp His Val Glu Leu Ser Trp
                165                 170                 175
```

```
Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Val Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Phe
305

<210> SEQ ID NO 11
<211> LENGTH: 19
<212> TYPE: PRT
<213> ORGANISM: Homo sapiens

<400> SEQUENCE: 11

Met Gly Phe Arg Leu Leu Cys Cys Val Ala Phe Cys Leu Leu Gly Ala
1               5                   10                  15

Gly Pro Val

<210> SEQ ID NO 12
<211> LENGTH: 112
<212> TYPE: PRT
<213> ORGANISM: Homo sapiens

<400> SEQUENCE: 12

Asp Ser Gly Val Thr Gln Thr Pro Lys His Leu Ile Thr Ala Thr Gly
1               5                   10                  15

Gln Arg Val Thr Leu Arg Cys Ser Pro Arg Ser Gly Asp Leu Ser Val
            20                  25                  30

Tyr Trp Tyr Gln Gln Ser Leu Asp Gln Gly Leu Gln Phe Leu Ile Gln
        35                  40                  45

Tyr Tyr Asn Gly Glu Glu Arg Ala Lys Gly Asn Ile Leu Glu Arg Phe
    50                  55                  60

Ser Ala Gln Gln Phe Pro Asp Leu His Ser Glu Leu Asn Leu Ser Ser
65                  70                  75                  80

Leu Glu Leu Gly Asp Ser Ala Leu Tyr Phe Cys Ala Ser Ser Val Glu
                85                  90                  95

Ser Ser Tyr Gly Tyr Thr Phe Gly Ser Gly Thr Arg Leu Thr Val Val
            100                 105                 110

<210> SEQ ID NO 13
<211> LENGTH: 6
<212> TYPE: PRT
<213> ORGANISM: Homo sapiens

<400> SEQUENCE: 13

Arg Ser Gly Asp Leu Ser
1               5
```

<210> SEQ ID NO 14
<211> LENGTH: 5
<212> TYPE: PRT
<213> ORGANISM: Homo sapiens

<400> SEQUENCE: 14

Tyr Asn Gly Glu Glu
1               5

<210> SEQ ID NO 15
<211> LENGTH: 12
<212> TYPE: PRT
<213> ORGANISM: Homo sapiens

<400> SEQUENCE: 15

Cys Ala Ser Ser Val Glu Ser Ser Tyr Gly Tyr Thr
1               5                   10

<210> SEQ ID NO 16
<211> LENGTH: 177
<212> TYPE: PRT
<213> ORGANISM: Homo sapiens

<400> SEQUENCE: 16

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
                20                  25                  30

Ala Thr Gly Phe Phe Pro Asp His Val Glu Leu Ser Trp Trp Val Asn
            35                  40                  45

Gly Lys Glu Val His Ser Gly Val Ser Thr Asp Pro Gln Pro Leu Lys
        50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Val Ser Tyr Gln Gln Gly Val Leu Ser
130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe

<210> SEQ ID NO 17
<211> LENGTH: 5
<212> TYPE: PRT
<213> ORGANISM: Homo sapiens

<400> SEQUENCE: 17

Glu Asp Leu Asn Lys
1               5

<210> SEQ ID NO 18

-continued

```
<211> LENGTH: 5
<212> TYPE: PRT
<213> ORGANISM: Homo sapiens

<400> SEQUENCE: 18

Glu Asp Leu Lys Asn
1               5

<210> SEQ ID NO 19
<211> LENGTH: 374
<212> TYPE: PRT
<213> ORGANISM: Homo sapiens

<400> SEQUENCE: 19

Met Gln Leu Leu Arg Cys Phe Ser Ile Phe Ser Val Ile Ala Ser Val
1               5                   10                  15

Leu Ala Gln Glu Leu Thr Thr Ile Cys Glu Gln Ile Pro Ser Pro Thr
            20                  25                  30

Leu Glu Ser Thr Pro Tyr Ser Leu Ser Thr Thr Thr Ile Leu Ala Asn
        35                  40                  45

Gly Lys Ala Met Gln Gly Val Phe Glu Tyr Tyr Lys Ser Val Thr Phe
    50                  55                  60

Val Ser Asn Cys Gly Ser His Pro Ser Thr Thr Ser Lys Gly Ser Pro
65                  70                  75                  80

Ile Asn Thr Gln Tyr Val Phe Gly Gly Gly Ser Asp Tyr Lys Asp
                85                  90                  95

Asp Asp Asp Lys Gly Gly Gly Ala Ser Gln Lys Glu Val Glu Gln Asn
            100                 105                 110

Ser Gly Pro Leu Ser Val Pro Glu Gly Ala Ile Ala Ser Leu Asn Cys
        115                 120                 125

Thr Tyr Ser Asp Arg Gly Ser Gln Ser Phe Phe Trp Tyr Arg Gln Tyr
    130                 135                 140

Ser Gly Lys Ser Pro Glu Leu Ile Met Ser Ile Tyr Ser Asn Gly Asp
145                 150                 155                 160

Lys Glu Asp Gly Arg Phe Thr Ala Gln Leu Asn Lys Ala Ser Gln Tyr
                165                 170                 175

Val Ser Leu Leu Ile Arg Asp Ser Gln Pro Ser Asp Ser Ala Thr Tyr
            180                 185                 190

Leu Cys Ala Ala Tyr Ser Gly Ala Gly Ser Tyr Gln Leu Thr Phe Gly
        195                 200                 205

Lys Gly Thr Lys Leu Ser Val Ile Pro Asn Ile Gln Asn Gly Gly Gly
    210                 215                 220

Gly Ser Gly Gly Gly Ser Gly Gly Gly Ser Gly Gly Gly Gly
225                 230                 235                 240

Ser Gly Val Thr Gln Thr Pro Lys His Leu Ile Thr Ala Thr Gly Gln
                245                 250                 255

Arg Val Thr Leu Arg Cys Ser Pro Arg Ser Gly Asp Leu Ser Val Tyr
            260                 265                 270

Trp Tyr Gln Gln Ser Leu Asp Gln Gly Leu Gln Phe Leu Ile Gln Tyr
        275                 280                 285

Tyr Asn Gly Glu Glu Arg Ala Lys Gly Asn Ile Leu Glu Arg Phe Ser
    290                 295                 300

Ala Gln Gln Phe Pro Asp Leu His Ser Glu Leu Asn Leu Ser Ser Leu
305                 310                 315                 320

Glu Leu Gly Asp Ser Ala Leu Tyr Phe Cys Ala Ser Ser Val Glu Ser
                325                 330                 335
```

```
Ser Tyr Gly Tyr Thr Phe Gly Ser Gly Thr Arg Leu Thr Val Val Glu
            340                 345                 350
Asp Leu Asn Lys Ala Ala Ala Gly Ser Gly Gly Glu Gln Lys Leu
            355                 360                 365
Ile Ser Glu Glu Asp Leu
    370
```

<210> SEQ ID NO 20
<211> LENGTH: 87
<212> TYPE: PRT
<213> ORGANISM: Homo sapiens

<400> SEQUENCE: 20

```
Met Gln Leu Leu Arg Cys Phe Ser Ile Phe Ser Val Ile Ala Ser Val
1               5                   10                  15
Leu Ala Gln Glu Leu Thr Thr Ile Cys Glu Gln Ile Pro Ser Pro Thr
            20                  25                  30
Leu Glu Ser Thr Pro Tyr Ser Leu Ser Thr Thr Thr Ile Leu Ala Asn
        35                  40                  45
Gly Lys Ala Met Gln Gly Val Phe Glu Tyr Tyr Lys Ser Val Thr Phe
    50                  55                  60
Val Ser Asn Cys Gly Ser His Pro Ser Thr Thr Ser Lys Gly Ser Pro
65                  70                  75                  80
Ile Asn Thr Gln Tyr Val Phe
                85
```

<210> SEQ ID NO 21
<211> LENGTH: 18
<212> TYPE: PRT
<213> ORGANISM: Homo sapiens

<400> SEQUENCE: 21

```
Gly Gly Gly Gly Ser Asp Tyr Lys Asp Asp Asp Lys Gly Gly Gly
1               5                   10                  15
Ala Ser
```

<210> SEQ ID NO 22
<211> LENGTH: 251
<212> TYPE: PRT
<213> ORGANISM: Homo sapiens

<400> SEQUENCE: 22

```
Gln Lys Glu Val Glu Gln Asn Ser Gly Pro Leu Ser Val Pro Glu Gly
1               5                   10                  15
Ala Ile Ala Ser Leu Asn Cys Thr Tyr Ser Asp Arg Gly Ser Gln Ser
            20                  25                  30
Phe Phe Trp Tyr Arg Gln Tyr Ser Gly Lys Ser Pro Glu Leu Ile Met
        35                  40                  45
Ser Ile Tyr Ser Asn Gly Asp Lys Glu Asp Gly Arg Phe Thr Ala Gln
    50                  55                  60
Leu Asn Lys Ala Ser Gln Tyr Val Ser Leu Leu Ile Arg Asp Ser Gln
65                  70                  75                  80
Pro Ser Asp Ser Ala Thr Tyr Leu Cys Ala Ala Tyr Ser Gly Ala Gly
                85                  90                  95
Ser Tyr Gln Leu Thr Phe Gly Lys Gly Thr Lys Leu Ser Val Ile Pro
            100                 105                 110
Asn Ile Gln Asn Gly Gly Gly Gly Ser Gly Gly Gly Ser Gly Gly
```

```
            115                 120                 125
Gly Gly Ser Gly Gly Gly Ser Gly Val Thr Gln Thr Pro Lys His
    130                 135                 140
Leu Ile Thr Ala Thr Gly Gln Arg Val Thr Leu Arg Cys Ser Pro Arg
145                 150                 155                 160
Ser Gly Asp Leu Ser Val Tyr Trp Tyr Gln Ser Leu Asp Gln Gly
                165                 170                 175
Leu Gln Phe Leu Ile Gln Tyr Tyr Asn Gly Glu Glu Arg Ala Lys Gly
            180                 185                 190
Asn Ile Leu Glu Arg Phe Ser Ala Gln Gln Phe Pro Asp Leu His Ser
        195                 200                 205
Glu Leu Asn Leu Ser Ser Leu Glu Leu Gly Asp Ser Ala Leu Tyr Phe
    210                 215                 220
Cys Ala Ser Ser Val Ser Ser Tyr Gly Tyr Thr Phe Gly Ser Gly
225                 230                 235                 240
Thr Arg Leu Thr Val Val Glu Asp Leu Asn Lys
                245                 250

<210> SEQ ID NO 23
<211> LENGTH: 18
<212> TYPE: PRT
<213> ORGANISM: Homo sapiens

<400> SEQUENCE: 23

Ala Ala Ala Gly Gly Ser Gly Gly Glu Gln Lys Leu Ile Ser Glu Glu
1               5                   10                  15

Asp Leu

<210> SEQ ID NO 24
<211> LENGTH: 251
<212> TYPE: PRT
<213> ORGANISM: Homo sapiens

<400> SEQUENCE: 24

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
                20                  25                  30

Phe Phe Trp Tyr Arg Gln Tyr Ser Gly Lys Ser Pro Glu Leu Ile Met
            35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Ala Tyr Ser Gly Ala Gly
                85                  90                  95

Ser Tyr Gln Leu Thr Phe Gly Lys Gly Thr Lys Leu Ser Val Ile Pro
            100                 105                 110

Asn Ile Gln Asn Gly Gly Gly Ser Gly Gly Gly Ser Gly Gly
        115                 120                 125

Gly Gly Ser Gly Gly Gly Ser Gly Val Thr Gln Thr Pro Lys His
    130                 135                 140

Leu Ile Thr Ala Thr Gly Gln Arg Val Thr Leu Arg Cys Ser Pro Arg
145                 150                 155                 160

Ser Gly Asp Leu Ser Val Tyr Trp Tyr Lys Gln Ser Leu Asp Gln Gly
                165                 170                 175
```

```
Leu Gln Phe Leu Ile Gln Tyr Tyr Asn Gly Glu Arg Ala Lys Gly
            180                 185                 190

Asn Ile Leu Glu Arg Phe Ser Ala Gln Gln Phe Pro Asp Leu His Ser
        195                 200                 205

Glu Leu Asn Leu Ser Ser Leu Glu Leu Gly Asp Ser Ala Leu Tyr Phe
    210                 215                 220

Cys Ala Ser Ser Val Glu Ser Ser Tyr Gly Tyr Thr Phe Gly Ser Gly
225                 230                 235                 240

Thr Arg Leu Thr Val Val Glu Asp Leu Asn Lys
            245                 250

<210> SEQ ID NO 25
<211> LENGTH: 251
<212> TYPE: PRT
<213> ORGANISM: Homo sapiens

<400> SEQUENCE: 25

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Ala Tyr Ser Gly Ala Gly
                85                  90                  95

Ser Tyr Gln Leu Thr Phe Gly Lys Gly Thr Lys Leu Ser Val Ile Pro
            100                 105                 110

Asn Ile Gln Asn Gly Gly Gly Gly Ser Gly Gly Gly Gly Ser Gly Gly
        115                 120                 125

Gly Gly Ser Gly Gly Gly Gly Ser Gly Val Thr Gln Thr Pro Lys His
130                 135                 140

Leu Ile Thr Ala Thr Gly Gln Arg Val Thr Leu Arg Cys Ser Pro Arg
145                 150                 155                 160

Ser Gly Asp Leu Ser Val Tyr Trp Tyr Gln Gln Ser Leu Asp Gln Gly
                165                 170                 175

Leu Gln Phe Leu Ile Gln Tyr Tyr Asn Gly Glu Arg Ala Lys Gly
            180                 185                 190

Asn Ile Ser Glu Arg Phe Ser Ala Gln Gln Phe Pro Asp Leu His Ser
        195                 200                 205

Glu Leu Asn Leu Ser Ser Leu Glu Leu Gly Asp Ser Ala Leu Tyr Phe
    210                 215                 220

Cys Ala Ser Ser Val Glu Ser Ser Tyr Gly Tyr Thr Phe Gly Ser Gly
225                 230                 235                 240

Thr Arg Leu Thr Val Val Glu Asp Leu Asn Lys
            245                 250

<210> SEQ ID NO 26
<211> LENGTH: 6
<212> TYPE: PRT
<213> ORGANISM: Homo sapiens

<400> SEQUENCE: 26
```

Asp Arg Arg Ser Gln Ser
1               5

<210> SEQ ID NO 27
<211> LENGTH: 247
<212> TYPE: PRT
<213> ORGANISM: Homo sapiens

<400> SEQUENCE: 27

Gln Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Arg Ser Gln Ser
            20                  25                  30

Phe Phe Trp Tyr Arg Gln Tyr Ser Gly Lys Ser Pro Glu Leu Ile Met
        35                  40                  45

Ser Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Ala Tyr Ser Gly Ala Gly
                85                  90                  95

Ser Tyr Gln Leu Thr Phe Gly Lys Gly Thr Lys Leu Ser Val Ile Pro
            100                 105                 110

Gly Gly Gly Gly Ser Gly Gly Gly Gly Ser Gly Gly Gly Gly Ser Gly
        115                 120                 125

Gly Gly Gly Ser Gly Gly Gly Ser Gly Val Thr Gln Thr Pro Lys
    130                 135                 140

His Leu Ile Thr Ala Thr Gly Gln Arg Val Thr Leu Arg Cys Ser Pro
145                 150                 155                 160

Arg Ser Gly Asp Leu Ser Val Tyr Trp Tyr Lys Gln Ser Leu Asp Gln
                165                 170                 175

Gly Leu Gln Phe Leu Ile Gln Tyr Tyr Asn Gly Glu Glu Arg Ala Lys
            180                 185                 190

Gly Asn Ile Ser Glu Arg Phe Ser Ala Gln Gln Phe Pro Asp Leu His
        195                 200                 205

Ser Glu Leu Asn Leu Ser Ser Leu Glu Leu Gly Asp Ser Ala Leu Tyr
    210                 215                 220

Phe Cys Ala Ser Ser Val Glu Ser Ser Tyr Gly Tyr Thr Phe Gly Ser
225                 230                 235                 240

Gly Thr Arg Leu Thr Val Val
                245

<210> SEQ ID NO 28
<211> LENGTH: 9
<212> TYPE: PRT
<213> ORGANISM: Homo sapiens

<400> SEQUENCE: 28

Ala Leu Leu Asp Gly Arg Val Gln Leu
1               5

<210> SEQ ID NO 29
<211> LENGTH: 9
<212> TYPE: PRT
<213> ORGANISM: Homo sapiens

<400> SEQUENCE: 29

Arg Leu Leu Asp Gly Ala Phe Lys Leu
1               5

<210> SEQ ID NO 30
<211> LENGTH: 9
<212> TYPE: PRT
<213> ORGANISM: Homo sapiens

<400> SEQUENCE: 30

Ile Leu Leu Asp Gly Ser Ala Ser Val
1               5

<210> SEQ ID NO 31
<211> LENGTH: 9
<212> TYPE: PRT
<213> ORGANISM: Homo sapiens

<400> SEQUENCE: 31

Phe Leu Leu Asp Gly Ser Glu Arg Leu
1               5

<210> SEQ ID NO 32
<211> LENGTH: 10
<212> TYPE: PRT
<213> ORGANISM: Homo sapiens

<400> SEQUENCE: 32

Phe Leu Phe Asp Gly Ser Ala Asn Leu Val
1               5                   10

<210> SEQ ID NO 33
<211> LENGTH: 9
<212> TYPE: PRT
<213> ORGANISM: Homo sapiens

<400> SEQUENCE: 33

Phe Leu Phe Asp Gly Ser Ala Asn Leu
1               5

<210> SEQ ID NO 34
<211> LENGTH: 9
<212> TYPE: PRT
<213> ORGANISM: Homo sapiens

<400> SEQUENCE: 34

Phe Leu Leu Asp Gly Ser Glu Gly Val
1               5

<210> SEQ ID NO 35
<211> LENGTH: 9
<212> TYPE: PRT
<213> ORGANISM: Homo sapiens

<400> SEQUENCE: 35

Phe Leu Leu Asp Gly Ser Asn Ser Val
1               5

<210> SEQ ID NO 36
<211> LENGTH: 9
<212> TYPE: PRT
<213> ORGANISM: Homo sapiens

<400> SEQUENCE: 36

Phe Leu Leu Asp Gly Ser Ser Arg Leu
1               5

```
<210> SEQ ID NO 37
<211> LENGTH: 6
<212> TYPE: PRT
<213> ORGANISM: Homo sapiens

<400> SEQUENCE: 37

Ala Arg Trp His Asn Asn
1               5

<210> SEQ ID NO 38
<211> LENGTH: 6
<212> TYPE: PRT
<213> ORGANISM: Homo sapiens

<400> SEQUENCE: 38

Ala Lys Asp His Leu Asn
1               5

<210> SEQ ID NO 39
<211> LENGTH: 6
<212> TYPE: PRT
<213> ORGANISM: Homo sapiens

<400> SEQUENCE: 39

Ala Arg Trp His Arg Asn
1               5

<210> SEQ ID NO 40
<211> LENGTH: 6
<212> TYPE: PRT
<213> ORGANISM: Homo sapiens

<400> SEQUENCE: 40

Ala Met Asp His Pro Tyr
1               5

<210> SEQ ID NO 41
<211> LENGTH: 6
<212> TYPE: PRT
<213> ORGANISM: Homo sapiens

<400> SEQUENCE: 41

Ala Thr Asp His Tyr Asn
1               5

<210> SEQ ID NO 42
<211> LENGTH: 6
<212> TYPE: PRT
<213> ORGANISM: Homo sapiens

<400> SEQUENCE: 42

Ala Arg Tyr His Thr Asn
1               5

<210> SEQ ID NO 43
<211> LENGTH: 6
<212> TYPE: PRT
<213> ORGANISM: Homo sapiens

<400> SEQUENCE: 43

Ala Pro Tyr His Leu Asn
1               5
```

```
<210> SEQ ID NO 44
<211> LENGTH: 6
<212> TYPE: PRT
<213> ORGANISM: Homo sapiens

<400> SEQUENCE: 44

Ala Lys Asp His Thr Asn
1               5

<210> SEQ ID NO 45
<211> LENGTH: 6
<212> TYPE: PRT
<213> ORGANISM: Homo sapiens

<400> SEQUENCE: 45

Ala Arg Tyr His Arg Asn
1               5

<210> SEQ ID NO 46
<211> LENGTH: 6
<212> TYPE: PRT
<213> ORGANISM: Homo sapiens

<400> SEQUENCE: 46

Ala Arg Trp His Ser Asn
1               5

<210> SEQ ID NO 47
<211> LENGTH: 6
<212> TYPE: PRT
<213> ORGANISM: Homo sapiens

<400> SEQUENCE: 47

Ala Thr Asp His Tyr Asn
1               5

<210> SEQ ID NO 48
<211> LENGTH: 6
<212> TYPE: PRT
<213> ORGANISM: Homo sapiens

<400> SEQUENCE: 48

Arg Trp Gly Asp Leu Asn
1               5

<210> SEQ ID NO 49
<211> LENGTH: 6
<212> TYPE: PRT
<213> ORGANISM: Homo sapiens

<400> SEQUENCE: 49

Ala Arg Asp His Leu Asn
1               5

<210> SEQ ID NO 50
<211> LENGTH: 514
<212> TYPE: PRT
<213> ORGANISM: Homo sapiens

<400> SEQUENCE: 50

Met Lys Trp Val Thr Phe Ile Ser Leu Leu Phe Leu Phe Ser Ser Ala
1               5                   10                  15

Tyr Glu Val Gln Leu Val Glu Ser Gly Gly Gly Leu Val Gln Pro Gly
            20                  25                  30
```

```
Gly Ser Leu Arg Leu Ser Cys Ala Ala Ser Gly Tyr Ser Phe Thr Gly
             35                  40                  45

Tyr Thr Met Asn Trp Val Arg Gln Ala Pro Gly Lys Gly Leu Glu Trp
 50                  55                  60

Val Ala Leu Ile Asn Pro Tyr Lys Gly Val Ser Thr Tyr Asn Gln Lys
 65                  70                  75                  80

Phe Lys Asp Arg Phe Thr Ile Ser Val Asp Lys Ser Lys Asn Thr Ala
                 85                  90                  95

Tyr Leu Gln Met Asn Ser Leu Arg Ala Glu Asp Thr Ala Val Tyr Tyr
                100                 105                 110

Cys Ala Arg Ser Gly Tyr Tyr Gly Asp Ser Asp Trp Tyr Phe Asp Val
            115                 120                 125

Trp Gly Gln Gly Thr Leu Val Thr Val Ser Ser Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
                180                 185                 190

Pro Ala Val Leu Gln Ser Ser Gly Leu Tyr Ser Leu Ser Ser Val Val
            195                 200                 205

Thr Val Pro Ser Ser Ser Leu Gly Thr Gln Thr Tyr Ile Cys Asn Val
210                 215                 220

Asn His Lys Pro Ser Asn Thr Lys Val Asp Lys Lys Val Glu Pro Lys
225                 230                 235                 240

Ser Cys Asp Lys Thr His Thr Ser Pro Pro Ser Pro Ala Pro Pro Val
                245                 250                 255

Ala Gly Gln Lys Glu Val Glu Gln Asn Ser Gly Pro Leu Ser Val Pro
                260                 265                 270

Glu Gly Ala Ile Ala Ser Leu Asn Cys Thr Tyr Ser Asp Arg Gly Ser
            275                 280                 285

Gln Ser Phe Phe Trp Tyr Arg Gln Tyr Ser Gly Lys Ser Pro Glu Leu
290                 295                 300

Ile Met Ser Ile Tyr Ser Asn Gly Asp Lys Glu Asp Gly Arg Phe Thr
305                 310                 315                 320

Ala Gln Leu Asn Lys Ala Ser Gln Tyr Val Ser Leu Leu Ile Arg Asp
                325                 330                 335

Ser Gln Pro Ser Asp Ser Ala Thr Tyr Leu Cys Ala Ala Tyr Ser Gly
                340                 345                 350

Ala Gly Ser Tyr Gln Leu Thr Phe Gly Lys Gly Thr Lys Leu Ser Val
            355                 360                 365

Ile Pro Asn Ile Gln Asn Gly Gly Gly Ser Gly Gly Gly Gly Ser
370                 375                 380

Gly Gly Gly Gly Ser Gly Gly Gly Ser Gly Gly Gly Gly Ser Gly
385                 390                 395                 400

Val Thr Gln Thr Pro Lys His Leu Ile Thr Ala Thr Gly Gln Arg Val
                405                 410                 415

Thr Leu Arg Cys Ser Pro Arg Ser Gly Asp Leu Ser Val Tyr Trp Tyr
            420                 425                 430

Lys Gln Ser Leu Asp Gln Gly Leu Gln Phe Leu Ile Gln Tyr Tyr Asn
435                 440                 445

Gly Glu Glu Arg Ala Lys Gly Asn Ile Ser Glu Arg Phe Ser Ala Gln
```

```
                450                 455                 460
Gln Phe Pro Asp Leu His Ser Glu Leu Asn Leu Ser Ser Leu Glu Leu
465                 470                 475                 480

Gly Asp Ser Ala Leu Tyr Phe Cys Ala Ser Val Glu Ser Ser Tyr
                485                 490                 495

Gly Tyr Thr Phe Gly Ser Gly Thr Arg Leu Thr Val Val Glu Asp Leu
                500                 505                 510

Lys Asn

<210> SEQ ID NO 51
<211> LENGTH: 258
<212> TYPE: PRT
<213> ORGANISM: Homo sapiens

<400> SEQUENCE: 51

Met Lys Trp Val Thr Phe Ile Ser Leu Leu Phe Leu Phe Ser Ser Ala
1               5                   10                  15

Tyr Glu Val Gln Leu Val Glu Ser Gly Gly Gly Leu Val Gln Pro Gly
                20                  25                  30

Gly Ser Leu Arg Leu Ser Cys Ala Ala Ser Gly Tyr Ser Phe Thr Gly
            35                  40                  45

Tyr Thr Met Asn Trp Val Arg Gln Ala Pro Gly Lys Gly Leu Glu Trp
        50                  55                  60

Val Ala Leu Ile Asn Pro Tyr Lys Gly Val Ser Thr Tyr Asn Gln Lys
65                  70                  75                  80

Phe Lys Asp Arg Phe Thr Ile Ser Val Asp Lys Ser Lys Asn Thr Ala
                85                  90                  95

Tyr Leu Gln Met Asn Ser Leu Arg Ala Glu Asp Thr Ala Val Tyr Tyr
                100                 105                 110

Cys Ala Arg Ser Gly Tyr Tyr Gly Asp Ser Asp Trp Tyr Phe Asp Val
            115                 120                 125

Trp Gly Gln Gly Thr Leu Val Thr Val Ser Ser Ala Ser Thr Lys Gly
        130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Ser Pro Pro Ser Pro Ala Pro Pro Val
                245                 250                 255

Ala Gly

<210> SEQ ID NO 52
<211> LENGTH: 232
<212> TYPE: PRT
<213> ORGANISM: Homo sapiens

<400> SEQUENCE: 52
```

```
Met Lys Trp Val Thr Phe Ile Ser Leu Leu Phe Leu Phe Ser Ser Ala
1               5                   10                  15

Tyr Ser Asp Ile Gln Met Thr Gln Ser Pro Ser Ser Leu Ser Ala Ser
            20                  25                  30

Val Gly Asp Arg Val Thr Ile Thr Cys Arg Ala Ser Gln Asp Ile Arg
        35                  40                  45

Asn Tyr Leu Asn Trp Tyr Gln Gln Lys Pro Gly Lys Ala Pro Lys Leu
50                  55                  60

Leu Ile Tyr Tyr Thr Ser Arg Leu Glu Ser Gly Val Pro Ser Arg Phe
65                  70                  75                  80

Ser Gly Ser Gly Ser Gly Thr Asp Tyr Thr Leu Thr Ile Ser Ser Leu
                85                  90                  95

Gln Pro Glu Asp Phe Ala Thr Tyr Tyr Cys Gln Gln Gly Asn Thr Leu
            100                 105                 110

Pro Trp Thr Phe Gly Gln Gly Thr Lys Val Glu Ile Lys Arg Thr Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230

<210> SEQ ID NO 53
<211> LENGTH: 274
<212> TYPE: PRT
<213> ORGANISM: Homo sapiens

<400> SEQUENCE: 53

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
        35                  40                  45

Ile Tyr Asn Leu Gln Trp Phe Arg Gln Asp Pro Gly Lys Gly Leu Thr
50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Arg
            100                 105                 110

Pro Thr Ser Gly Gly Ser Tyr Ile Pro Thr Phe Gly Arg Gly Thr Ser
        115                 120                 125

Leu Ile Val His Pro Tyr Ile Gln Asn Pro Asp Pro Ala Val Tyr Gln
    130                 135                 140
```

```
Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser
```

<210> SEQ ID NO 54
<211> LENGTH: 20
<212> TYPE: PRT
<213> ORGANISM: Homo sapiens

<400> SEQUENCE: 54

```
Met Glu Thr Leu Leu Gly Leu Leu Ile Leu Trp Leu Gln Leu Gln Trp
1               5                   10                  15

Val Ser Ser Lys
            20
```

<210> SEQ ID NO 55
<211> LENGTH: 113
<212> TYPE: PRT
<213> ORGANISM: Homo sapiens

<400> SEQUENCE: 55

```
Gln Glu Val Thr Gln Ile Pro Ala Ala Leu Ser Val Pro Glu Gly Glu
1               5                   10                  15

Asn Leu Val Leu Asn Cys Ser Phe Thr Asp Ser Ala Ile Tyr Asn Leu
            20                  25                  30

Gln Trp Phe Arg Gln Asp Pro Gly Lys Gly Leu Thr Ser Leu Leu Leu
        35                  40                  45

Ile Gln Ser Ser Gln Arg Glu Gln Thr Ser Gly Arg Leu Asn Ala Ser
    50                  55                  60

Leu Asp Lys Ser Ser Gly Arg Ser Thr Leu Tyr Ile Ala Ala Ser Gln
65                  70                  75                  80

Pro Gly Asp Ser Ala Thr Tyr Leu Cys Ala Val Arg Pro Thr Ser Gly
                85                  90                  95

Gly Ser Tyr Ile Pro Thr Phe Gly Arg Gly Thr Ser Leu Ile Val His
            100                 105                 110

Pro
```

<210> SEQ ID NO 56
<211> LENGTH: 141
<212> TYPE: PRT
<213> ORGANISM: Homo sapiens

<400> SEQUENCE: 56

```
Tyr Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140

<210> SEQ ID NO 57
<211> LENGTH: 311
<212> TYPE: PRT
<213> ORGANISM: Homo sapiens

<400> SEQUENCE: 57

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

Ser Tyr Val Gly Asn Thr Gly Glu Leu Phe Phe Gly Glu Gly Ser Arg
        115                 120                 125

Leu Thr Val Leu Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
```

```
                225                 230                 235                 240
Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
                260                 265                 270

Gly Val Leu Ser Ala Thr Ile Leu Tyr Glu Ile Leu Gly Lys Ala
                275                 280                 285

Thr Leu Tyr Ala Val Leu Val Ser Ala Leu Val Leu Met Ala Met Val
                290                 295                 300

Lys Arg Lys Asp Ser Arg Gly
305                 310

<210> SEQ ID NO 58
<211> LENGTH: 21
<212> TYPE: PRT
<213> ORGANISM: Homo sapiens

<400> SEQUENCE: 58

Met Ser Ile Gly Leu Leu Cys Cys Ala Ala Leu Ser Leu Leu Trp Ala
1                   5                  10                  15

Gly Pro Val Asn Ala
                20

<210> SEQ ID NO 59
<211> LENGTH: 111
<212> TYPE: PRT
<213> ORGANISM: Homo sapiens

<400> SEQUENCE: 59

Gly Val Thr Gln Thr Pro Lys Phe Gln Val Leu Lys Thr Gly Gln Ser
1                   5                  10                  15

Met Thr Leu Gln Cys Ala Gln Asp Met Asn His Glu Tyr Met Ser Trp
                20                  25                  30

Tyr Arg Gln Asp Pro Gly Met Gly Leu Arg Leu Ile His Tyr Ser Val
                35                  40                  45

Gly Ala Gly Ile Thr Asp Gln Gly Glu Val Pro Asn Gly Tyr Asn Val
                50                  55                  60

Ser Arg Ser Thr Thr Glu Asp Phe Pro Leu Arg Leu Leu Ser Ala Ala
65                  70                  75                  80

Pro Ser Gln Thr Ser Val Tyr Phe Cys Ala Ser Ser Tyr Val Gly Asn
                85                  90                  95

Thr Gly Glu Leu Phe Phe Gly Glu Gly Ser Arg Leu Thr Val Leu
                100                 105                 110

<210> SEQ ID NO 60
<211> LENGTH: 179
<212> TYPE: PRT
<213> ORGANISM: Homo sapiens

<400> SEQUENCE: 60

Glu Asp Leu Lys Asn Val Phe Pro Pro Glu Val Ala Val Phe Glu Pro
1                   5                  10                  15

Ser Glu Ala Glu Ile Ser His Thr Gln Lys Ala Thr Leu Val Cys Leu
                20                  25                  30

Ala Thr Gly Phe Tyr Pro Asp His Val Glu Leu Ser Trp Trp Val Asn
                35                  40                  45

Gly Lys Glu Val His Ser Gly Val Ser Thr Asp Pro Gln Pro Leu Lys
                50                  55                  60
```

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 61
<211> LENGTH: 9
<212> TYPE: PRT
<213> ORGANISM: Homo sapiens

<400> SEQUENCE: 61

Ser Leu Leu Met Trp Ile Thr Gln Val
1               5

<210> SEQ ID NO 62
<211> LENGTH: 308
<212> TYPE: PRT
<213> ORGANISM: Homo sapiens

<400> SEQUENCE: 62

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
                20                  25                  30

Ala Thr Gly Gln Arg Val Thr Leu Arg Cys Ser Pro Ala Met Asp His
            35                  40                  45

Pro Tyr Val Tyr Trp Tyr Gln Gln Ser Leu Asp Gln Gly Leu Gln Phe
        50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Val Glu Ser Ser Tyr Gly Tyr Thr Phe Gly Ser Gly Thr Arg Leu
        115                 120                 125

Thr Val Val Glu Asp Leu Asn Lys Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Phe Pro Asp His Val Glu Leu Ser Trp
                165                 170                 175

Trp Val Asn Gly Lys Glu Val His Ser Gly Val Ser Thr Asp Pro Gln
            180                 185                 190

```
Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Val Ser Tyr Gln Gln Gly
                260                 265                 270

Val Leu Ser Ala Thr Ile Leu Tyr Glu Ile Leu Leu Gly Lys Ala Thr
            275                 280                 285

Leu Tyr Ala Val Leu Val Ser Ala Leu Val Leu Met Ala Met Val Lys
        290                 295                 300

Arg Lys Asp Phe
305

<210> SEQ ID NO 63
<211> LENGTH: 274
<212> TYPE: PRT
<213> ORGANISM: Homo sapiens

<400> SEQUENCE: 63

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Arg Ser Gln Ser Phe Phe Trp Tyr Arg Gln Tyr Ser Gly Lys Ser
    50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Ala
            100                 105                 110

Tyr Ser Gly Ala Gly Ser Tyr Gln Leu Thr Phe Gly Lys Gly Thr Lys
        115                 120                 125

Leu Ser Val Ile Pro Asn Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255
```

Leu Leu Lys Val Ala Gly Phe Asn Leu Leu Met Thr Leu Arg Leu Trp
            260                 265                 270

Ser Ser

<210> SEQ ID NO 64
<211> LENGTH: 515
<212> TYPE: PRT
<213> ORGANISM: Homo sapiens

<400> SEQUENCE: 64

Met Lys Trp Val Thr Phe Ile Ser Leu Leu Phe Leu Phe Ser Ser Ala
1               5                   10                  15

Tyr Ser Glu Val Gln Leu Val Glu Ser Gly Gly Gly Leu Val Gln Pro
            20                  25                  30

Gly Gly Ser Leu Arg Leu Ser Cys Ala Ala Ser Gly Tyr Ser Phe Thr
        35                  40                  45

Gly Tyr Thr Met Asn Trp Val Arg Gln Ala Pro Gly Lys Gly Leu Glu
    50                  55                  60

Trp Val Ala Leu Ile Asn Pro Tyr Lys Gly Val Ser Thr Tyr Asn Gln
65                  70                  75                  80

Lys Phe Lys Asp Arg Phe Thr Ile Ser Val Asp Lys Ser Lys Asn Thr
                85                  90                  95

Ala Tyr Leu Gln Met Asn Ser Leu Arg Ala Glu Asp Thr Ala Val Tyr
            100                 105                 110

Tyr Cys Ala Arg Ser Gly Tyr Tyr Gly Asp Ser Asp Trp Tyr Phe Asp
        115                 120                 125

Val Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Ser Pro Pro Ser Pro Ala Pro Pro
                245                 250                 255

Val Ala Gly Gln Lys Glu Val Glu Gln Asn Ser Gly Pro Leu Ser Val
            260                 265                 270

Pro Glu Gly Ala Ile Ala Ser Leu Asn Cys Thr Tyr Ser Asp Arg Gly
        275                 280                 285

Ser Gln Ser Phe Phe Trp Tyr Arg Gln Tyr Ser Gly Lys Ser Pro Glu
    290                 295                 300

Leu Ile Met Ser Ile Tyr Ser Asn Gly Asp Lys Glu Asp Gly Arg Phe
305                 310                 315                 320

Thr Ala Gln Leu Asn Lys Ala Ser Gln Tyr Val Ser Leu Leu Ile Arg
                325                 330                 335

Asp Ser Gln Pro Ser Asp Ser Ala Thr Tyr Leu Cys Ala Ala Tyr Ser
            340                 345                 350

```
Gly Ala Gly Ser Tyr Gln Leu Thr Phe Gly Lys Gly Thr Lys Leu Ser
            355                 360                 365
Val Ile Pro Asn Ile Gln Asn Gly Gly Gly Ser Gly Gly Gly Gly
    370                 375                 380
Ser Gly Gly Gly Ser Gly Gly Gly Gly Ser Gly Gly Gly Gly Ser
385                 390                 395                 400
Gly Val Thr Gln Thr Pro Lys His Leu Ile Thr Ala Thr Gly Gln Arg
                405                 410                 415
Val Thr Leu Arg Cys Ser Pro Ala Met Asp His Pro Tyr Val Tyr Trp
                420                 425                 430
Tyr Lys Gln Ser Leu Asp Gln Gly Leu Gln Phe Leu Ile Gln Tyr Tyr
                435                 440                 445
Asn Gly Glu Glu Arg Ala Lys Gly Asn Ile Ser Glu Arg Phe Ser Ala
            450                 455                 460
Gln Gln Phe Pro Asp Leu His Ser Glu Leu Asn Leu Ser Ser Leu Glu
465                 470                 475                 480
Leu Gly Asp Ser Ala Leu Tyr Phe Cys Ala Ser Ser Val Glu Ser Ser
                485                 490                 495
Tyr Gly Tyr Thr Phe Gly Ser Gly Thr Arg Leu Thr Val Val Glu Asp
                500                 505                 510
Leu Lys Asn
        515

<210> SEQ ID NO 65
<211> LENGTH: 515
<212> TYPE: PRT
<213> ORGANISM: Homo sapiens

<400> SEQUENCE: 65

Met Lys Trp Val Thr Phe Ile Ser Leu Leu Phe Leu Phe Ser Ser Ala
1               5                   10                  15
Tyr Ser Glu Val Gln Leu Val Glu Ser Gly Gly Gly Leu Val Gln Pro
                20                  25                  30
Gly Gly Ser Leu Arg Leu Ser Cys Ala Ala Ser Gly Tyr Ser Phe Thr
            35                  40                  45
Gly Tyr Thr Met Asn Trp Val Arg Gln Ala Pro Gly Lys Gly Leu Glu
        50                  55                  60
Trp Val Ala Leu Ile Asn Pro Tyr Lys Gly Val Ser Thr Tyr Asn Gln
65                  70                  75                  80
Lys Phe Lys Asp Arg Phe Thr Ile Ser Val Asp Lys Ser Lys Asn Thr
                85                  90                  95
Ala Tyr Leu Gln Met Asn Ser Leu Arg Ala Glu Asp Thr Ala Val Tyr
                100                 105                 110
Tyr Cys Ala Arg Ser Gly Tyr Tyr Gly Asp Ser Asp Trp Tyr Phe Asp
                115                 120                 125
Val Trp Gly Gln Gly Thr Leu Val Thr Val Ser Ser Ala Ser Thr Lys
            130                 135                 140
Gly Pro Ser Val Phe Pro Leu Ala Pro Ser Ser Lys Ser Thr Ser Gly
145                 150                 155                 160
Gly Thr Ala Ala Leu Gly Cys Leu Val Lys Asp Tyr Phe Pro Glu Pro
                165                 170                 175
Val Thr Val Ser Trp Asn Ser Gly Ala Leu Thr Ser Gly Val His Thr
                180                 185                 190
Phe Pro Ala Val Leu Gln Ser Ser Gly Leu Tyr Ser Leu Ser Ser Val
```

```
            195                 200                 205
Val Thr Val Pro Ser Ser Leu Gly Thr Gln Thr Tyr Ile Cys Asn
210                 215                 220

Val Asn His Lys Pro Ser Asn Thr Lys Val Asp Lys Val Glu Pro
225                 230                 235                 240

Lys Ser Cys Asp Lys Thr His Thr Ser Pro Pro Ser Pro Ala Pro Pro
                245                 250                 255

Val Ala Gly Gln Lys Glu Val Glu Gln Asn Ser Gly Pro Leu Ser Val
            260                 265                 270

Pro Glu Gly Ala Ile Ala Ser Leu Asn Cys Thr Tyr Ser Asp Arg Arg
                275                 280                 285

Ser Gln Ser Phe Phe Trp Tyr Arg Gln Tyr Ser Gly Lys Ser Pro Glu
290                 295                 300

Leu Ile Met Ser Ile Tyr Ser Asn Gly Asp Lys Glu Asp Gly Arg Phe
305                 310                 315                 320

Thr Ala Gln Leu Asn Lys Ala Ser Gln Tyr Val Ser Leu Leu Ile Arg
                325                 330                 335

Asp Ser Gln Pro Ser Asp Ser Ala Thr Tyr Leu Cys Ala Ala Tyr Ser
                340                 345                 350

Gly Ala Gly Ser Tyr Gln Leu Thr Phe Gly Lys Gly Thr Lys Leu Ser
            355                 360                 365

Val Ile Pro Asn Ile Gln Asn Gly Gly Gly Ser Gly Gly Gly Gly
370                 375                 380

Ser Gly Gly Gly Gly Ser Gly Gly Gly Gly Ser Gly Gly Gly Gly Ser
385                 390                 395                 400

Gly Val Thr Gln Thr Pro Lys His Leu Ile Thr Ala Thr Gly Gln Arg
                405                 410                 415

Val Thr Leu Arg Cys Ser Pro Ala Met Asp His Pro Tyr Val Tyr Trp
                420                 425                 430

Tyr Lys Gln Ser Leu Asp Gln Gly Leu Gln Phe Leu Ile Gln Tyr Tyr
                435                 440                 445

Asn Gly Glu Glu Arg Ala Lys Gly Asn Ile Ser Glu Arg Phe Ser Ala
450                 455                 460

Gln Gln Phe Pro Asp Leu His Ser Glu Leu Asn Leu Ser Ser Leu Glu
465                 470                 475                 480

Leu Gly Asp Ser Ala Leu Tyr Phe Cys Ala Ser Ser Val Glu Ser Ser
                485                 490                 495

Tyr Gly Tyr Thr Phe Gly Ser Gly Thr Arg Leu Thr Val Val Glu Asp
                500                 505                 510

Leu Lys Asn
        515

<210> SEQ ID NO 66
<211> LENGTH: 515
<212> TYPE: PRT
<213> ORGANISM: Homo sapiens

<400> SEQUENCE: 66

Met Lys Trp Val Thr Phe Ile Ser Leu Leu Phe Leu Phe Ser Ser Ala
1               5                   10                  15

Tyr Ser Glu Val Gln Leu Val Glu Ser Gly Gly Gly Leu Val Gln Pro
                20                  25                  30

Gly Gly Ser Leu Arg Leu Ser Cys Ala Ala Ser Gly Tyr Ser Phe Thr
            35                  40                  45
```

-continued

```
Gly Tyr Thr Met Asn Trp Val Arg Gln Ala Pro Gly Lys Gly Leu Glu
     50                  55                  60

Trp Val Ala Leu Ile Asn Pro Tyr Lys Gly Val Ser Thr Tyr Asn Gln
 65                  70                  75                  80

Lys Phe Lys Asp Arg Phe Thr Ile Ser Val Asp Lys Ser Lys Asn Thr
                 85                  90                  95

Ala Tyr Leu Gln Met Asn Ser Leu Arg Ala Glu Asp Thr Ala Val Tyr
            100                 105                 110

Tyr Cys Ala Arg Ser Gly Tyr Tyr Gly Asp Ser Asp Trp Tyr Phe Asp
            115                 120                 125

Val Trp Gly Gln Gly Thr Leu Val Thr Val Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Gln Thr Tyr Ile Cys Asn
210                 215                 220

Val Asn His Lys Pro Ser Asn Thr Lys Val Asp Lys Lys Val Glu Pro
225                 230                 235                 240

Lys Ser Cys Asp Lys Thr His Thr Ser Pro Pro Ser Pro Ala Pro Pro
                245                 250                 255

Val Ala Gly Gly Val Thr Gln Thr Pro Lys His Leu Ile Thr Ala Thr
            260                 265                 270

Gly Gln Arg Val Thr Leu Arg Cys Ser Pro Arg Ser Gly Asp Leu Ser
        275                 280                 285

Val Tyr Trp Tyr Lys Gln Ser Leu Asp Gln Gly Leu Gln Phe Leu Ile
290                 295                 300

Gln Tyr Tyr Asn Gly Glu Glu Arg Ala Lys Gly Asn Ile Ser Glu Arg
305                 310                 315                 320

Phe Ser Ala Gln Gln Phe Pro Asp Leu His Ser Glu Leu Asn Leu Ser
                325                 330                 335

Ser Leu Glu Leu Gly Asp Ser Ala Leu Tyr Phe Cys Ala Ser Ser Val
            340                 345                 350

Glu Ser Ser Tyr Gly Tyr Thr Phe Gly Ser Gly Thr Arg Leu Thr Val
        355                 360                 365

Val Glu Asp Leu Lys Asn Gly Gly Gly Ser Gly Gly Gly Gly Ser
370                 375                 380

Gly Gly Gly Gly Ser Gly Gly Gly Ser Gly Gly Gly Gly Ser Gln
385                 390                 395                 400

Lys Glu Val Glu Gln Asn Ser Gly Pro Leu Ser Val Pro Glu Gly Ala
                405                 410                 415

Ile Ala Ser Leu Asn Cys Thr Tyr Ser Asp Arg Arg Ser Gln Ser Phe
            420                 425                 430

Phe Trp Tyr Arg Gln Tyr Ser Gly Lys Ser Pro Glu Leu Ile Met Ser
        435                 440                 445

Ile Tyr Ser Asn Gly Asp Lys Glu Asp Gly Arg Phe Thr Ala Gln Leu
450                 455                 460

Asn Lys Ala Ser Gln Tyr Val Ser Leu Leu Ile Arg Asp Ser Gln Pro
```

-continued

```
465                 470                 475                 480
Ser Asp Ser Ala Thr Tyr Leu Cys Ala Ala Tyr Ser Gly Ala Gly Ser
                    485                 490                 495
Tyr Gln Leu Thr Phe Gly Lys Gly Thr Lys Leu Ser Val Ile Pro Asn
                500                 505                 510
Ile Gln Asn
        515
```

ENGINEERED T CELL RECEPTORS AND IMMUNE THERAPY USING THE SAME

CROSS REFERENCE TO RELATED APPLICATIONS

This application is a continuation of U.S. application Ser. No. 16/180,980, filed 5 Nov. 2018, which claims the benefit of U.S. Provisional Application Ser. No. 62/582,202, filed 6 Nov. 2017, and German Patent Application No. 10 2017 125 888.4, filed 6 Nov. 2017, the content of each of these applications is herein incorporated by reference in their entirety. This application is related to PCT/EP2018/080176, filed 5 Nov. 2018, the content of which is incorporated herein by reference in its entirety.

REFERENCE TO SEQUENCE LISTING SUBMITTED AS A COMPLIANT ASCII TEXT FILE (.TXT)

Pursuant to the EFS-Web legal framework and 37 CFR §§ 1.821-825 (see MPEP § 2442.03(a)), a Sequence Listing in the form of an ASCII-compliant text file (entitled "Sequence_Listing_3000058-012002_ST25.txt" created on 26 Dec. 2019, and 66,603 bytes in size) is submitted concurrently with the instant application, and the entire contents of the Sequence Listing are incorporated herein by reference.

FIELD

The present invention pertains to antigen recognizing constructs against COL6A3 antigens. The invention in particular provides novel engineered T cell receptor (TCR) based molecules which are selective and specific for the tumor expressing antigen COL6A3. The TCR of the invention, and COL6A3 antigen binding fragments derived therefrom, are of use for the diagnosis, treatment and prevention of COL6A3 expressing cancerous diseases. Further provided are nucleic acids encoding the antigen recognizing constructs of the invention, vectors comprising these nucleic acids, recombinant cells expressing the antigen recognizing constructs and pharmaceutical compositions comprising the compounds of the invention.

BACKGROUND OF THE INVENTION

The collagens are a superfamily of proteins that play a role in maintaining the integrity of various tissues. Collagens are extracellular matrix proteins and have a triple-helical domain as their common structural element. Collagen VI is a major structural component of micro fibrils. The basic structural unit of collagen VI is a heterotrimer of the alpha 1(VI), alpha 2(VI), and alpha 3(VI) collagen chains. The alpha 1(VI) and alpha 2(VI) chains are encoded by the COL6A1 and COL6A2 genes, respectively. The protein encoded by the COL6A3 gene is the alpha 3 subunit of type VI collagen (alpha 3(VI) collagen chain) (Bertini et al., 2002 Eur. J. Paediatr. Neurol 6:193-8). COL6A3's gene expression was previously shown to be associated with the progression of breast cancer and was elevated in colon cancer (Smith M J, et al. "Analysis of differential gene expression in colorectal cancer and stroma using fluorescence-activated cell sorting purification" British journal of cancer. 2009; 100:1452-1464; Tilman G et al "Human periostin gene expression in normal tissues, tumors and melanoma: evidences for periostin production by both stromal and melanoma cells" Mol Cancer. 2007; 6:80) and as a prognosis marker of colorectal carcinoma (Qiao J et al. "Stroma derived COL6A3 is a potential prognosis marker of colorectal carcinoma revealed by quantitative proteomics" Oncotarget. 2015 Oct. 6; 6(30): 29929-29946). COL6A3 gene locates 2q37 in the human genome and contains 44 exons. The COL6A3 protein has 3177 amino acids and contains 12 Von Willebrand factor type A (vWA) domains, one fibronectin type 3 domain and one BPTI/Kunitz family of serine protease inhibitors (KU) domain.

Targets for T-cell based immunotherapy represent peptide epitopes derived from tumor-associated or tumor-specific proteins, which are presented by molecules of the major histocompatibility complex (MHC). These tumor associated antigens (TAAs) can be peptides derived from all protein classes, such as enzymes, receptors, transcription factors, etc. which are expressed and, as compared to unaltered cells of the same origin, usually up-regulated in cells of the respective tumor.

Specific elements of the cellular immune response are capable of selectively recognizing and destroying tumor cells. The isolation of tumor antigen-specific T cells from tumor-infiltrating cell populations or from peripheral blood suggests that such cells play an important role in natural immune defense against cancer. CD8-positive T cells in particular, which recognize class I molecules of the major histocompatibility complex (MHC)-bearing peptides of usually 8 to 10 amino acid residues derived from proteins or defective ribosomal products (DRiPs) located in the cytosol, play an important role in this response. The MHC-molecules of the human are also designated as human leukocyte-antigens (HLA).

A TCR is a heterodimeric cell surface protein of the immunoglobulin super-family, which is associated with invariant proteins of the CD3 complex involved in mediating signal transduction. TCRs exist as $\alpha\beta$ and $\gamma\delta$ heterodimers, which are structurally similar but have quite distinct anatomical locations and probably functions. The extracellular portion of native heterodimeric $\alpha\beta$TCR consists of two polypeptide chains, each of which has a membrane-proximal constant domain, and a membrane-distal variable domain. Each of the constant and variable domains includes an intra-chain disulfide bond. The variable domains contain the highly polymorphic loops analogous to the complementarity determining regions (CDRs) of antibodies. The use of TCR gene therapy overcomes a number of current hurdles. It allows equipping patients' own T cells with desired specificities and generation of sufficient numbers of T cells in a short period of time, avoiding their exhaustion. The TCR will be transduced into central memory T cells or T cells with stem cell characteristics, which may ensure better persistence and function upon transfer. TCR-engineered T cells will be infused into cancer patients rendered lymphopenic by chemotherapy or irradiation, allowing efficient engraftment but inhibiting immune suppression.

While advances have been made in the development of molecular-targeting drugs for cancer therapy, there remains a need in the art to develop new anti-cancer agents that specifically target molecules highly specific to cancer cells. The present description addresses that need by providing novel engineered COL6A3 TCRs, respective recombinant TCR constructs, nucleic acids, vectors and host cells that specifically bind COL6A3 epitope(s) as disclosed; and methods of using such molecules in the treatment of cancer.

SUMMARY OF THE INVENTION

In a first aspect the object of the invention is solved by an antigen recognizing construct comprising a first domain comprising three complementary determining regions (CDRs) according to SEQ ID NOs: 5 (CDRa1), 6 (CDRa2), and 7 (CDRa3), and a second domain comprising three complementary determining regions (CDRs) according to SEQ ID NOs: 13 (CDRb1), 14 (CDRb2), and 15 (CDRb3), wherein at least one of said complementary determining regions is replaced with at least one sequence selected from the group of: a) SEQ ID NO: 26 (CDRa1-mut1), and SEQ ID NOs: 37 to 49 (CDRb1-mut1 to CDRb1-mut13), preferably SEQ ID NO: 40, and b) mutated sequences of SEQ ID NO: 26, and SEQ ID NOs: 37 to 49, preferably SEQ ID NO: 40, comprising conservative amino acid exchanges.

In another aspect, CDRa1 of an antigen recognizing construct may have at least about 25%, at least about 30%, at least about 35%, at least about 40%, at least about 45%, at least about 50%, at least about 55%, at least about 60%, at least 65%, at least about 70%, at least about 75%, at least about 80%, at least about 85%, at least about 90%, at least about 95%, at least about 96%, at least about 97%, at least about 98%, or at least about 99% identity with the amino acid sequence according to SEQ ID NO: 5.

In another aspect, CDRa2 of an antigen recognizing construct may have at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% identity with the amino acid sequence according to SEQ ID NO: 6.

In another aspect, CDRa3 of an antigen recognizing construct may have at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% identity with the amino acid sequence according to SEQ ID NO: 7.

In another aspect, CDRb1 of an antigen recognizing construct may have at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% identity with the amino acid sequence according to SEQ ID NO: 13.

In another aspect, CDRb2 of an antigen recognizing construct may have at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% identity with the amino acid sequence according to SEQ ID NO: 14.

In another aspect, CDRb3 of an antigen recognizing construct may have at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, or at least about 99% identity with the amino acid sequence according to SEQ ID NO: 15.

In the context of the present invention, the inventors have identified improved engineered versions of the COL6A3 TCR R4P3F9 comprising mutated CDR1 sequences in the alpha and beta chain(s) that are improving stability, recognition and selectivity of the parental R4P3F9. These maturated TCR variants have been selected in a two-step method, wherein one step selects for stability and the second for affinity of the variants (see examples). While the inventive TCRs comprise mutated CDR1 regions, it is likely that CDR2 and or CDR3 can be mutated as well in order to increase binding affinity/specificity and/or selectivity and such mutated CDRs ideally could be included in the existing constructs.

The affinity maturation identified variants with considerably stronger binding activity towards HLA-A*02/COL6A3-peptide, while retaining or even improving specificity. Compared to the parental TCR C-1 (R4P3F9 TCR comprising wild type CDRs, see Table 5), all variants of the invention improved IFN-gamma release with higher levels reached already for lower peptide loading concentrations.

Within the variable domain, CDR1 and CDR2 are found in the variable (V) region of a polypeptide chain, and CDR3 includes some of V, all of diversity (D) and joining (J) regions. It is assumed that CDR3 is the most variable and is the main CDR responsible for specifically and selectively recognizing an antigen. Surprisingly, for some TCRs CDR1 seems also to make contacts to the peptide and thus is also responsible for selective recognition. In the present case, without being bound to a specific theory, the mutated CDR1b seems to interact with position 8 of the COL6A3-peptide.

Native alpha-beta heterodimeric TCRs have an alpha chain and a beta chain. Each alpha chain comprises variable, joining and constant regions, and the beta chain also usually contains a short diversity region between the variable and joining regions, but this diversity region is often considered as part of the joining region. Each variable region comprises three CDRs (Complementarity Determining Regions) embedded in a framework sequence, one being the hypervariable region named CDR3. There are several types of alpha chain variable (Vα) regions and several types of beta chain variable (Vβ) regions distinguished by their framework, CDR1 and CDR2 sequences, and by a partly defined CDR3 sequence. The Vα types are referred to in IMGT nomenclature by a unique TRAV number, Vβ types are referred to by a unique TRBV number.

Preferably, an antigen recognizing construct of the invention comprises the respective CDR1 to CDR3 of one individual herein disclosed engineered TCR variable region of the invention. Preferred are antigen recognizing constructs (e.g., αβ and γδ TCRs) of the invention which comprise at least one, preferably two, maturated CDR1 sequences.

The CDR-variants as disclosed herein—in particular the CDR1-variants—can be modified by the substitution of one or more residues at different, possibly selective, sites within the peptide chain, if not otherwise stated. Such substitutions are of a conservative nature where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often show correlation with similarities in size, charge, polarity, and hydrophobicity between the original amino acid and its replacement, and such is the basis for defining "conservative substitutions". Preferred conservative substitutions are herein defined as exchanges within one of the following five groups: Group 1—small aliphatic, nonpolar or slightly polar residues (Ala, Ser, Thr, Pro, Gly); Group 2—polar, negatively charged residues and their amides (Asp, Asn, Glu, Gln); Group 3—polar, positively charged residues (His, Arg, Lys); Group 4—large, aliphatic, nonpolar residues (Met, Leu, Ile, Val, Cys); and Group 5—large, aromatic residues (Phe, Tyr, Trp).

Less conservative substitutions might involve the replacement of one amino acid by another that has similar characteristics but is somewhat different in size, such as replacement of an alanine by an isoleucine residue.

The term "specificity" or "antigen specificity" or "specific for" a given antigen, as used herein means that the antigen recognizing construct can specifically bind to said antigen, preferably a COL6A3 antigen, more preferably with high avidity, when said antigen is presented by HLA, preferably HLA A2. For example, a TCR, as antigen recognizing construct, may be considered to have "antigenic specificity" for COL6A3 antigens, if T cells expressing the TCR in response to COL6A3 presenting HLA secrete at least about 200 pg/ml or more (e.g., 250 pg/ml or more, 300 pg/ml or more, 400 pg/ml or more, 500 pg/ml or more, 600 pg/ml or more, 700 pg/ml or more, 1000 pg ml or more, 2,000 pg/ml or more, 2,500 pg/ml or more, 5,000 pg/ml or more) of interferon γ (IFN-γ) upon co-culture with HLA A2 target cells pulsed with a low concentration of a COL6A3 antigen, such as the COL6A3 epitopes and antigens provided herein below (e.g., about 10-11 mol/l, 10-10 mol/l, 10-9 mol/l, 10-8 mol/l, 10-7 mol/l, 10-6 mol/l, 10-5 mol/l). Alternatively, or additionally, a TCR may be considered to have "antigenic specificity" for COL6A3, if T cells expressing the TCR secrete at least twice as much IFN-γ as the untransduced background level of IFN-γ upon co-culture with target cells pulsed with a low concentration of COL6A3 antigens. Such a "specificity" as described above can—for example—be analyzed with an ELISA.

In one alternative or additional embodiment of the invention, the antigen recognizing construct is stable, and capable of specifically and/or selectively binding to a COL6A3 antigen; preferably wherein the COL6A3 antigen is a protein epitope or peptide having an amino acid sequence shown in SEQ ID NO: 1 or a variant thereof, wherein the variant is an amino acid deletion, addition, insertion or substitution of not more than three, preferably two and most preferably not more than one amino acid position.

The term "selectivity" or "selective recognizing/binding" is understood to refer to the property of an antigen recognizing construct, such as a TCR or antibody, to selectively recognize or bind to preferably only one specific epitope and preferably shows no or substantially no cross-reactivity to another epitope. Preferably "selectivity" or "selective recognizing/binding" means that the antigen recognizing construct (e.g., a TCR) selectively recognizes or binds to preferably only one specific epitope and preferably shows no or substantially no cross-reactivity to another epitope, wherein said epitope is unique for one protein, such that the antigen recognizing construct shows no or substantially no cross-reactivity to another epitope and another protein.

The antigen recognizing construct according to the invention is preferably selected from an antibody, or derivative or fragment thereof, a bispecific molecule, or a T cell receptor (TCR), or a derivative or fragment thereof. A derivative or fragment of an antibody or TCR of the invention shall preferably retain the antigen binding/recognizing ability of the parent molecule, in particular its specificity and/or selectivity as explained above.

In an embodiment of the invention, the inventive engineered TCRs are able to recognize COL6A3 antigens in a major histocompatibility complex (MHC) class I-dependent manner. "MHC class I-dependent manner," as used herein, means that the TCR elicits an immune response upon binding to COL6A3 peptide antigens within the context of an MHC class I molecule. The MHC class I molecule can be any MHC class I molecule known in the art, e.g., HLA-A molecules. In a preferred embodiment of the invention, the MHC class I molecule is an HLA-A2 molecule.

The invention provides both single chain antigen recognizing construct and double chain recognizing constructs, as well as other variant molecules. The invention in particular provides an engineered TCR as antigen recognizing construct, or fragment or derivative thereof. The engineered TCR preferably is of human origin, which is understood as being generated from a human TCR locus and therefore comprising human TCR sequences. Furthermore, the TCR of the invention is characterized as affinity maturated TCR, which is capable of specifically and selectively recognizing COL6A3 peptide antigen. Another embodiment of the invention additionally or alternatively provides the antigen recognizing construct described above, which induces an immune response, preferably wherein the immune response is characterized by an increase in interferon (IFN) γ levels.

TCRs of the invention may be provided as single chain α or β, or γ and δ, molecules, or alternatively as double chain constructs composed of both the α and β chain, or γ and δ chain.

Most preferably, in some additional embodiments, wherein the disclosure refers to antigen recognizing constructs comprising any one, two or all of the CDR1 to CDR3 regions of the herein disclosed engineered TCR chains (see table 1). Antigen recognizing constructs may be preferred, which comprise the natural or the engineered CDR sequence having three, two, and preferably only one, modified amino acid residues. A modified amino acid residue may be selected from an amino acid insertion, deletion or substitution. Most preferred is that the three, two, preferably one modified amino acid residue is the first or last amino acid residue of the respective CDR sequence. If the modification is a substitution then it is preferable in some embodiments that the substitution is a conservative amino acid substitution.

The inventive TCRs may further comprise a constant region derived from any suitable species, such as any mammal, e.g., human, rat, monkey, rabbit, donkey, or mouse. In an embodiment of the invention, the inventive TCRs further comprise a human constant region. In some preferred embodiments, the constant region of the TCR of the invention may be slightly modified, for example, by the introduction of heterologous sequences, preferably mouse sequences, which may increase TCR expression and stability. Also, further stabilizing mutations as known from the state of the art (e.g., DE 10 2016 123 893.7) may be introduced, such as replacement of unfavorable amino acids in the V regions and/or the introduction of a disulfide bridge between the TCR C domains and the removal of unpaired cysteine.

As used herein, the term "murine" or "human," when referring to an antigen recognizing construct, or a TCR, or any component of a TCR described herein (e.g., complementarity determining region (CDR), variable region, constant region, α chain, and/or β chain), means a TCR (or component thereof), which is derived from a mouse or a human unrearranged TCR locus, respectively.

In an embodiment of the invention, chimeric TCR are provided, wherein the TCR chains comprise sequences from multiple species. Preferably, a TCR of the invention may comprise an α chain comprising a human variable region of an α chain and, for example, a murine constant region of a murine TCR α chain.

In one embodiment, the TCR of the invention is a human TCR comprising human variable regions according to the above embodiments and human constant regions.

The TCR of the invention may be provided as a single chain TCR (scTCR). A scTCR can comprise a polypeptide of a variable region of a first TCR chain (e.g., an alpha chain) and a polypeptide of an entire (full-length) second TCR chain (e.g., a beta chain), or vice versa. Furthermore, the scTCR can optionally comprise one or more linkers which join the two or more polypeptides together. The linker can be, for instance, a peptide, which joins together two single chains, as described herein. Also provided is such a scTCR of the invention, which is fused to a human cytokine, such as IL-2, IL-7 or IL-15.

The antigen recognizing construct according to the invention can also be provided in the form of a multimeric complex, comprising at least two scTCR molecules, wherein said scTCR molecules are each fused to at least one biotin moiety, and wherein said scTCRs are interconnected by biotin-streptavidin interaction to allow the formation of said multimeric complex. Similar approaches for the generation of multimeric TCR are also possible and included in this disclosure. Also provided are multimeric complexes of a higher order, comprising more than two scTCR of the invention.

For the purposes of the present invention, a TCR is a moiety having at least one TCR alpha or gamma and/or TCR beta or delta variable domain. Generally, they comprise both a TCR alpha variable domain and a TCR beta variable domain. They may be αβ heterodimers or may be in single chain format. For use in adoptive therapy, an αβ heterodimeric TCR may, for example, be transfected as full length chains having both cytoplasmic and transmembrane domains. If desired, an introduced disulfide bond between residues of the respective constant domains may be present.

In a preferred embodiment, the antigen recognizing construct is a human TCR, or fragment or derivative thereof. A human TCR or fragment or derivative thereof is a TCR, which comprises over 50% of the corresponding human TCR sequence. Preferably, only a small part of the TCR sequence is of artificial origin or derived from other species. It is known, however, that chimeric TCRs, e.g., derived from human origin with murine sequences in the constant domains, are advantageous. Particularly preferred are, therefore, TCRs in accordance with the present invention, which contains murine sequences in the extracellular part of their constant domains.

Thus, it is also preferred that the inventive antigen recognizing construct is able to recognize its peptide antigen in a human leucocyte antigen (HLA) dependent manner, preferably in an HLA-A02 dependent manner. The term "HLA dependent manner" in the context of the present invention means that the antigen recognizing construct binds to the antigen only in the event that the antigenic peptide is presented by said HLA.

The antigen recognizing construct in accordance with the invention in one embodiment preferably induces an immune response, preferably wherein the immune response is characterized by the increase in interferon (IFN) γ levels.

The term "polypeptide" as used herein includes oligopeptides and refers to a single chain of amino acids connected by one or more peptide bonds. With respect to the inventive polypeptides, the functional portion can be any portion comprising contiguous amino acids of the TCR (or functional variant thereof), of which it is a part, provided that the functional portion specifically binds to a COL6A3 antigen, preferably as disclosed herein in table 1. The term "functional portion" when used in reference to a TCR (or functional variant thereof) refers to any part or fragment of the TCR (or functional variant thereof) of the invention, which part or fragment retains the biological activity of the TCR (or functional variant thereof), of which it is a part (the parent TCR or parent functional variant thereof). Functional portions encompass, for example, those parts of a TCR (or functional variant thereof) that retain the ability to specifically bind to a COL6A3 antigen (in an HLA-A2-dependent manner), or detect, treat, or prevent cancer, to a similar extent, the same extent, or to a higher extent, as the parent TCR (or functional variant thereof).

The functional portion can comprise additional amino acids at the amino or carboxy terminus of the portion, or at both termini, in which additional amino acids are not found in the amino acid sequence of the parent TCR or functional variant thereof. Desirably, the additional amino acids do not interfere with the biological function of the functional portion, e.g., specifically binding to COL6A3 antigens; and/or having the ability to detect cancer, treat or prevent cancer, etc. More desirably, the additional amino acids enhance the biological activity, as compared to the biological activity of the parent TCR or functional variant thereof.

As already mentioned above, the binding functionality of the TCR of the invention may be provided in the framework of an antibody. The term "antibody" in its various grammatical forms is used herein to refer to immunoglobulin molecules and immunologically active portions of immunoglobulin molecules, i.e., molecules that contain an antigen-binding site or a paratope. Such molecules are also referred to as "antigen binding fragments" of immunoglobulin molecules. The invention further provides an antibody, or antigen binding portion thereof, which specifically binds to the antigens described herein. The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form.

The invention also provides antigen binding portions of any of the antibodies described herein. The antigen binding portion can be any portion that has at least one antigen binding site, such as Fab, F(ab')2, dsFv, scFv, diabodies, and triabodies. A single-chain variable region fragment (scFv) antibody fragment, which consists of a truncated Fab fragment comprising the variable (V) domain of an antibody heavy chain linked to a V domain of a light antibody chain via a synthetic peptide, can be generated using routine recombinant DNA technology techniques. Similarly, disulfide-stabilized variable region fragments (dsFv) can be prepared by recombinant DNA technology, antibody fragments of the invention, however, are not limited to these exemplary types of antibody fragments. Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

Suitable methods of making antibodies are known in the art. For instance, standard hybridoma methods are described in, e.g., Kohler and Milstein, Eur. J. Immunol, 5, 51 1-519 (1976), Harlow and Lane (eds.), Antibodies: A Laboratory Manual, CSH Press (1988), and C. A. Janeway et al. (eds.), Immunobiology, 8 Ed., Garland Publishing, New York, N.Y. (2011)). Alternatively, other methods, such as EBV-hybridoma methods (Haskard and Archer, J. Immunol. Methods, 74(2), 361-67 (1984), and Roder et al, Methods Enzymol, 121, 140-67 (1986)), and bacteriophage vector expression systems (see, e.g., Huse et al., Science, 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266.

Some embodiments of the invention also pertain to TCRs, or functional fragments and polypeptides thereof, which are soluble TCRs. As used herein, the term "soluble T-cell receptor" refers to single chain or heterodimeric truncated variants of native TCRs, which comprise at least the variable domains of the TCR α-chain and β-chain linked by a polypeptide linker (SEQ ID NOs: 22, 24, 25 and 27). Soluble variants of TCRs usually lack at least the transmembrane and cytosolic domains of the native protein; sometimes preferably such soluble constructs do not comprise any constant domain sequences. The soluble T-cell receptor constructs of the invention, in preferred embodiments, comprise constructs consisting of α- and β-chain variable domain sequences as provided herein, connected by a suitable linker sequence. The variable domain sequence (amino acid or nucleic acid) of the soluble TCR α-chain and β-chains may be identical to the corresponding sequences in a native TCR or may comprise variants of soluble TCR α-chain and β-chain variable domain sequences, as compared to the corresponding native TCR sequences. The term "soluble T-cell receptor" as used herein encompasses soluble TCRs with variant or non-variant soluble TCR α-chain and β-chain variable domain sequences. The variations may be in the framework and/or CDR regions of the soluble TCR α-chain and β-chain variable domain sequences and can include, but are not limited to, amino acid deletion, insertion, substitution mutations as well as changes to the nucleic acid sequence, which do not alter the amino acid sequence. Soluble TCR of the invention in any case retain or preferentially improve the binding functionality of their parental TCR molecules.

The above problem is further solved by a nucleic acid encoding for an antigen recognizing construct of the invention, or any of the aforementioned protein or polypeptide constructs. The nucleic acid preferably (a) has a strand encoding for an antigen recognizing construct according to the invention; (b) has a strand complementary to the strand in (a); or (c) has a strand that hybridizes under stringent conditions with a molecule as described in (a) or (b). Stringent conditions are known to the person of skill in the art, specifically from Sambrook et al, "Molecular Cloning". In addition to that, the nucleic acid optionally has further sequences, which are necessary for expressing the nucleic acid sequence corresponding to the protein, specifically for expression in a mammalian/human cell. The nucleic acid used can be contained in a vector suitable for allowing expression of the nucleic acid sequence corresponding to the polypeptide in a cell. However, the nucleic acids can also be used to transform an antigen-presenting cell, which may not be restricted to classical antigen-presenting cells, such as dendritic cells, in such a way that they themselves produce the corresponding proteins on their cellular surface.

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and can contain a natural, non-natural or altered internucleotide linkage, such as a phosphoroamidate linkage or a phosphorothioate linkage, instead of the phosphodiester found between the nucleotides of an unmodified oligonucleotide.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication. The nucleic acid can comprise any nucleotide sequence, which encodes any of the TCRs, polypeptides, or proteins, or functional portions or functional variants thereof described herein.

Furthermore, the invention provides a vector comprising a nucleic acid in accordance to the invention as described above. Desirably, the vector is an expression vector or a recombinant expression vector. The term "recombinant expression vector" refers in context of the present invention to a nucleic acid construct that allows for the expression of an mRNA, protein or polypeptide in a suitable host cell. The recombinant expression vector of the invention can be any suitable recombinant expression vector and can be used to transform or transfect any suitable host. Suitable vectors include those designed for propagation and expansion or for expression or both, such as plasmids and viruses. Examples of animal expression vectors include pEUK-Cl, pMAM, and pMAMneo. Preferably, the recombinant expression vector is a viral vector, e.g., a retroviral vector. The recombinant expression vector comprises regulatory sequences, such as transcription and translation initiation and termination codons, which are specific to the type of host cell (e.g., bacterium, fungus, plant, or animal), into which the vector is to be introduced and in which the expression of the nucleic acid of the invention may be performed. Furthermore, the vector of the invention may include one or more marker genes, which allow for selection of transformed or transfected hosts. The recombinant expression vector can comprise a native or normative promoter operably linked to the nucleotide sequence encoding the constructs of the invention, or to the nucleotide sequence, which is complementary to or which hybridizes to the nucleotide sequence encoding the constructs of the invention. The selections of promoters include, e.g., strong, weak, inducible, tissue-specific and developmental-specific promoters. The promoter can be a non-viral promoter or a viral promoter. The inventive recombinant expression vectors can be designed for either transient expression, for stable expression, or for both. Also, the recombinant expression vectors can be made for constitutive expression or for inducible expression.

The invention also pertains to a host cell comprising an antigen recognizing construct in accordance with the invention. Specifically, the host cell of the invention comprises a nucleic acid, or a vector as described herein above. The host cell can be a eukaryotic cell, e.g., plant, animal, fungi, or algae, or can be a prokaryotic cell, e.g., bacteria or protozoa.

The host cell can be a cultured cell or a primary cell, i.e., isolated directly from an organism, e.g., a human. The host cell can be an adherent cell or a suspended cell, i.e., a cell that grows in suspension. For purposes of producing a recombinant TCR, polypeptide, or protein, the host cell is preferably a mammalian cell, e.g., Chinese Hamster Ovary (CHO) cell. Most preferably, the host cell is a human cell. While the host cell can be of any cell type, can originate from any type of tissue, and can be of any developmental stage, the host cell preferably is a peripheral blood leukocyte (PBL) or a peripheral blood mononuclear cell (PBMC). More preferably, the host cell is a T cell. The T cell can be any T cell, such as a cultured T cell, e.g., a primary T cell, or a T cell from a cultured T cell line, e.g., Jurkat, SupT1, etc., or a T cell obtained from a mammal, preferably a T cell or T cell precursor from a human patient. If obtained from a mammal, the T cell can be obtained from numerous sources, including but not limited to blood, bone marrow, lymph node, the thymus, or other tissues or fluids. T cells can also be enriched for or purified. Preferably, the T cell is a human T cell. More preferably, the T cell is a T cell isolated from a human. The T cell can be any type of T cell and can be of any developmental stage, including but not limited to, CD4-positive and/or CD8-positive, CD4-positive helper T cells, e.g., Th1 and Th2 cells, CD8-positive T cells (e.g., cytotoxic T cells), tumor infiltrating cells (TILs), memory T cells, naive T cells, and the like. Preferably, the T cell is a CD8-positive T cell or a CD4-positive T cell.

Preferably, the host cell of the invention is a lymphocyte, preferably, a T lymphocyte, such as a CD4-positive or CD8-positive T-cell. The host cell furthermore preferably is a tumor reactive T cell specific for COL6A3 expressing tumor cells.

One further aspect of the present invention relates to the herein disclosed antigen recognizing constructs, nucleic acids, vectors, pharmaceutical compositions and/or host cell for use in medicine. The use in medicine in one preferred embodiment includes the use in the diagnosis, prevention and/or treatment of a tumor disease, such as a malignant or benign tumor disease. The tumor disease is, for example, a tumor disease characterized by the expression of COL6A3, in a cancer or tumor cell of said tumor disease.

With respect to the above mentioned medical applications of the antigen recognizing constructs and other materials derived therefrom, the to be treated and/or diagnosed cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vagina, cancer of the vulva, chronic lymphocytic leukemia, chronic myeloid cancer, colon cancer, esophageal cancer, cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, cancer of the oropharynx, ovarian cancer, cancer of the penis, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, cancer of the uterus, ureter cancer, and urinary bladder cancer. A preferred cancer is cancer is cancer of the uterine cervix, oropharynx, anus, anal canal, anorectum, vagina, vulva, or penis. A particularly preferred cancer is a COL6A3 positive cancer, including gastrointestinal and gastric cancer.

The constructs, proteins, TCRs, antibodies, polypeptides and nucleic acids of the invention are in particular for use in immune therapy, preferably, in adoptive T cell therapy. The administration of the compounds of the invention can, for example, involve the infusion of T cells of the invention into said patient. Preferably, such T cells are autologous T cells of the patient and in vitro transduced with a nucleic acid or antigen recognizing construct of the present invention.

WO 2016/011210 discloses engineered cells for adoptive therapy, including NK cells and T cells, and compositions containing the cells, and methods for their administration to subjects. The cells can contain genetically engineered antigen receptors that specifically bind to antigens, such as chimeric antigen receptors (CARs) and costimulatory receptors.

The object of the invention is also solved by a method of manufacturing a COL6A3 specific antigen recognizing construct expressing cell line, comprising
a. providing a suitable host cell,
b. providing a genetic construct comprising a coding sequence encoding the antigen recognizing construct according to any of claims 1 to 4,
c. introducing said genetic construct into said suitable host cell, and
d. expressing said genetic construct by said suitable host cell.

The method may further comprise a step of cell surface presentation of said antigen recognizing construct on said suitable host cell.

In other preferred embodiments, the genetic construct is an expression construct comprising a promoter sequence operably linked to said coding sequence.

Preferably, said antigen recognizing construct is of mammalian origin, preferably of human origin. The preferred suitable host cell for use in the method of the invention is a mammalian cell, such as a human cell, in particular a human T lymphocyte. T cells for use in the invention are described in detail herein above.

Also encompassed by the invention are embodiments, wherein said antigen recognizing construct is a modified TCR, wherein said modification is the addition of functional domains, such as a label or a therapeutically active substance. Furthermore, encompassed are TCR having alternative domains, such as an alternative membrane anchor domain instead of the endogenous transmembrane region.

Desirably, the transfection system for introducing the genetic construct into said suitable host cell is a retroviral vector system. Such systems are well known to the skilled artisan.

Also comprised by the present invention is in one embodiment the additional method step of isolation and purification of the antigen recognizing construct from the cell and, optionally, the reconstitution of the translated antigen recognizing construct-fragments in a T-cell.

In an alternative aspect of the invention a T-cell is provided obtained or obtainable by a method for the production of a T cell receptor (TCR), which is specific for tumorous cells and has high avidity as described herein above. Such a T cell is depending on the host cell used in the method of the invention, for example, a human or non-human T-cell, preferably a human TCR.

The inventive TCRs, polypeptides, proteins, (including functional variants thereof), nucleic acids, recombinant expression vectors, host cells (including populations thereof), and antibodies (including antigen binding portions thereof), can be isolated and/or purified. The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70% o, 80%, 90%, 95%, or can be 100%.

The inventive antigen recognizing constructs, TCRs, polypeptides, proteins (including functional variants thereof), nucleic acids, recombinant expression vectors, host cells (including populations thereof), and antibodies (including antigen binding portions thereof), all of which are collectively referred to as "inventive TCR materials" hereinafter, can be formulated into a composition, such as a pharmaceutical composition. In this regard, the invention provides a pharmaceutical composition comprising any of the antigen recognizing constructs, TCRs, polypeptides, proteins, functional portions, functional variants, nucleic acids, expression vectors, host cells (including populations thereof), and antibodies (including antigen binding portions thereof) described herein, and a pharmaceutically acceptable carrier, excipient and/or stabilizer. The inventive pharmaceutical compositions containing any of the inventive TCR materials can comprise more than one inventive TCR material, e.g., a polypeptide and a nucleic acid, or two or more different TCRs (including functional portions and functional variants thereof). Alternatively, the pharmaceutical composition can comprise an inventive TCR material in combination with another pharmaceutically active agent(s) or drug(s), such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. Preferably, the carrier is a pharmaceutically acceptable carrier. With respect to pharmaceutical compositions, the carrier can be any of those conventionally used for the particular inventive TCR material under consideration. Such pharmaceutically acceptable carriers are well-known to those skilled in the art and are readily available to the public. It is preferred that the pharmaceutically acceptable carrier be one, which has no detrimental side effects or toxicity under the conditions of use.

Thus, also provided is a pharmaceutical composition, comprising any of the herein described products of the invention and TCR materials of the invention, specifically any proteins, nucleic acids or host cells. In a preferred embodiment the pharmaceutical composition is for immune therapy, preferably adoptive cell therapy.

Preferably, the inventive TCR material is administered by injection, e.g., intravenously. When the inventive TCR material is a host cell expressing the inventive TCR (or functional variant thereof), the pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, Ill.), PLASMA-LYTE A (Baxter, Deerfield, Ill.), about 5% dextrose in water, or Ringer's lactate. In an embodiment, the pharmaceutically acceptable carrier is supplemented with human serum albumin.

For purposes of the invention, the amount or dose (e.g., numbers of cells when the inventive TCR material is one or more cells) of the inventive TCR material administered may be sufficient to affect, e.g., a therapeutic or prophylactic response, in the subject or animal over a reasonable time frame. For example, the dose of the inventive TCR material should be sufficient to bind to a cancer antigen, or detect, treat or prevent cancer in a period of from about 2 hours or longer, e.g., 12 to 24 or more hours, from the time of administration. In certain embodiments, the time period could be even longer. The dose will be determined by the efficacy of the particular inventive TCR material and the condition of the animal (e.g., human), as well as the body weight of the animal (e.g., human) to be treated.

It is contemplated that the inventive pharmaceutical compositions, TCRs (including functional variants thereof), polypeptides, proteins, nucleic acids, recombinant expression vectors, host cells, or populations of cells can be used in methods of treating or preventing cancer, or COL6A3-positive premalignancy. The inventive TCRs (and functional variants thereof) are believed to bind specifically to COL6A3 antigen, such that the TCR (or related inventive polypeptide or protein and functional variants thereof), when expressed by a cell, is able to mediate an immune response against a target cell expressing the COL6A3 antigens of the invention. In this regard, the invention provides a method of treating or preventing a condition, in particular cancer, in a mammal, comprising administering to the mammal any of the pharmaceutical compositions, antigen recognizing constructs, in particular TCRs (and functional variants thereof), polypeptides, or proteins described herein, any nucleic acid or recombinant expression vector comprising a nucleotide sequence encoding any of the TCRs (and functional variants thereof), polypeptides, proteins described herein, or any host cell or population of cells comprising a recombinant vector, which encodes any of the constructs of the invention (and functional variants thereof), polypeptides, or proteins described herein, in an amount effective to treat or prevent the condition in the mammal, wherein the condition is cancer, preferably COL6A3 positive cancer.

Examples of pharmaceutically acceptable carriers or diluents useful in the present invention include stabilizers such as SPGA, carbohydrates (e.g., sorbitol, mannitol, starch, sucrose, glucose, dextran), proteins such as albumin or casein, protein containing agents such as bovine serum or skimmed milk and buffers (e.g., phosphate buffer).

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of a condition in a mammal. Furthermore, the treatment or prevention provided by the inventive method can include treatment or prevention of one or more conditions or symptoms of the condition, e.g., cancer, being treated or prevented. For example, treatment or prevention can include promoting the regression of a tumor. Also, for purposes herein, "prevention" can encompass delaying the onset of the condition, or a symptom or condition thereof.

The present invention also relates to a method of treating cancer comprising administering a TCR, a nucleic acid, or a host cell of the present description in combination with at least one chemotherapeutic agent and/or radiation therapy.

Also provided is a method of treating cancer in a subject in need thereof, comprising:
  a) isolating a cell from said subject;
  b) transforming the cell with at least one vector encoding an antigen recognizing construct of the present invention to produce a transformed cell;

c) expanding the transformed cell to produce a plurality of transformed cells; and
d) administering the plurality of transformed cells to said subject.

Also provided is a method of treating cancer in a subject in need thereof, comprising:
a) isolating a cell from a healthy donor;
b) transforming the cell with a vector encoding an antigen recognizing construct of the present invention to produce a transformed cell;
c) expanding the transformed cell to produce a plurality of transformed cells; and
d) administering the plurality of transformed cells to said subject.

Also provided is a method of detecting cancer in a biological sample comprising:
a) contacting the biological sample with an antigen recognizing construct of the present description;
b) detecting binding of the antigen recognizing construct to the biological sample.

In some embodiments, the method of detecting cancer is carried out in vitro, in vivo or in situ.

Also provided is a method of detecting the presence of a condition in a mammal. The method comprises (i) contacting a sample comprising one or more cells from the mammal with any of the inventive TCRs (and functional variants thereof), polypeptides, proteins, nucleic acids, recombinant expression vectors, host cells, populations of cells, antibodies, or antigen binding portions thereof, or pharmaceutical compositions described herein, thereby forming a complex, and (ii) detecting the complex, wherein detection of the complex is indicative of the presence of the condition in the mammal, wherein the condition is cancer, such as a COL6A3-positive malignancy.

With respect to the inventive method of detecting a condition in a mammal, the sample of cells can be a sample comprising whole cells, lysates thereof, or a fraction of the whole cell lysates, e.g., a nuclear or cytoplasmic fraction, a whole protein fraction, or a nucleic acid fraction.

For purposes of the inventive detecting method, the contacting can take place in vitro or in vivo with respect to the mammal. Preferably, the contacting is in vitro.

Also, detection of the complex can occur through any number of ways known in the art. For instance, the inventive antigen recognizing constructs (and functional variants thereof), polypeptides, proteins, nucleic acids, recombinant expression vectors, host cells, populations of cells, or antibodies or TCRs, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

For purposes of the inventive methods, wherein host cells or populations of cells are administered, the cells can be cells that are allogeneic or autologous to the mammal. Preferably, the cells are autologous to the mammal.

With respect to the above mentioned medical applications of the TCR material of the invention, the to be treated and/or diagnosed cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vagina, cancer of the vulva, chronic lymphocytic leukemia, chronic myeloid cancer, colon cancer, esophageal cancer, cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, cancer of the oropharynx, ovarian cancer, cancer of the penis, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, cancer of the uterus, ureter cancer, and urinary bladder cancer. A preferred cancer is cancer of the uterine cervix, oropharynx, anus, anal canal, anorectum, vagina, vulva, or penis. A particularly preferred cancer is a COL6A3 positive cancer, such as gastrointestinal or gastric cancer.

In general, the invention provides a method for treating a subject suffering from a tumor or tumor disease comprising the administration of the antigen recognizing constructs, nucleic acids, vectors, pharmaceutical compositions and/or host cell as disclosed by the present invention. Preferably the subject is a subject in need of such a treatment. The subject in preferred embodiments is a mammalian subject, preferably a human patient, suffering from a tumor or tumor disease, which is COL6A3-positive.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention will now be further described in the following examples with reference to the accompanying figures and sequences, nevertheless, without being limited thereto. For the purposes of the present invention, all references as cited herein are incorporated by reference in their entireties. In the Figures and Sequences.

TABLE 1

Figure 1:
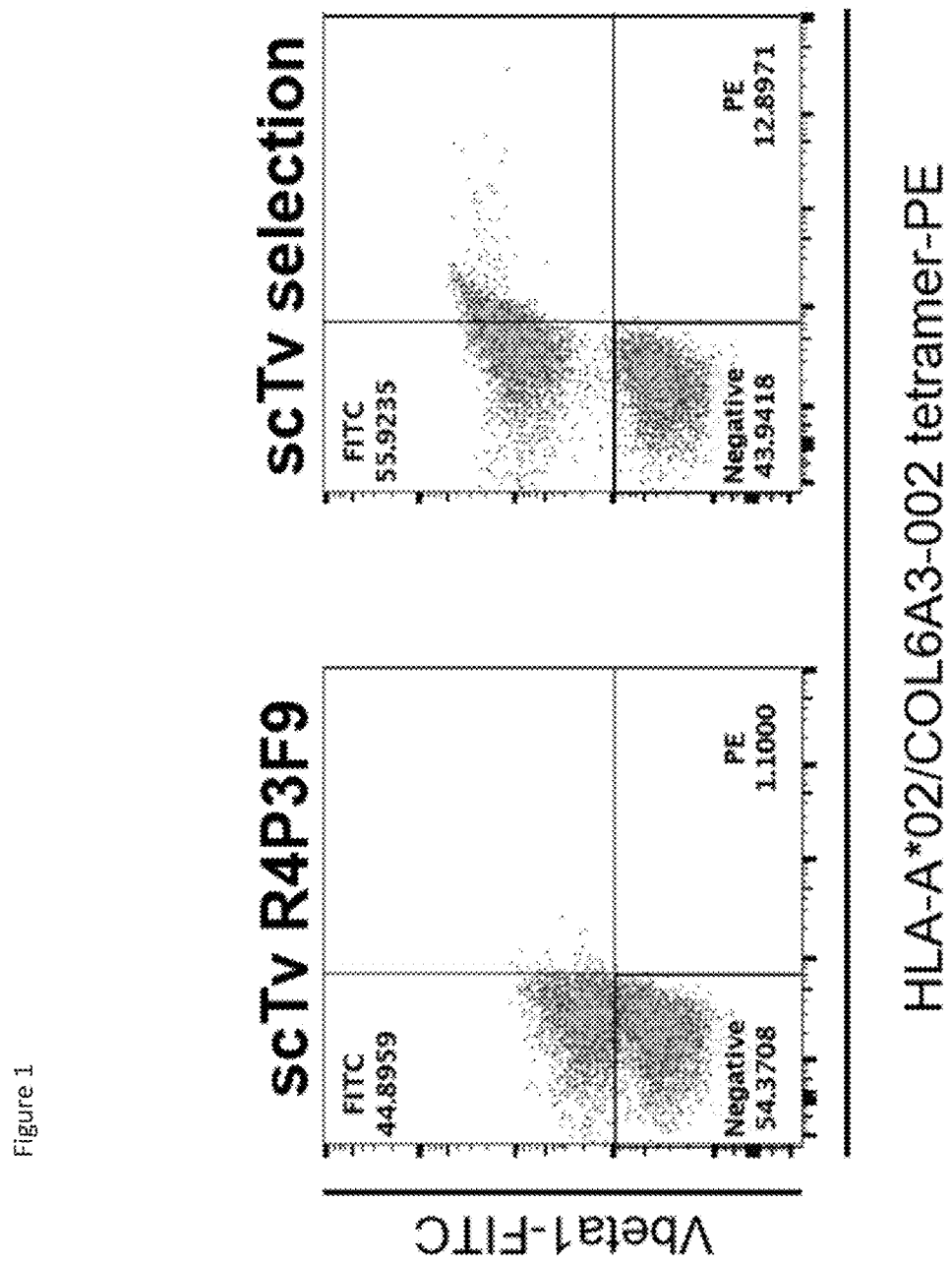
FIG. 1 shows the conversion of a TCR into stabilized Vα/Vβ single-chain TCR (scTv) via yeast surface display. ScTv molecules displayed on the surface of transformed *Saccharomyces cerevisiae* EBY100 were stained with FITC-labeled anti-Vbeta1 antibody and PE-labeled HLA-A*02/COL6A3-002 tetramer. The unmodified scTv R4P3F9 (left panel, SEQ ID NO: 22) is compared to an scTv clone bearing single point mutations to stabilize the scTv scaffold (right panel), which was derived from the selection of a random mutation scTv library.

Peptide sequences of the invention
(positions are according to IMGT numbering: (François
Ehrenmann, Patrice Duroux, Chantal Ginestoux; Protein displays:
human (*Homo sapiens*) TRAV; IMGT Repertoire. IMGT ® the
international ImMunoGenetics information system ® w ww.imgt.org.;
Created: 16 Mar. 2011. Version: 3 Jun. 2016; François Ehrenmann,
Patrice Duroux, Chantal Ginestoux; Protein displays: human
(*Homo sapiens*) TRBV; IMGT Repertoire. IMGT ®, the international
ImMunoGenetics information system ® w ww.imgt.org.;
Created: 16 Mar. 2011. Version: 3 Jun. 2016.)

| SEQ ID NO: | Name | Description | Sequence |
|---|---|---|---|
| 1 | COL6A3-002 | | FLLDGSANV |
| 2 | R4P3F9 alpha | R4P3F9 TCR alpha chain-full length | MKSLRVLLVILWLQLSWVWSQQKEVEQNSGPLSVPEGAIA SLNCTYSDRGSQSFFWYRQYSGKSPELIMFIYSNGDKEDG RFTAQLNKASQYVSLLIRDSQPSDSATYLCAAYSGAGSYQ LTFGKGTKLSVIPNIQNPDPAVYQLRDSKSSDKSVCLFTD FDSQTNVSQSKDSDVYITDKTVLDMRSMDFKSNSAVAWSN KSDFACANAFNNSIIPEDTFFPSPESSCDVKLVEKSFETD TNLNFQNLSVIGFRILLLKVAGFNLLMTLRLWSS |
| 3 | R4P3F9 alpha leader | R4P3F9 TCR alpha chain-leader peptide | MKSLRVLLVILWLQLSWVWSQ |
| 4 | R4P3F9 alpha variable | R4P3F9 TCR alpha chain-variable domain | QKEVEQNSGPLSVPEGAIASLNCTYSDRGSQSFFWYRQYS GKSPELIMFIYSNGDKEDGRFTAQLNKASQYVSLLIRDSQ PSDSATYLCAAYSGAGSYQLTFGKGTKLSVIP |
| 5 | R4P3F9 CDRa1 | R4P3F9 TCR alpha chain-CDR1 | DRGSQS |

TABLE 1-continued

Peptide sequences of the invention
(positions are according to IMGT numbering: (François
Ehrenmann, Patrice Duroux, Chantal Ginestoux; Protein displays:
human (Homo sapiens) TRAV; IMGT Repertoire. IMGT ® the
international ImMunoGenetics information system ® w ww.imgt.org.;
Created: 16 Mar. 2011. Version: 3 Jun. 2016; François Ehrenmann,
Patrice Duroux, Chantal Ginestoux; Protein displays: human
(Homo sapiens) TRBV; IMGT Repertoire. IMGT ®, the international
ImMunoGenetics information system ® w ww.imgt.org.;
Created: 16 Mar. 2011. Version: 3 Jun. 2016.)

| SEQ ID NO: | Name | Description | Sequence |
|---|---|---|---|
| 6 | R4P3F9 CDRa2 | R4P3F9 TCR alpha chain-CDR2 | IYSNGD |
| 7 | R4P3F9 CDRa3 | R4P3F9 TCR alpha chain-CDR3 | CAAYSGAGSYQLT |
| 8 | R4P3F9-alpha constant | R4P3F9 TCR alpha chain-constant domain | NIQNPDPAVYQLRDSKSSDKSVCLFTDFDSQTNVSQSKDS DVYITDKTVLDMRSMDFKSNSAVAWSNKSDFACANAFNNS IIPEDTFFPSPESSCDVKLVEKSFETDTNLNFQNLSVIGF RILLLKVAGFNLLMTLRLWSS |
| 9 | R4P3F9-alpha constant start | R4P3F9 TCR alpha chain-constant domain start | NIQN |
| 10 | R4P3F9 beta | R4P3F9 TCR beta chain-full length | MGFRLLCCVAFCLLGAGPVDSGVTQTPKHLITATGQRVTL RCSPRSGDLSVYWYQQSLDQGLQFLIQYYNGEERAKGNIL ERFSAQQFPDLHSELNLSSLELGDSALYFCASSVESSYGY TFGSGTRLTVVEDLNKVFPPEVAVFEPSEAEISHTQKATL VCLATGFFPDHVELSWWVNGKEVHSGVSTDPQPLKEQPAL NDSRYCLSSRLRVSATFWQNPRNHFRCQVQFYGLSENDEW TQDRAKPVTQIVSAEAWGRADCGFTSVSYQQGVLSATILY EILLGKATLYAVLVSALVLMAMVKRKDF |
| 11 | R4P3F9 beta leader | R4P3F9 TCR beta chain-leader peptide | MGFRLLCCVAFCLLGAGPV |
| 12 | R4P3F9 beta variable | R4P3F9 TCR beta chain-variable domain | DSGVTQTPKHLITATGQRVTLRCSPRSGDLSVYWYQQSLD QGLQFLIQYYNGEERAKGNILERFSAQQFPDLHSELNLSS LELGDSALYFCASSVESSYGYTFGSGTRLTVV |
| 13 | R4P3F9 CDRb1 | R4P3F9 TCR beta chain-CDR1 | RSGDLS |
| 14 | R4P3F9 CDRb2 | R4P3F9 TCR beta chain-CDR2 | YYNGEE |
| 15 | R4P3F9 CDRb3 | R4P3F9 TCR beta chain-CDR3 | CASSVESSYGYT |
| 16 | R4P3F9 beta constant | R4P3F9 TCR beta chain-constant domain | EDLNKVFPPEVAVFEPSEAEISHTQKATLVCLATGFFPDH VELSWWVNGKEVHSGVSTDPQPLKEQPALNDSRYCLSSRL RVSATFWQNPRNHFRCQVQFYGLSENDEWTQDRAKPVTQI VSAEAWGRADCGFTSVSYQQGVLSATILYEILLGKATLYA VLVSALVLMAMVKRKDF |

TABLE 1-continued

Peptide sequences of the invention
(positions are according to IMGT numbering: (François Ehrenmann, Patrice Duroux, Chantal Ginestoux; Protein displays: human (Homo sapiens) TRAV; IMGT Repertoire. IMGT ® the international ImMunoGenetics information system ® w ww.imgt.org.; Created: 16 Mar. 2011. Version: 3 Jun. 2016; François Ehrenmann, Patrice Duroux, Chantal Ginestoux; Protein displays: human (Homo sapiens) TRBV; IMGT Repertoire. IMGT ®, the international ImMunoGenetics information system ® w ww.imgt.org.; Created: 16 Mar. 2011. Version: 3 Jun. 2016.)

| SEQ ID NO: | Name | Description | Sequence |
|---|---|---|---|
| 17 | R4P3F9 beta constant start 1 | R4P3F9 TCR beta chain-constant domain start 1 | EDLNK |
| 18 | R4P3F9 beta constant start 2 | R4P3F9 TCR beta chain-constant domain start 2 | EDLKN |
| 19 | Aga2p-R4P3F9 | Aga2p fusion protein with scTv R4P3F9 and tags | MQLLRCFSIFSVIASVLAQELTTICEQIPSPTLESTPYSLSTTTILANGKAMQGVFEYYKSVTFVSNCGSHPSTTSKGSPINTQYVFGGGGSDYKDDDDKGGGASQKEVEQNSGPLSVPEGAIASLNCTYSDRGSQSFFWYRQYSGKSPELIMSIYSNGDKEDGRFTAQLNKASQYVSLLIRDSQPSDSATYLCAAYSGAGSYQLTFGKGTKLSVIPNIQNGGGGSGGGGSGGGGSGGGGSGVTQTPKHLITATGQRVTLRCSPRSGDLSVYWYQQSLDQGLQFLIQYYNGEERAKGNILERFSAQQFPDLHSELNLSSLELGDSALYFCASSVESSYGYTFGSGTRLTVVEDLNKAAAGGSGGEQKLISEEDL |
| 20 | Aga2p | Leader sequence and Aga2p | MQLLRCFSIFSVIASVLAQELTTICEQIPSPTLESTPYSLSTTTILANGKAMQGVFEYYKSVTFVSNCGSHPSTTSKGSPINTQYVF |
| 21 | FLAG tag | FLAG tag plus linkers | GGGGSDYKDDDDKGGGAS |
| 22 | scTv R4P3F9 | Single chain variable domains of R4P3F9 with linker; aF55S in alpha variable domain | QKEVEQNSGPLSVPEGAIASLNCTYSDRGSQSFFWYRQYSGKSPELIMSIYSNGDKEDGRFTAQLNKASQYVSLLIRDSQPSDSATYLCAAYSGAGSYQLTFGKGTKLSVIPNIQNGGGGSGGGGSGGGGSGGGGSGVTQTPKHLITATGQRVTLRCSPRSGDLSVYWYQQSLDQGLQFLIQYYNGEERAKGNILERFSAQQFPDLHSELNLSSLELGDSALYFCASSVESSYGYTFGSGTRLTVVEDLNK |
| 23 | Myc tag | Linker and Myc tag | AAAGGSGGEQKLISEEDL |
| 24 | scTv R4P3F9-bQ43K | scTv R4P3F9 with stabilizing mutation bQ43K in beta variable domain | QKEVEQNSGPLSVPEGAIASLNCTYSDRGSQSFFWYRQYSGKSPELIMSIYSNGDKEDGRFTAQLNKASQYVSLLIRDSQPSDSATYLCAAYSGAGSYQLTFGKGTKLSVIPNIQNGGGGSGGGGSGGGGSGGGGSGVTQTPKHLITATGQRVTLRCSPRSGDLSVYWYKQSLDQGLQFLIQYYNGEERAKGNILERFSAQQFPDLHSELNLSSLELGDSALYFCASSVESSYGYTFGSGTRLTVVEDLNK |
| 25 | scTv R4P3F9-bL72S | scTv R4P3F9 with stabilizing mutation bL72S in beta variable domain | QKEVEQNSGPLSVPEGAIASLNCTYSDRGSQSFFWYRQYSGKSPELIMSIYSNGDKEDGRFTAQLNKASQYVSLLIRDSQPSDSATYLCAAYSGAGSYQLTFGKGTKLSVIPNIQNGGGGSGGGGSGGGGSGGGGSGVTQTPKHLITATGQRVTLRCSPRSGDLSVYWYQQSLDQGLQFLIQYYNGEERAKGNISERFSAQQFPDLHSELNLSSLELGDSALYFCASSVESSYGYTFGSGTRLTVVEDLNK |

TABLE 1-continued

Peptide sequences of the invention
(positions are according to IMGT numbering: (François Ehrenmann, Patrice Duroux, Chantal Ginestoux; Protein displays: human (Homo sapiens) TRAV; IMGT Repertoire. IMGT ® the international ImMunoGenetics information system ® www.imgt.org.; Created: 16 Mar. 2011. Version: 3 Jun. 2016; François Ehrenmann, Patrice Duroux, Chantal Ginestoux; Protein displays: human (Homo sapiens) TRBV; IMGT Repertoire. IMGT ®, the international ImMunoGenetics information system ® www.imgt.org.; Created: 16 Mar. 2011. Version: 3 Jun. 2016.)

| SEQ ID NO: | Name | Description | Sequence |
|---|---|---|---|
| 26 | CDRa1 mutant1 | aG29R mutation | DRRSQS |
| 27 | scTv R4P3F9S | Stabilized version of scTv R4P3F9 | QKEVEQNSGPLSVPEGAIASLNCTYSDRRSQSFFWYRQYSGKSPELIMSIYSNGDKEDGRFTAQLNKASQYVSLLIRDSQPSDSATYLCAAYSGAGSYQLTFGKGTKLSVIPGGGGSGGGGSGGGGSGGGGSGGGGSGVTQTPKHLITATGQRVTLRCSPRSGDLSVYWYKQSLDQGLQFLIQYYNGEERAKGNISERFSAQQFPDLHSELNLSSLELGDSALYFCASSVESSYGYTFGSGTRLTVV |
| 28 | AGRN-001 | Similar peptides | ALLDGRVQL |
| 29 | CLASP1-001 | Similar peptides | RLLDGAFKL |
| 30 | COL6A1-001 | Similar peptides | ILLDGSASV |
| 31 | COL6A2-001 | Similar peptides | FLLDGSERL |
| 32 | COL6A3-006 | Similar peptides | FLFDGSANLV |
| 33 | COL6A3-008 | Similar peptides | FLFDGSANL |
| 34 | COL6A3-014 | Similar peptides | FLLDGSEGV |
| 35 | VWA2-001 | Similar peptides | FLLDGSNSV |
| 36 | VWF-001 | Similar peptides | FLLDGSSRL |
| 37 | CDRb1 mutant 1 | Beta chain-CDR1 variant 1 | ARWHNN |
| 38 | CDRb1 mutant 2 | Beta chain-CDR1 variant 2 | AKDHLN |
| 39 | CDRb1 mutant 3 | Beta chain-CDR1 variant 3 | ARWHRN |
| 40 | CDRb1 mutant 4 | Beta chain-CDR1 variant 4 | AMDHPY |
| 41 | CDRb1 mutant 5 | Beta chain-CDR1 variant 5 | ATDHYN |
| 42 | CDRb1 mutant 6 | Beta chain-CDR1 variant 6 | ARYHTN |

TABLE 1-continued

Peptide sequences of the invention
(positions are according to IMGT numbering: (François Ehrenmann, Patrice Duroux, Chantal Ginestoux; Protein displays: human (*Homo sapiens*) TRAV; IMGT Repertoire. IMGT ® the international ImMunoGenetics information system ® w ww.imgt.org.; Created: 16 Mar. 2011. Version: 3 Jun. 2016; François Ehrenmann, Patrice Duroux, Chantal Ginestoux; Protein displays: human (*Homo sapiens*) TRBV; IMGT Repertoire. IMGT ®, the international ImMunoGenetics information system ® w ww.imgt.org.; Created: 16 Mar. 2011. Version: 3 Jun. 2016.)

| SEQ ID NO: | Name | Description | Sequence |
|---|---|---|---|
| 43 | CDRb1 mutant 7 | Beta chain-CDR1 variant 7 | APYHLN |
| 44 | CDRb1 mutant 8 | Beta chain-CDR1 variant 8 | AKDHTN |
| 45 | CDRb1 mutant 9 | Beta chain-CDR1 variant 9 | ARYHRN |
| 46 | CDRb1 mutant 10 | Beta chain-CDR1 variant 10 | ARWHSN |
| 47 | CDRb1 mutant 11 | Beta chain-CDR1 variant 11 | ATDHYN |
| 48 | CDRb1 mutant 12 | Beta chain-CDR1 variant 12 | RWGDLN |
| 49 | CDRb1 mutant 13 | Beta chain-CDR1 variant 13 | ARDHLN |
| 50 | 75-1 | Fab heavy chain with stabilized scTv R4P3F9S | MKWVTFISLLFLFSSAYSEVQLVESGGGLVQPGGSLRLSC AASGYSFTGYTMNWVRQAPGKGLEWVALINPYKGVSTYNQ KFKDRFTISVDKSKNTAYLQMNSLRAEDTAVYYCARSGYY GDSDWYFDVWGQGTLVTVSSASTKGPSVFPLAPSSKSTSG GTAALGCLVKDYFPEPVTVSWNSGALTSGVHTFPAVLQSS GLYSLSSVVTVPSSSLGTQTYICNVNHKPSNTKVDKKVEP KSCDKTHTSPPSPAPPVAGQKEVEQNSGPLSVPEGAIASL NCTYSDRGSQSFFWYRQYSGKSPELIMSIYSNGDKEDGRF TAQLNKASQYVSLLIRDSQPSDSATYLCAAYSGAGSYQLT FGKGTKLSVIPNIQNGGGGSGGGGSGGGGSGGGGSGGGGS GVTQTPKHLITATGQRVTLRCSPRSGDLSVYWYKQSLDQG LQFLIQYYNGEERAKGNISERFSAQQFPDLHSELNLSSLE LGDSALYFCASSVESSYGYTFGSGTRLTVVEDLKN |
| 51 | 75-Fab heavy chain | Fab heavy chain | MKWVTFISLLFLFSSAYSEVQLVESGGGLVQPGGSLRLSC AASGYSFTGYTMNWVRQAPGKGLEWVALINPYKGVSTYNQ KFKDRFTISVDKSKNTAYLQMNSLRAEDTAVYYCARSGYY GDSDWYFDVWGQGTLVTVSSASTKGPSVFPLAPSSKSTSG GTAALGCLVKDYFPEPVTVSWNSGALTSGVHTFPAVLQSS GLYSLSSVVTVPSSSLGTQTYICNVNHKPSNTKVDKKVEP KSCDKTHTSPPSPAPPVAG |
| 52 | 75-Fab light chain | Fab light chain | MKWVTFISLLFLFSSAYSDIQMTQSPSSLSASVGDRVTIT CRASQDIRNYLNWYQQKPGKAPKLLIYYTSRLESGVPSRF SGSGSGTDYTLTISSLQPEDFATYYCQQGNTLPWTFGQGT KVEIKRTVAAPSVFIFPPSDEQLKSGTASVVCLLNNFYPR EAKVQWKVDNALQSGNSQESVTEQDSKDSTYSLSSTLTLS KADYEKHKVYACEVTHQGLSSPVTKSFNRGEC |
| 53 | 1G4 alpha | 1G4 TCR alpha chain-full length | METLLGLLILWLQLQWVSSKQEVTQIPAALSVPEGENLVL NCSFTDSAIYNLQWFRQDPGKGLTSLLLIQSSQREQTSGR LNASLDKSSGRSTLYIAASQPGDSATYLCAVRPTSGGSYI PTFGRGTSLIVHPYIQNPDPAVYQLRDSKSSDKSVCLFTD FDSQTNVSQSKDSDVYITDKTVLDMRSMDFKSNSAVAWSN KSDFACANAFNNSIIPEDTFFPSPESSCDVKLVEKSFETD TNLNFQNLSVIGFRILLLKVAGFNLLMTLRLWSS |

TABLE 1-continued

Peptide sequences of the invention
(positions are according to IMGT numbering: (François Ehrenmann, Patrice Duroux, Chantal Ginestoux; Protein displays: human (Homo sapiens) TRAV; IMGT Repertoire. IMGT ® the international ImMunoGenetics information system ® www.imgt.org.; Created: 16 Mar. 2011. Version: 3 Jun. 2016; François Ehrenmann, Patrice Duroux, Chantal Ginestoux; Protein displays: human (Homo sapiens) TRBV; IMGT Repertoire. IMGT ®, the international ImMunoGenetics information system ® www.imgt.org.; Created: 16 Mar. 2011. Version: 3 Jun. 2016.)

| SEQ ID NO: | Name | Description | Sequence |
|---|---|---|---|
| 54 | 1G4 alpha leader | 1G4 TCR alpha chain-leader peptide | METLLGLLILWLQLQWVSSK |
| 55 | 1G4 alpha variable | 1G4 TCR alpha chain-variable domain | QEVTQIPAALSVPEGENLVLNCSFTDSAIYNLQWFRQDPG KGLTSLLLIQSSQREQTSGRLNASLDKSSGRSTLYIAASQ PGDSATYLCAVRPTSGGSYIPTFGRGTSLIVHP |
| 56 | 1G4 alpha constant | 1G4 TCR alpha chain-constant domain | YIQNPDPAVYQLRDSKSSDKSVCLFTDFDSQTNVSQSKDS DVYITDKTVLDMRSMDFKSNSAVAWSNKSDFACANAFNNS IIPEDTFFPSPESSCDVKLVEKSFETDTNLNFQNLSVIGF RILLLKVAGFNLLMTLRLWSS |
| 57 | 1G4 beta | 1G4 TCR beta chain-full length | MSIGLLCCAALSLLWAGPVNAGVTQTPKFQVLKTGQSMTL QCAQDMNHEYMSWYRQDPGMGLRLIHYSVGAGITDQGEVP NGYNVSRSTTEDFPLRLLSAAPSQTSVYFCASSYVGNTGE LFFGEGSRLTVLEDLKNVFPPEVAVFEPSEAEISHTQKAT LVCLATGFYPDHVELSWWVNGKEVHSGVSTDPQPLKEQPA LNDSRYCLSSRLRVSATFWQNPRNHFRCQVQFYGLSENDE WTQDRAKPVTQIVSAEAWGRADCGFTSESYQQGVLSATIL YEILLGKATLYAVLVSALVLMAMVKRKDSRG |
| 58 | 1G4 beta leader | 1G4 TCR beta chain-leader peptide | MSIGLLCCAALSLLWAGPVNA |
| 59 | 1G4 beta variable | 1G4 TCR beta chain-variable domain | GVTQTPKFQVLKTGQSMTLQCAQDMNHEYMSWYRQDPGMG LRLIHYSVGAGITDQGEVPNGYNVSRSTTEDFPLRLLSAA PSQTSVYFCASSYVGNTGELFFGEGSRLTVL |
| 60 | 1G4 beta constant | Beta chain-constant domain | EDLKNVFPPEVAVFEPSEAEISHTQKATLVCLATGFYPDH VELSWWVNGKEVHSGVSTDPQPLKEQPALNDSRYCLSSRL RVSATFWQNPRNHFRCQVQFYGLSENDEWTQDRAKPVTQI VSAEAWGRADCGFTSESYQQGVLSATILYEILLGKATLYA VLVSALVLMAMVKRKDSRG |
| 61 | NYESO1-001 | Control peptide | SLLMWITQV |
| 62 | C-14 beta; C-5 beta | C-14; C-5 TCR full length beta chain with CDRb1 mutant 4 | MGFRLLCCVAFCLLGAGPVDSGVTQTPKHLITATGQRVTL RCSPAMDHPYVYWYQQSLDQGLQFLIQYYNGEERAKGNIL ERFSAQQFPDLHSELNLSSLELGDSALYFCASSVESSYGY TFGSGTRLTVVEDLNKVFPPEVAVFEPSEAEISHTQKATL VCLATGFFPDHVELSWWVNGKEVHSGVSTDPQPLKEQPAL NDSRYCLSSRLRVSATFWQNPRNHFRCQVQFYGLSENDEW TQDRAKPVTQIVSAEAWGRADCGFTSVSYQQGVLSATILY EILLGKATLYAVLVSALVLMAMVKRKDF |
| 63 | C-14 alpha | C-14 TCR full length alpha chain with CDRa1 mutant 1 | MKSLRVLLVILWLQLSWVWSQQKEVEQNSGPLSVPEGAIA SLNCTYSDRRSQSFFWYRQYSGKSPELIMFIYSNGDKEDG RFTAQLNKASQYVSLLIRDSQPSDSATYLCAAYSGAGSYQ LTFGKGTKLSVIPNIQNPDPAVYQLRDSKSSDKSVCLFTD FDSQTNVSQSKDSDVYITDKTVLDMRSMDFKSNSAVAWSN KSDFACANAFNNSIIPEDTFFPSPESSCDVKLVEKSFETD TNLNFQNLSVIGFRILLLKVAGFNLLMTLRLWSS |

TABLE 1-continued

Peptide sequences of the invention
(positions are according to IMGT numbering: (François
Ehrenmann, Patrice Duroux, Chantal Ginestoux; Protein displays:
human (Homo sapiens) TRAV; IMGT Repertoire. IMGT ® the
international ImMunoGenetics information system ® w ww.imgt.org.;
Created: 16 Mar. 2011. Version: 3 Jun. 2016; François Ehrenmann,
Patrice Duroux, Chantal Ginestoux; Protein displays: human
(Homo sapiens) TRBV; IMGT Repertoire. IMGT ®, the international
ImMunoGenetics information system ® w ww.imgt.org.;
Created: 16 Mar. 2011. Version: 3 Jun. 2016.)

| SEQ ID NO: | Name | Description | Sequence |
|---|---|---|---|
| 64 | 75-5 | Fab heavy chain with stabilized scTv R4P3F9S and CDRb1 mutant 4 | MKWVTFISLLFLFSSAYSEVQLVESGGGLVQPGGSLRLSC AASGYSFTGYTMNWVRQAPGKGLEWVALINPYKGVSTYNQ KFKDRFTISVDKSKNTAYLQMNSLRAEDTAVYYCARSGYY GDSDWYFDVWGQGTLVTVSSASTKGPSVFPLAPSSKSTSG GTAALGCLVKDYFPEPVTVSWNSGALTSGVHTFPAVLQSS GLYSLSSVVTVPSSSLGTQTYICNVNHKPSNTKVDKKVEP KSCDKTHTSPPSPAPPVAGQKEVEQNSGPLSVPEGAIASL NCTYSDRGSQSFFWYRQYSGKSPELIMSIYSNGDKEDGRF TAQLNKASQYVSLLIRDSQPSDSATYLCAAYSGAGSYQLT FGKGTKLSVIPNIQNGGGGSGGGGSGGGGSGGGGSGGGGS GVTQTPKHLITATGQRVTLRCSPAMDHPYVYWYKQSLDQG LQFLIQYYNGEERAKGNISERFSAQQFPDLHSELNLSSLE LGDSALYFCASSVESSYGYTFGSGTRLTVVEDLKN |
| 65 | 75-14 | Fab heavy chain with stabilized scTv R4P3F9S, CDRa1 mutant 1 and CDRb1 mutant 4 | MKWVTFISLLFLFSSAYSEVQLVESGGGLVQPGGSLRLSC AASGYSFTGYTMNWVRQAPGKGLEWVALINPYKGVSTYNQ KFKDRFTISVDKSKNTAYLQMNSLRAEDTAVYYCARSGYY GDSDWYFDVWGQGTLVTVSSASTKGPSVFPLAPSSKSTSG GTAALGCLVKDYFPEPVTVSWNSGALTSGVHTFPAVLQSS GLYSLSSVVTVPSSSLGTQTYICNVNHKPSNTKVDKKVEP KSCDKTHTSPPSPAPPVAGQKEVEQNSGPLSVPEGAIASL NCTYSDRRSQSFFWYRQYSGKSPELIMSIYSNGDKEDGRF TAQLNKASQYVSLLIRDSQPSDSATYLCAAYSGAGSYQLT FGKGTKLSVIPNIQNGGGGSGGGGSGGGGSGGGGSGGGGS GVTQTPKHLITATGQRVTLRCSPAMDHPYVYWYKQSLDQG LQFLIQYYNGEERAKGNISERFSAQQFPDLHSELNLSSLE LGDSALYFCASSVESSYGYTFGSGTRLTVVEDLKN |
| 66 | 75-25 | Fab heavy chain with stabilized scTv R4P3F9S in beta/alpha orientation, CDRa1 mutant 1 | MKWVTFISLLFLFSSAYSEVQLVESGGGLVQPGGSLRLSC AASGYSFTGYTMNWVRQAPGKGLEWVALINPYKGVSTYNQ KFKDRFTISVDKSKNTAYLQMNSLRAEDTAVYYCARSGYY GDSDWYFDVWGQGTLVTVSSASTKGPSVFPLAPSSKSTSG GTAALGCLVKDYFPEPVTVSWNSGALTSGVHTFPAVLQSS GLYSLSSVVTVPSSSLGTQTYICNVNHKPSNTKVDKKVEP KSCDKTHTSPPSPAPPVAGGVTQTPKHLITATGQRVTLRC SPRSGDLSVYWYKQSLDQGLQFLIQYYNGEERAKGNISER FSAQQFPDLHSELNLSSLELGDSALYFCASSVESSYGYTF GSGTRLTVVEDLKNGGGGSGGGGSGGGGSGGGGSGGGGSQ KEVEQNSGPLSVPEGAIASLNCTYSDRRSQSFFWYRQYSG KSPELIMSIYSNGDKEDGRFTAQLNKASQYVSLLIRDSQP SDSATYLCAAYSGAGSYQLTFGKGTKLSVIPNIQN |

EXAMPLES

Native T cell receptors (TCRs) against cancer antigens are often of lower affinity when compared to TCRs targeting viral antigens, and this may be one possible explanation for tumor immune escape (Aleksic et al. 2012). Therefore, it is desirable to have higher affinity TCR variants designed for the use as antigen recognizing constructs in an adoptive cell therapy, or as recognition module of a soluble approach, i.e., using bispecific molecules (Hickman et al. 2016). This invention thus relates to the modification and optimization of the naturally occurring T cell receptor R4P3F9 (SEQ ID NOs: 2 and 10) targeting the tumor associated peptide COL6A3-002 (SEQ ID NO: 1) with an affinity of about 60 μM (DE102016115246).

Example 1: Generation of Stable scTv

For the present invention, the previously investigated TCR R4P3F9 (SEQ ID NOs: 2 and 10) was converted into a single chain TCR construct (scTv, SEQ ID NO: 22) for maturation via yeast surface display by combination of the variable alpha (SEQ ID NO: 4) and beta (SEQ ID NO: 12) domain with appendages of the respective constant domains (SEQ ID NOs: 9 and 17) and an appropriate glycine-serine linker sequence. The DNA of the corresponding sequence was synthesized and transformed into Saccharomyces cerevisiae EB Y100 (MATa AGA1::GAL1AGA1::URA3 ura352 trp1 leu2delta200 his3delta200 pep4::HIS3 prbd1.6R can1 GAL) (ATCC® MYA 4941™) together with a yeast display vector containing a leader sequence and the Aga2p yeast mating protein (SEQ ID NO: 20), based on pCT302 (Boder et al. 2000). The resulting fusion protein after homologous recombination in the yeast (SEQ ID NO: 19) contains a leader peptide at the N-terminus of the Aga2p protein, responsible for the display of the protein of interest (Boder et al. 1997), short peptide tags including linker sequences (SEQ ID NOs: 21 and 23) for expression controls and the protein of interest, namely the scTv R4P3F9 (SEQ ID NO: 22) or its variants. The transformation was performed as described in DE102016121899 and resulted in up to $10^9$ yeast clones per library. The libraries were generated via a random mutation PCR approach spanning the whole gene sequence of the scTv R4P3F9.

The selection process for the yeast clones bearing the best expressing scTv that is selectively binding to COL6A3-002 in context of HLA-A*02 was essentially performed as described in Smith et al 2015. In order to ascertain high expression and correct conformation of the scTv R4P3F9 variant, displayed on the yeast surface, an anti-Vbeta1 (Beckman Coulter, clone BL37.2) antibody was used, together with HLA-A*02/COL6A3-002 tetramer (FIG. 1). The scTv conversion by yeast surface display revealed two crucial stabilizing mutations in the framework region together with the original CDR sequences for the proper presentation of the scTv on the cell surface, namely bQ43K (SEQ ID NO: 24) and bL72S (SEQ ID NO: 25), both located on the beta chain. Furthermore, during stability maturation position 29 in the CDR1 of the alpha chain (SEQ ID NO: 5) was converted from glycine to arginine (CDRa1 mutant 1, SEQ ID NO: 26), which resulted in improved tetramer binding.

Example 2: Affinity Maturation of Stabilized scTv

To generate scTv molecules with higher binding affinity towards HLA-A*02/COL6A3-002, the CDRb1 (SEQ ID NO: 13) was degenerated using the previously identified stabilized scTv R4P3F9S scaffold (SEQ ID NO: 27) expressing the stabilizing mutations aG29R, bQ43K and bL72S. The CDRb1 residues were randomized by using degenerate DNA oligo primers essentially as described previously (Smith et al. 2015). The resulting DNA library was transformed as described in example 1. To retain scTv binding selectivity, negative selection was employed against HLA-A*02 tetramers comprising peptides derived from normal tissues (SEQ ID NOs: 28 to 36), which show high sequence similarity to COL6A3-002 peptide.

Figure 2:
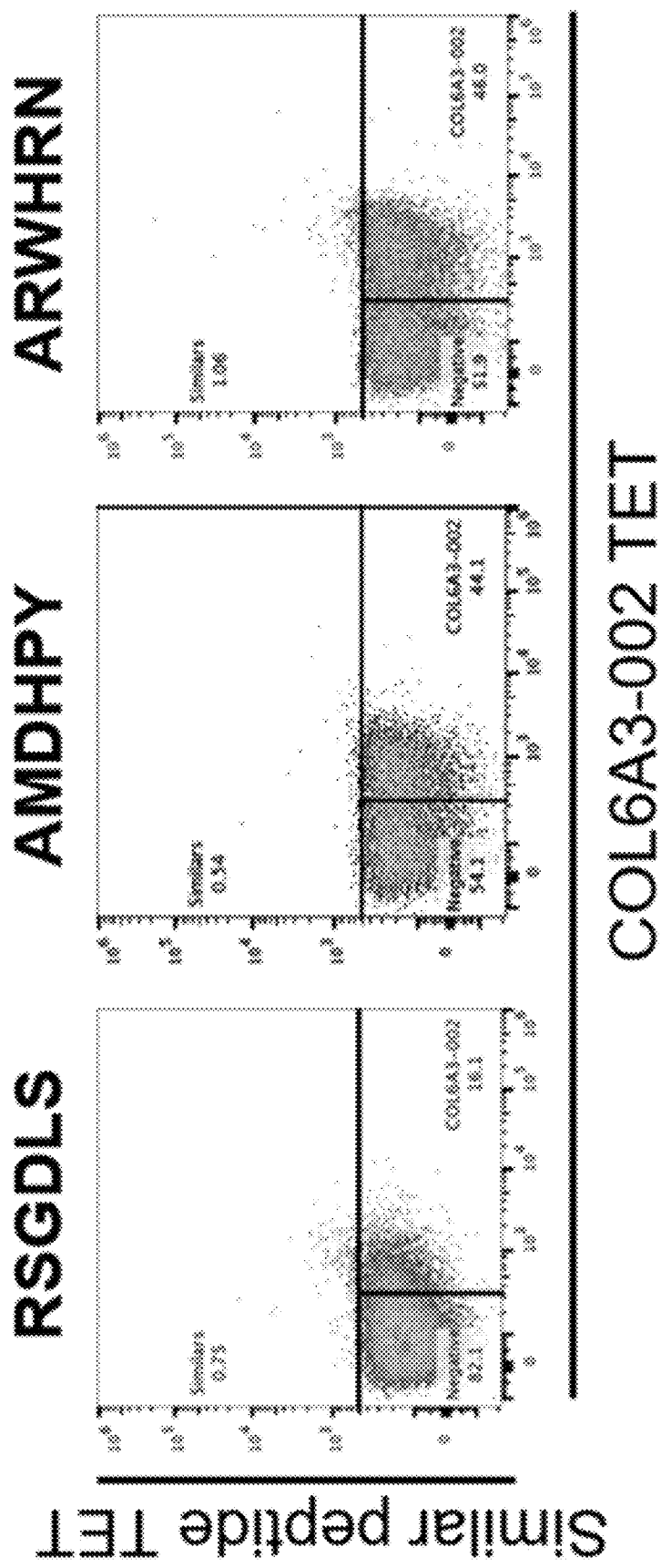
FIG. 2 shows scTv affinity maturation via yeast surface display. Stabilized scTv molecules with and without affinity maturated CDR1 beta were stained with HLA-A*02 tetramers containing COL6A3-002 (SEQ ID NO: 1) and counterstained with a mix of HLA-A*02 tetramers containing 9 peptides (SEQ ID NO: 28 to 36) with high sequence similarity to COL6A3-002. Stabilized scTv (SEQ ID NO 27) with non-maturated beta chain CDR1 sequence RSGDLS (SEQ ID NO: 13) is compared with scTv clones bearing the affinity maturated beta chain CDR1 sequences AMDHPY (SEQ ID NO: 40) and ARWHRN (SEQ ID NO: 39).

For the selection of affinity enhanced and selective scTv R4P3F9S variants a decreasing concentration of HLA-A*02/COL6A3-002 tetramer was used for each sorting round. After three selection rounds, single scTv clones were isolated and sequenced, resulting in a variety of affinity maturated CDRb1 sequences (SEQ ID NOs: 37 to 49). For scTv with maturated CDRb1 sequences a strong improvement in COL6A3-002 binding could be demonstrated while the selectivity of COL6A3-002 binding was retained as no binding of 9 similar peptides was observed (FIG. 2).

Example 3: Production of Bispecific Antibody-scTv Fusion Proteins

Figure 3:
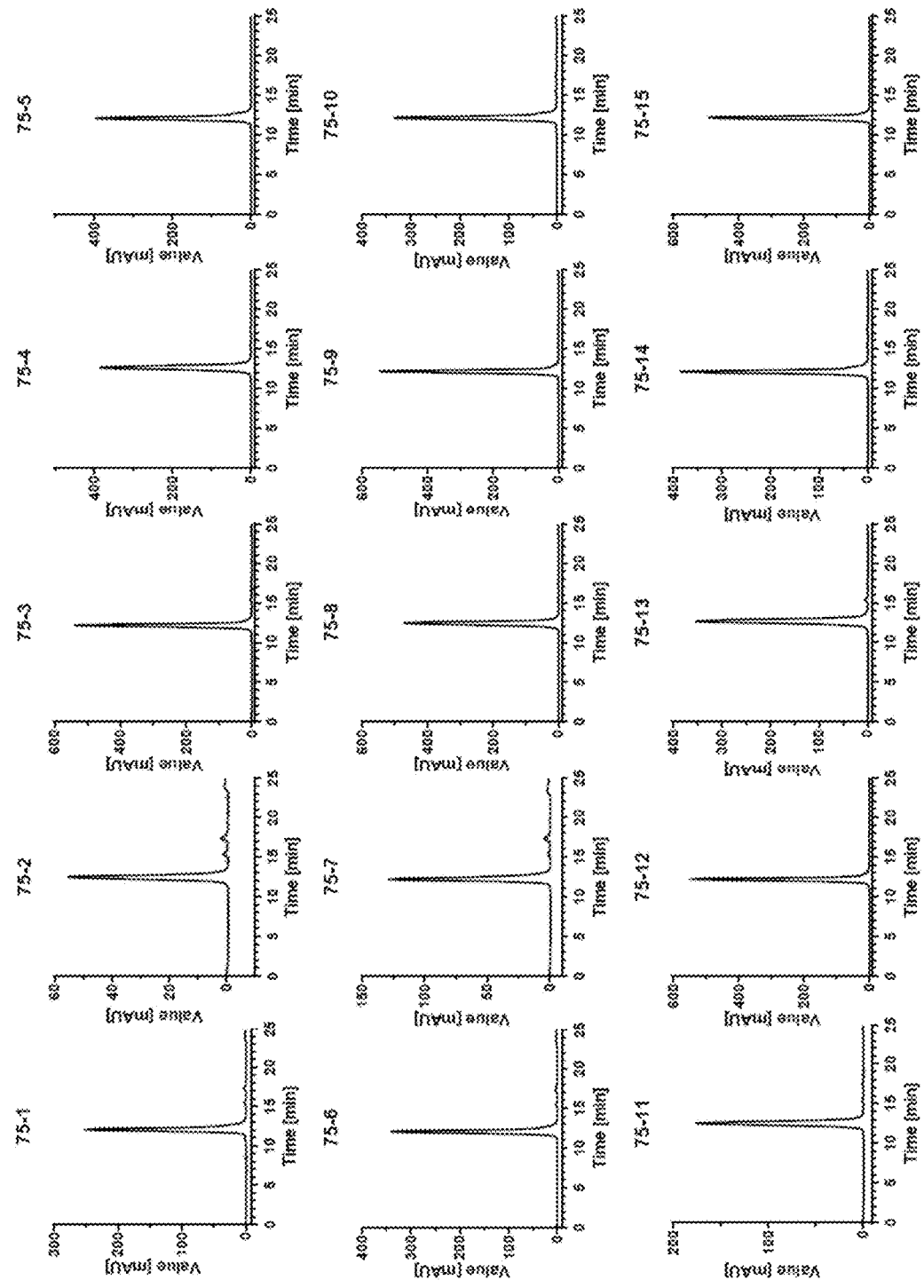
FIG. 3 shows size exclusion chromatography elution profiles of anti-CD3 Fab-scTv R4P3F9S fusion variants 75-1 to 75-25.
Figure 3:
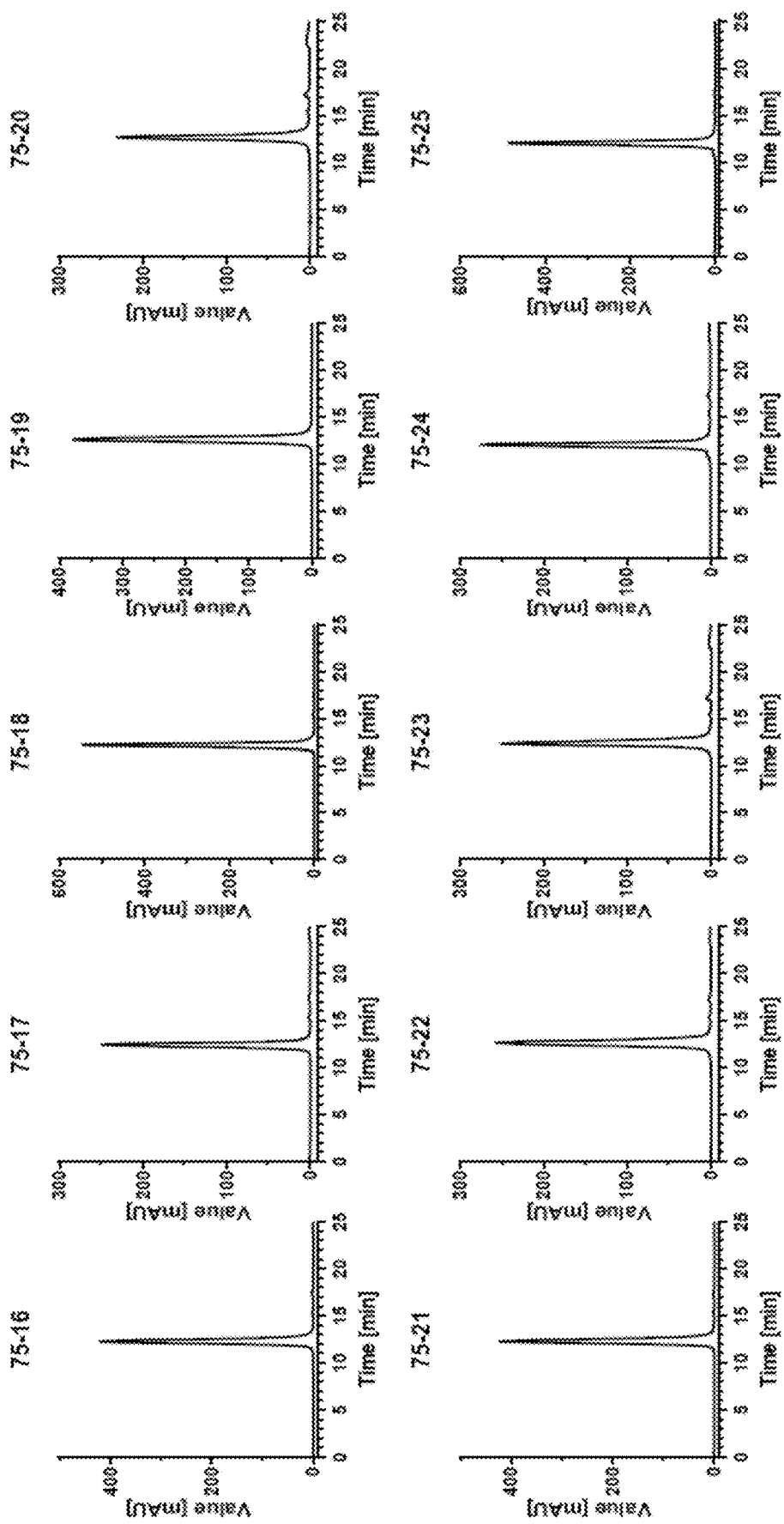

Stabilized and affinity maturated scTv against HLA-A*02/COL6A3-002 can be expressed in fusion with an antibody moiety directed against CD3 allowing tumor-specific retargeting and activation of T cells independent of their natural specificity. The inventors generated bispecific antibody-TCR fusion proteins comprising an anti-CD3 Fab (UCHT1) heavy chain (SEQ ID NO: 51) fused to scTv R4P3F9S variants (SEQ ID NOs: 50, 64, 65 and 66) and an anti-CD3 Fab (UCHT1) light chain (SEQ ID NO: 52). The resulting Fab-scTv fusion proteins have a molecular mass of approximately 75 kDa. Based on different CDR1 sequences of the scTv R4P3F9S alpha (SEQ ID NOs: 5 and 26) and beta chain (SEQ ID NOs: 13 and 37 to 49) different Fab-scTv fusion variants (75-1 to 75-25, Table 2) were expressed in transiently transfected ExpiCHO cells as recommended by the manufacturer. Proteins were purified by protein L and size exclusion chromatography. All fusion variants could be produced with yields ranging from 80 µg up to 1 mg (Table 2) and homogeneously formed heterodimers at the expected size as analyzed by size exclusion chromatography (FIG. 3).

TABLE 2

Nomenclature and yields of bispecific Fab-scTv fusion proteins. The molecules are based on SEQ ID NOs 50 and 52 and the indicated CDRa1 and CDRb1 variants.

| Variant | CDRa1/SEQ | CDRb1/SEQ | Yield [µg] |
|---|---|---|---|
| 75-1 | DRGSQS (SEQ ID NO. 5) | RSGDLS (SEQ ID NO. 13) | 267.9 |
| 75-2 | DRGSQS (SEQ ID NO. 5) | ARWHNN (SEQ ID NO. 37) | 78.4 |
| 75-3 | DRGSQS (SEQ ID NO. 5) | AKDHLN (SEQ ID NO. 38) | 646.7 |
| 75-4 | DRGSQS (SEQ ID NO. 5) | ARWHRN (SEQ ID NO. 39) | 704.3 |
| 75-5 | DRGSQS (SEQ ID NO. 5) | AMDHPY (SEQ ID NO. 40) | 397.2 |
| 75-6 | DRGSQS (SEQ ID NO. 5) | ATDHYN (SEQ ID NO. 41) | 268.1 |
| 75-7 | DRGSQS (SEQ ID NO. 5) | ARYHTN (SEQ ID NO. 42) | 83.2 |
| 75-8 | DRGSQS (SEQ ID NO. 5) | APYHLN (SEQ ID NO. 43) | 765.7 |
| 75-9 | DRGSQS (SEQ ID NO. 5) | AKDHTN (SEQ ID NO. 44) | 1067.2 |
| 75-10 | DRRSQS (SEQ ID NO. 26) | RSGDLS (SEQ ID NO. 13) | 389.6 |
| 75-11 | DRRSQS (SEQ ID NO. 26) | ARWHNN (SEQ ID NO. 37) | 270.4 |
| 75-12 | DRRSQS (SEQ ID NO. 26) | AKDHLN (SEQ ID NO. 38) | 943.6 |
| 75-13 | DRRSQS (SEQ ID NO. 26) | ARWHRN (SEQ ID NO. 39) | 560.3 |
| 75-14 | DRRSQS (SEQ ID NO. 26) | AMDHPY (SEQ ID NO. 40) | 360.7 |
| 75-15 | DRRSQS (SEQ ID NO. 26) | ATDHYN (SEQ ID NO. 41) | 541.5 |
| 75-16 | DRRSQS (SEQ ID NO. 26) | ARYHTN (SEQ ID NO. 42) | 403.6 |
| 75-17 | DRRSQS (SEQ ID NO. 26) | APYHLN (SEQ ID NO. 43) | 195.5 |
| 75-18 | DRRSQS (SEQ ID NO. 26) | AKDHTN (SEQ ID NO. 44) | 731.3 |
| 75-19 | DRRSQS (SEQ ID NO. 26) | ARYHRN (SEQ ID NO. 45) | 794 |

TABLE 2-continued

Nomenclature and yields of bispecific Fab-scTv fusion proteins. The molecules are based on SEQ ID NOs 50 and 52 and the indicated CDRa1 and CDRb1 variants.

| Variant | CDRa1/SEQ | CDRb1/SEQ | Yield [µg] |
|---|---|---|---|
| 75-20 | DRRSQS (SEQ ID NO. 26) | ARWHSN (SEQ ID NO. 46) | 85.5 |
| 75-21 | DRRSQS (SEQ ID NO. 26) | ATDHYN (SEQ ID NO. 47) | 276 |
| 75-22 | DRRSQS (SEQ ID NO. 26) | RWGDLN (SEQ ID NO. 48) | 255 |
| 75-23 | DRRSQS (SEQ ID NO. 26) | ARDHLN (SEQ ID NO. 49) | 217 |
| 75-24[a] | DRGSQS (SEQ ID NO: 5) | RSGDLS (SEQ ID NO. 13) | 166.6 |
| 75-25[a] | DRRSQS (SEQ ID NO. 26) | RSGDLS (SEQ ID NO. 13) | 267 |

[a]beta-alpha orientation of scTv

TABLE 3

Binding affinity of Fab-scTv fusion proteins to HLA-A*02/COL6A3-002.

| Variant | KD (M) | kon (1/Ms) | koff (1/s) |
|---|---|---|---|
| 75-1 | 8.06E−06 | 1.01E+05 | 8.17E−01 |
| 75-2 | 3.69E−06 | 1.59E+05 | 5.86E−01 |
| 75-3 | 4.92E−06 | 9.71E+04 | 4.78E−01 |
| 75-4 | 5.76E−06 | 9.78E+04 | 5.63E−01 |
| 75-5 | 4.32E−04 | 2.21E+03 | 9.55E−01 |
| 75-6 | 1.13E−06 | 2.06E+05 | 2.32E−01 |
| 75-7 | 1.79E−06 | 1.93E+05 | 3.44E−01 |
| 75-8 | 3.45E−06 | 1.36E+05 | 4.69E−01 |
| 75-9 | 1.41E−05 | 6.02E+04 | 8.51E−01 |
| 75-10 | 1.78E−06 | 1.69E+05 | 3.01E−01 |
| 75-11 | 2.82E−07 | 4.16E+05 | 1.18E−01 |
| 75-12 | 3.74E−07 | 2.67E+05 | 1.00E−01 |
| 75-13 | 4.05E−07 | 3.28E+05 | 1.33E−01 |
| 75-14 | 3.10E−06 | 8.41E+04 | 2.61E−01 |
| 75-15 | 7.78E−07 | 2.33E+05 | 1.81E−01 |
| 75-16 | 5.87E−07 | 3.37E+05 | 1.98E−01 |
| 75-17 | 2.27E−07 | 3.62E+05 | 8.20E−02 |
| 75-18 | 1.93E−06 | 1.51E+05 | 2.91E−01 |
| 75-19 | 6.00E−07 | 2.96E+05 | 1.78E−01 |
| 75-20 | 5.31E−07 | 6.08E+05 | 3.23E−01 |
| 75-21 | 5.52E−07 | 2.72E+05 | 1.50E−01 |
| 75-22 | 8.22E−07 | 2.48E+05 | 2.04E−01 |
| 75-23 | 3.24E−07 | 3.18E+05 | 1.03E−01 |
| 75-24 | 5.20E−06 | 1.08E+05 | 5.62E−01 |
| 75-25 | 8.33E−06 | 6.23E+04 | 5.19E−01 |

TABLE 4

Comparative binding affinity of Fab-scTv fusion proteins to HLA-A*02/COL6A3-002 and HLA-A*02/COL6A1-001.

| Variant | pHLA-A*02 | KD (M) | $KD_{COL6A1\text{-}001}/KD_{COL6A3\text{-}002}$ |
|---|---|---|---|
| 75-10 | COL6A3-002 | 1.37E−05 | 8 |
|  | COL6A1-001 | 1.08E−04 |  |
| 75-11 | COL6A3-002 | 8.50E−07 | 8 |
|  | COL6A1-001 | 6.46E−06 |  |
| 75-12 | COL6A3-002 | 7.24E−07 | 12 |
|  | COL6A1-001 | 8.98E−06 |  |
| 75-13 | COL6A3-002 | 7.39E−07 | 57 |
|  | COL6A1-001 | 4.23E−05 |  |
| 75-17 | COL6A3-002 | 8.25E−07 | 9 |
|  | COL6A1-001 | 7.10E−06 |  |
| 75-23 | COL6A3-002 | 1.15E−06 | 22 |
|  | COL6A1-001 | 2.55E−05 |  |

Example 4: Fab-scTv Fusion Protein Binding to COL6A3-002 and Similar Peptides

Figure 4:
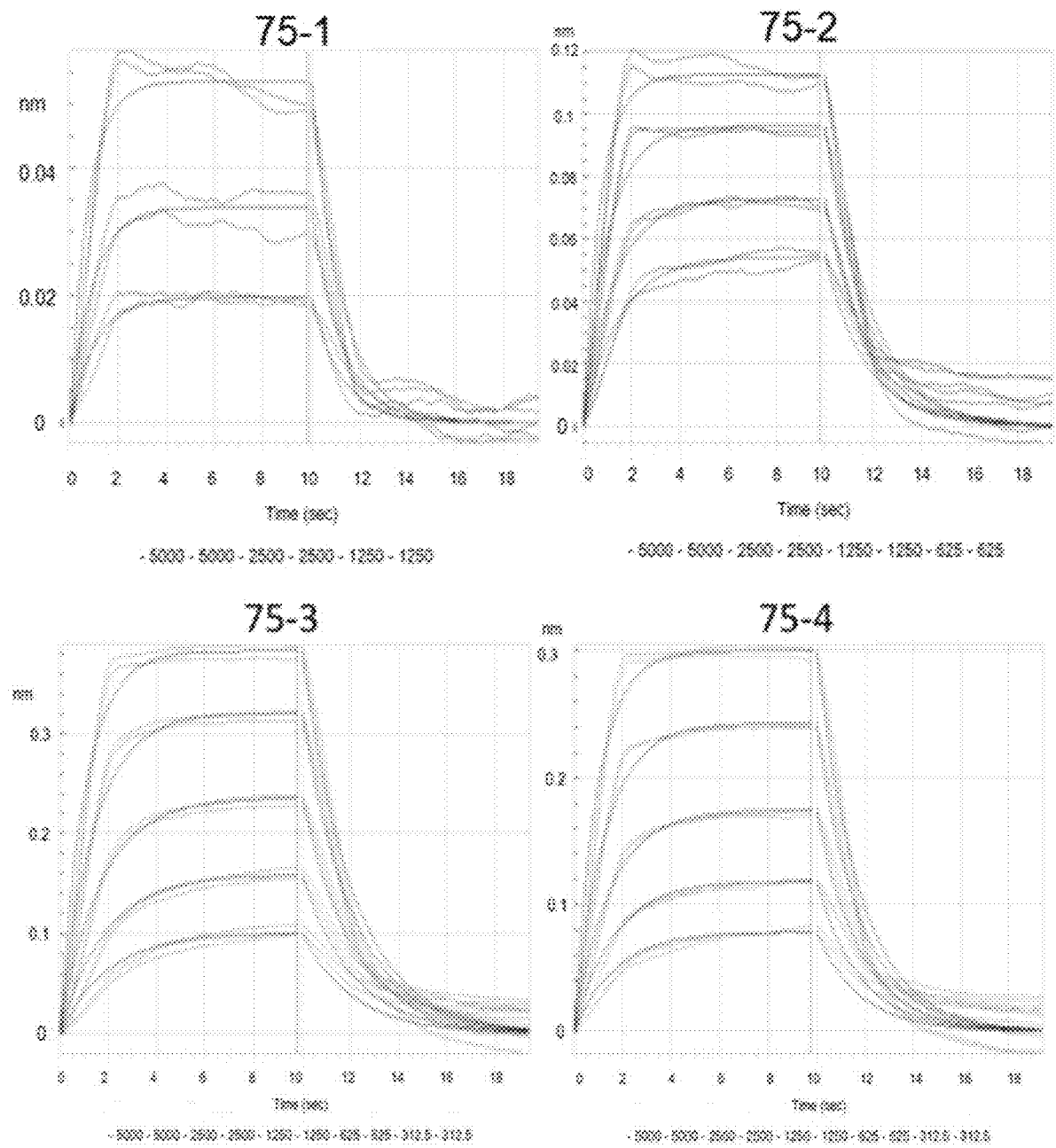
FIG. 4 shows the HLA-A*02/COL6A3-002 binding kinetics of anti-CD3 Fab-scTv R4P3F9S fusion variants 75-1 to 75-25 as measured by biolayer interferometry. Analyzed concentrations of HLA-A*02/COL6A3-002 are indicated.
Figure 4:
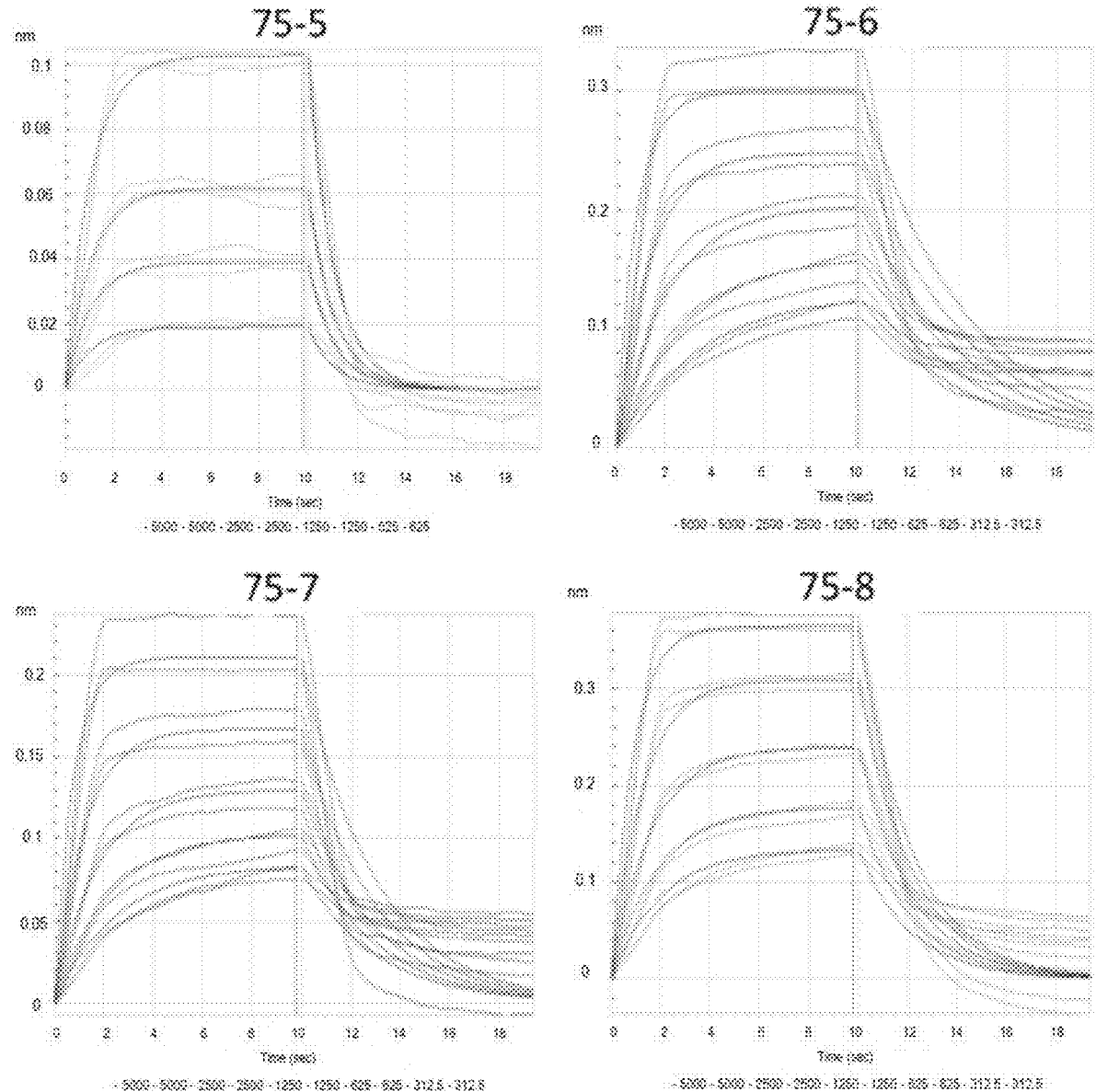
Figure 4:
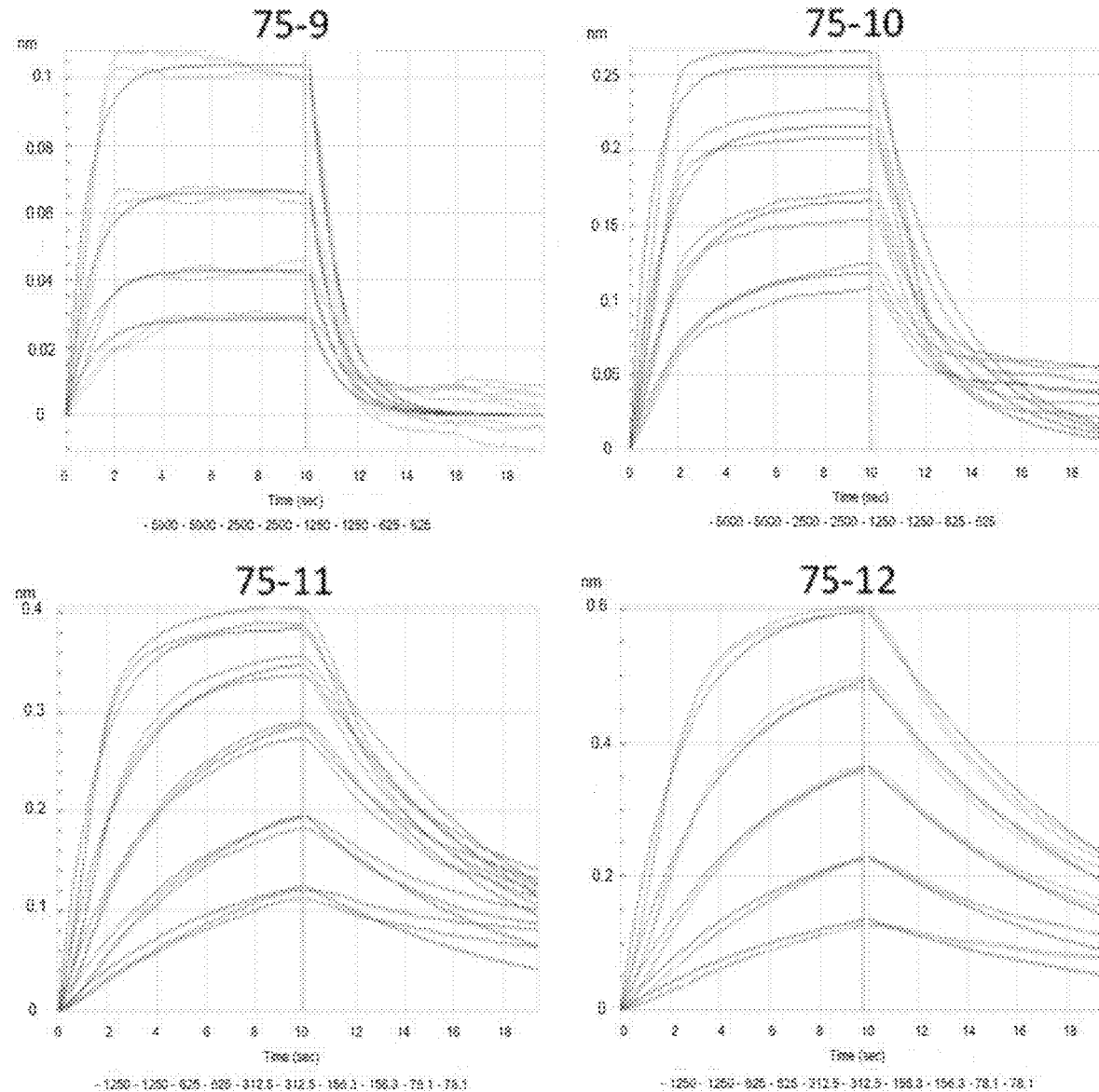
Figure 4:
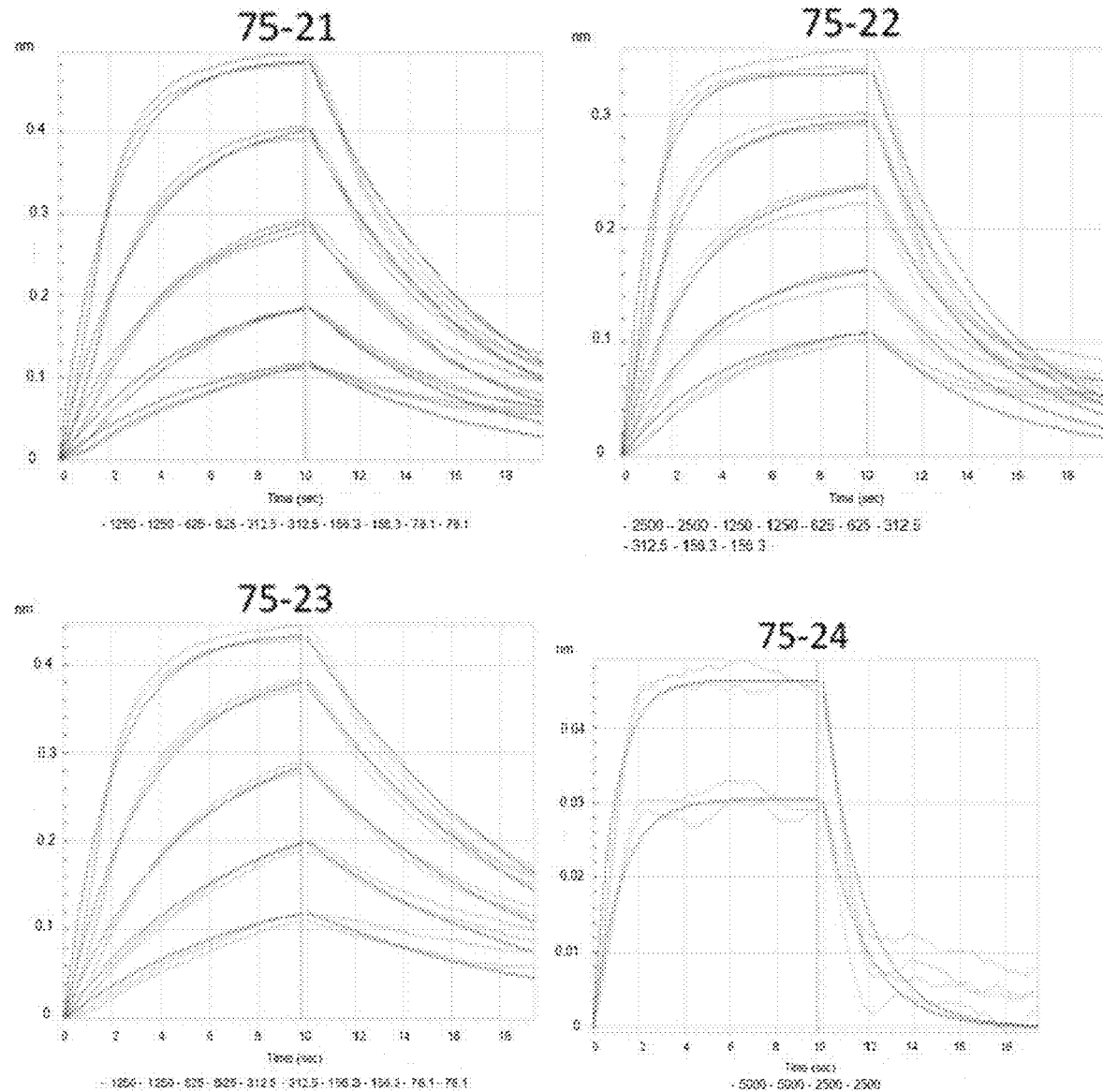
Figure 4:
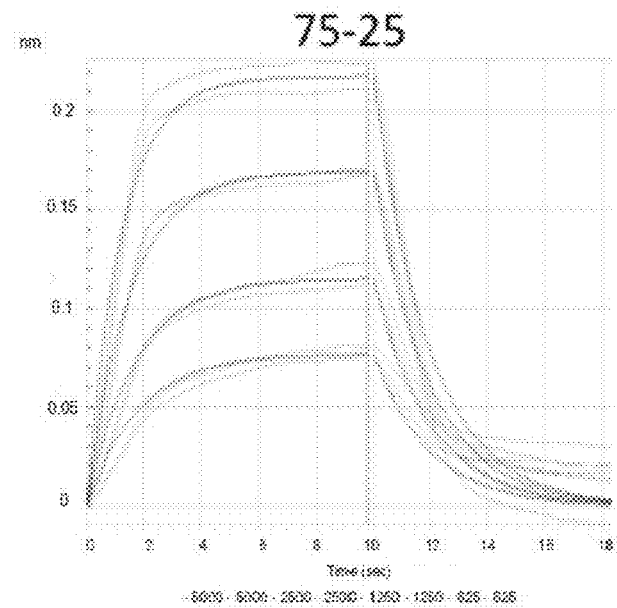
Figure 5:
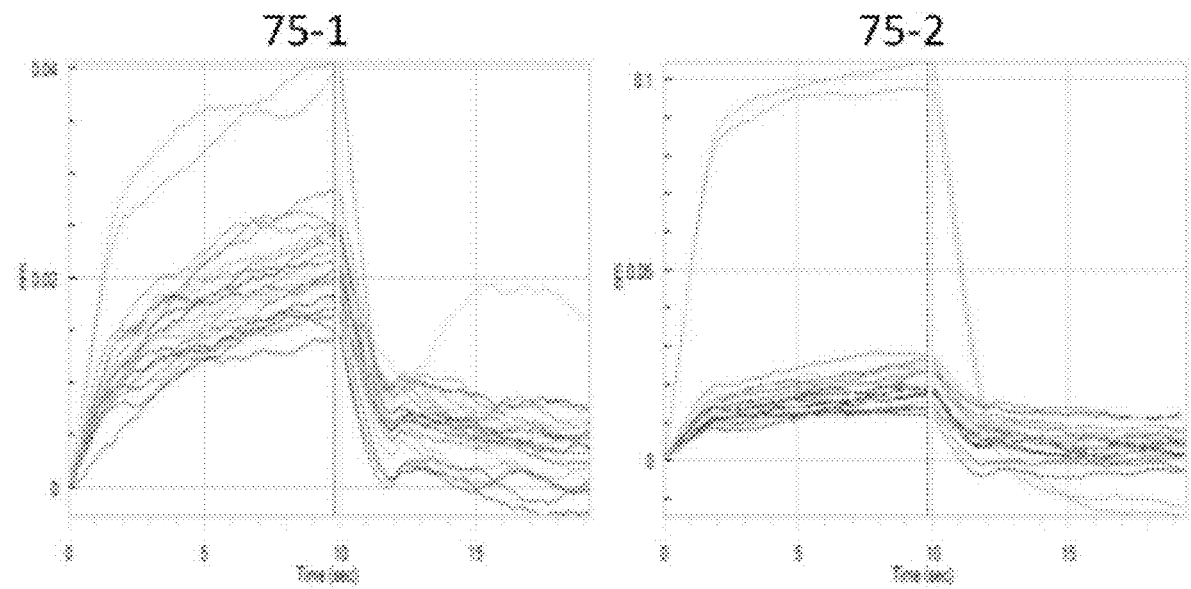
FIG. 5 shows binding analysis of anti-CD3 Fab-scTv R4P3F9S fusion variants 75-1 to 75-25 as measured via biolayer interferometry (BLI). 1 µM of HLA-A*02 in complex with the indicated similar peptides was analyzed.
Figure 5:
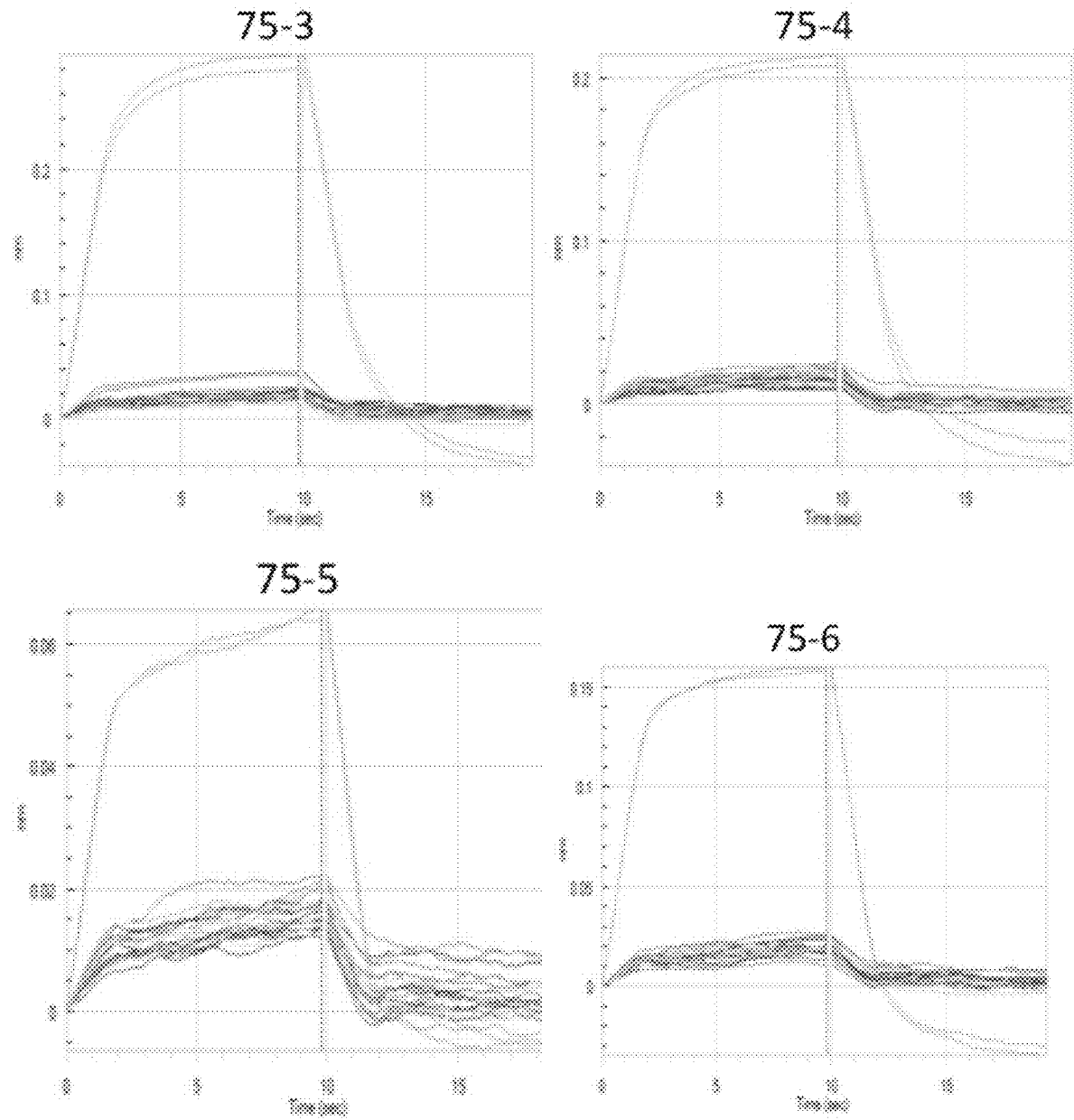
Figure 5:
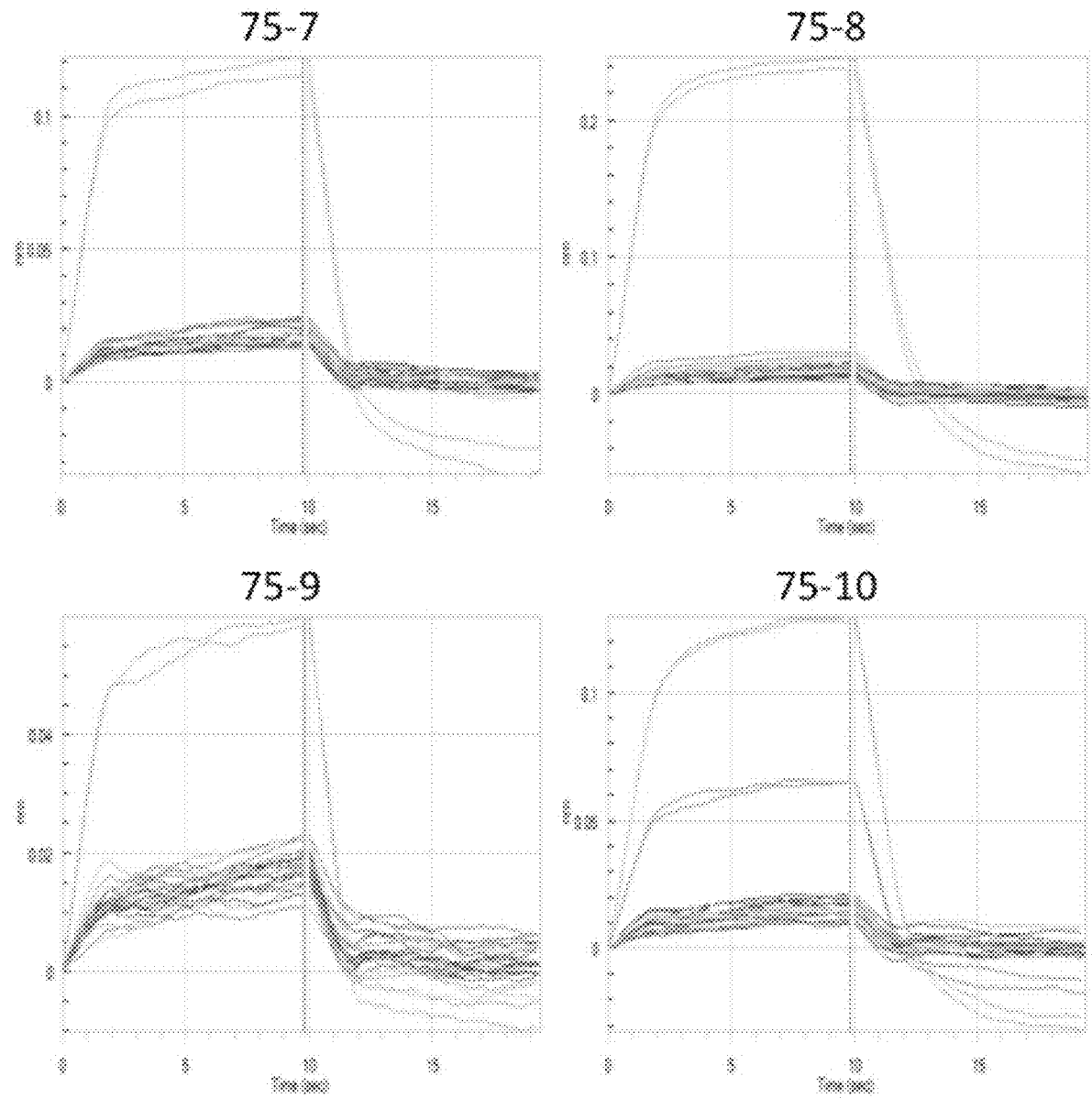
Figure 5:
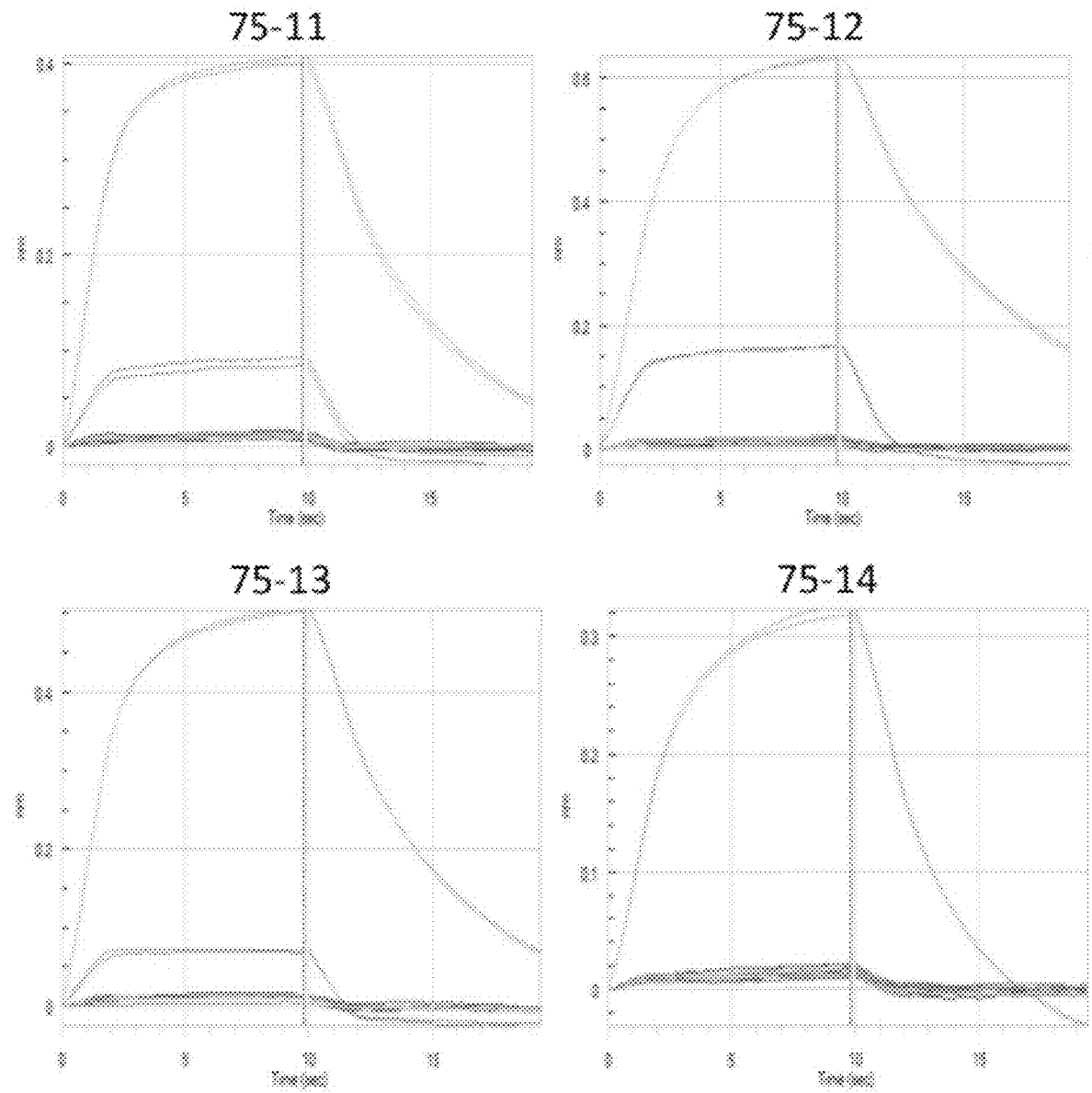
Figure 5:
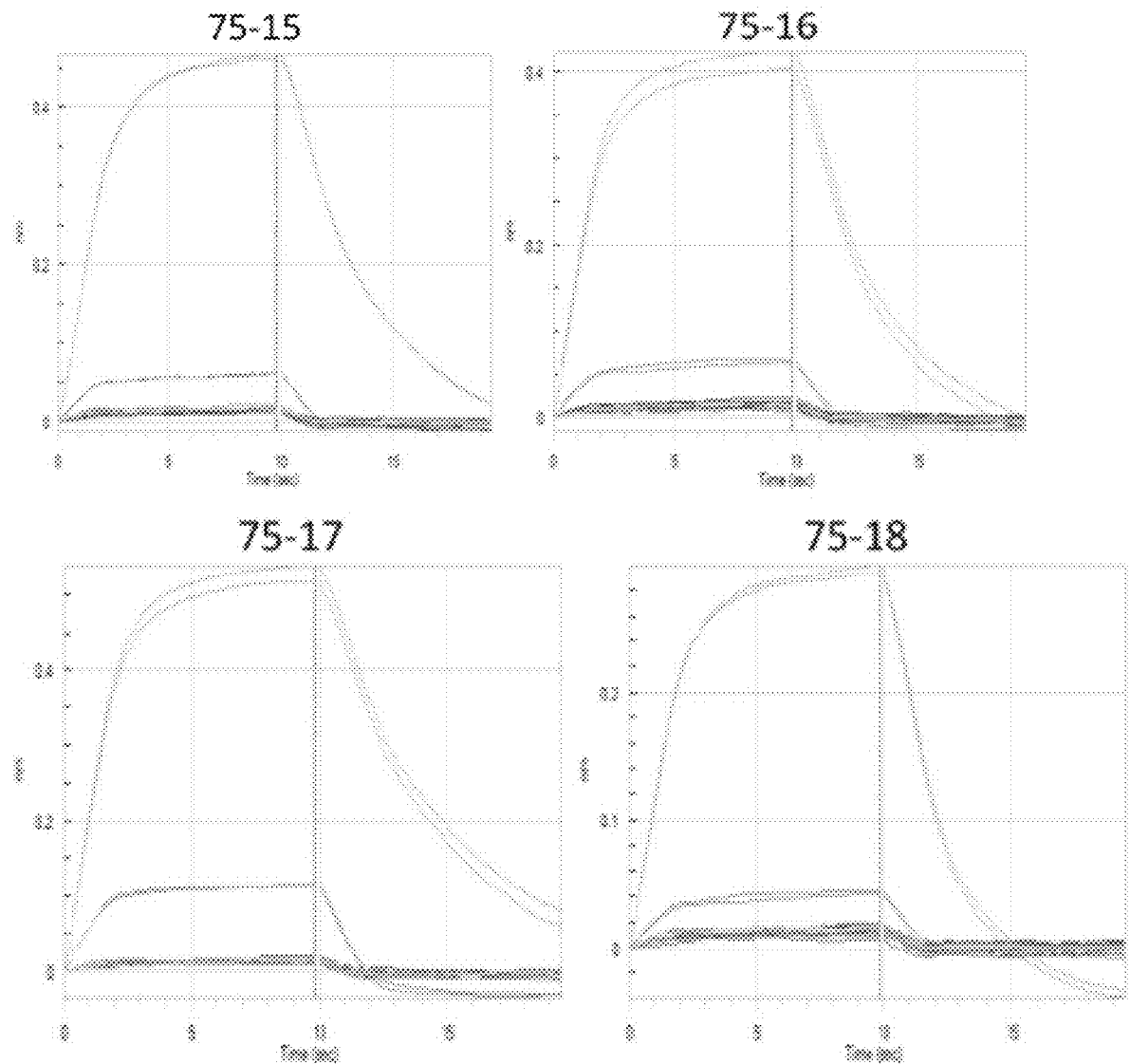
Figure 5:
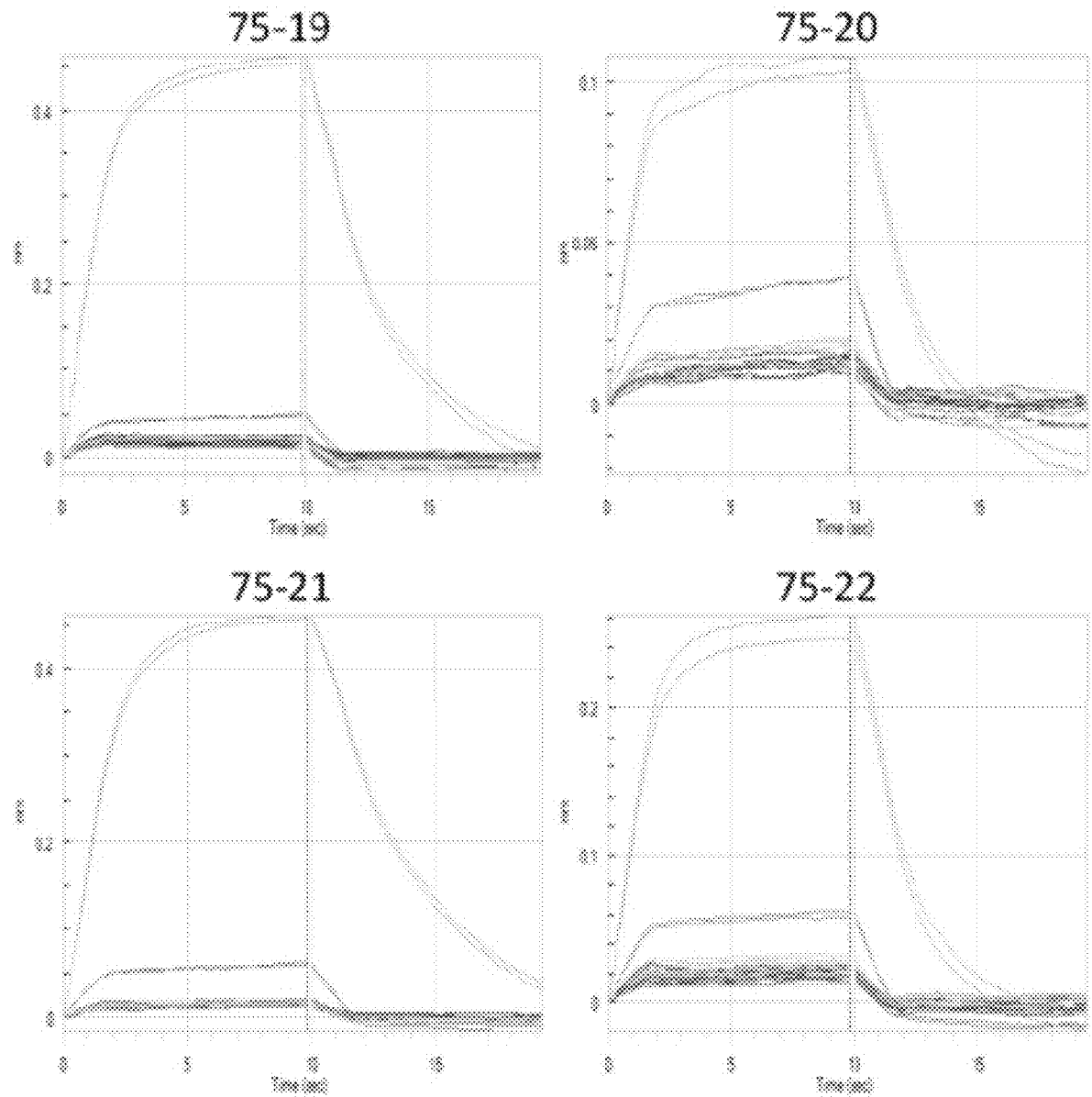
Figure 5:
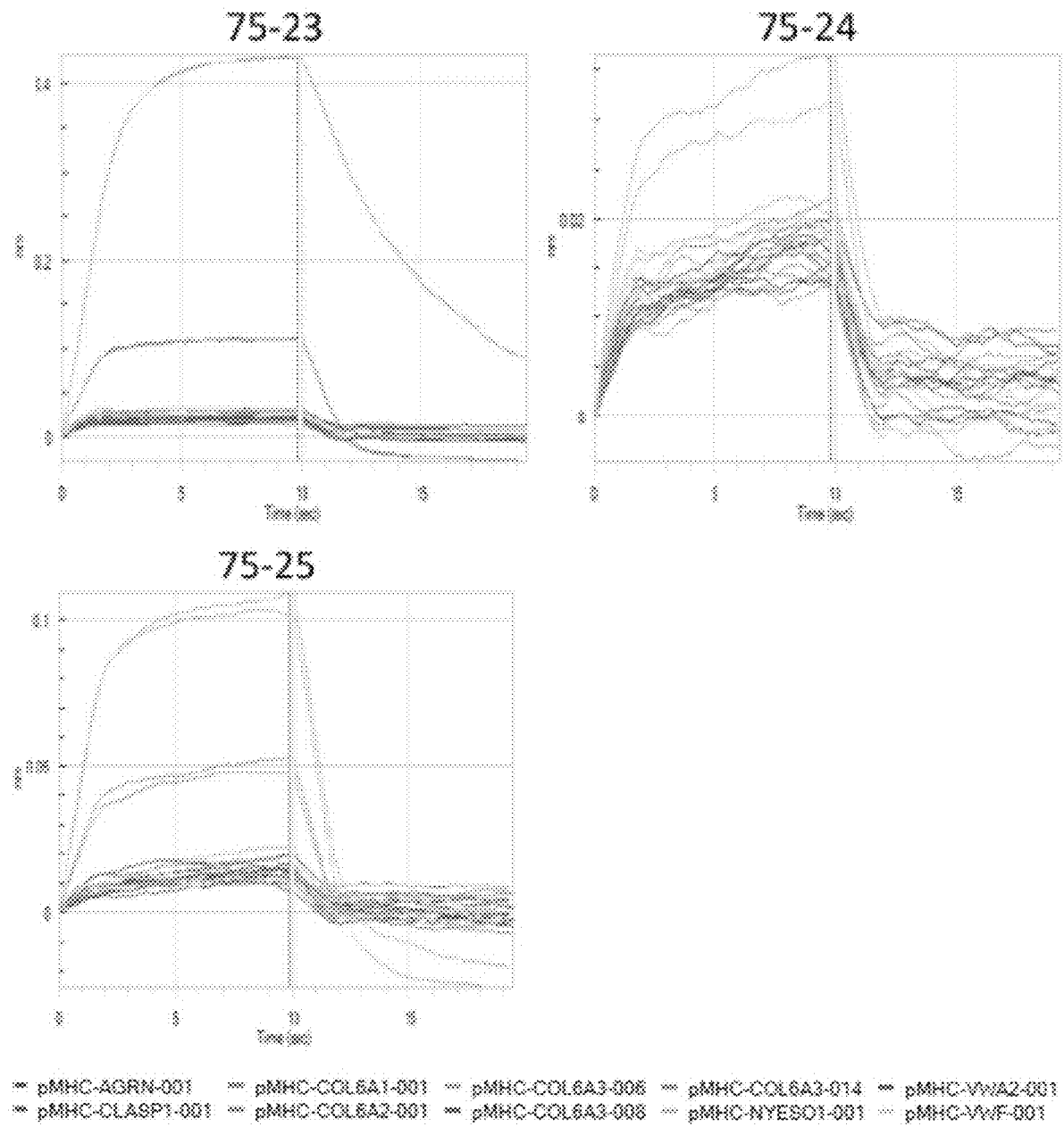
Figure 6:
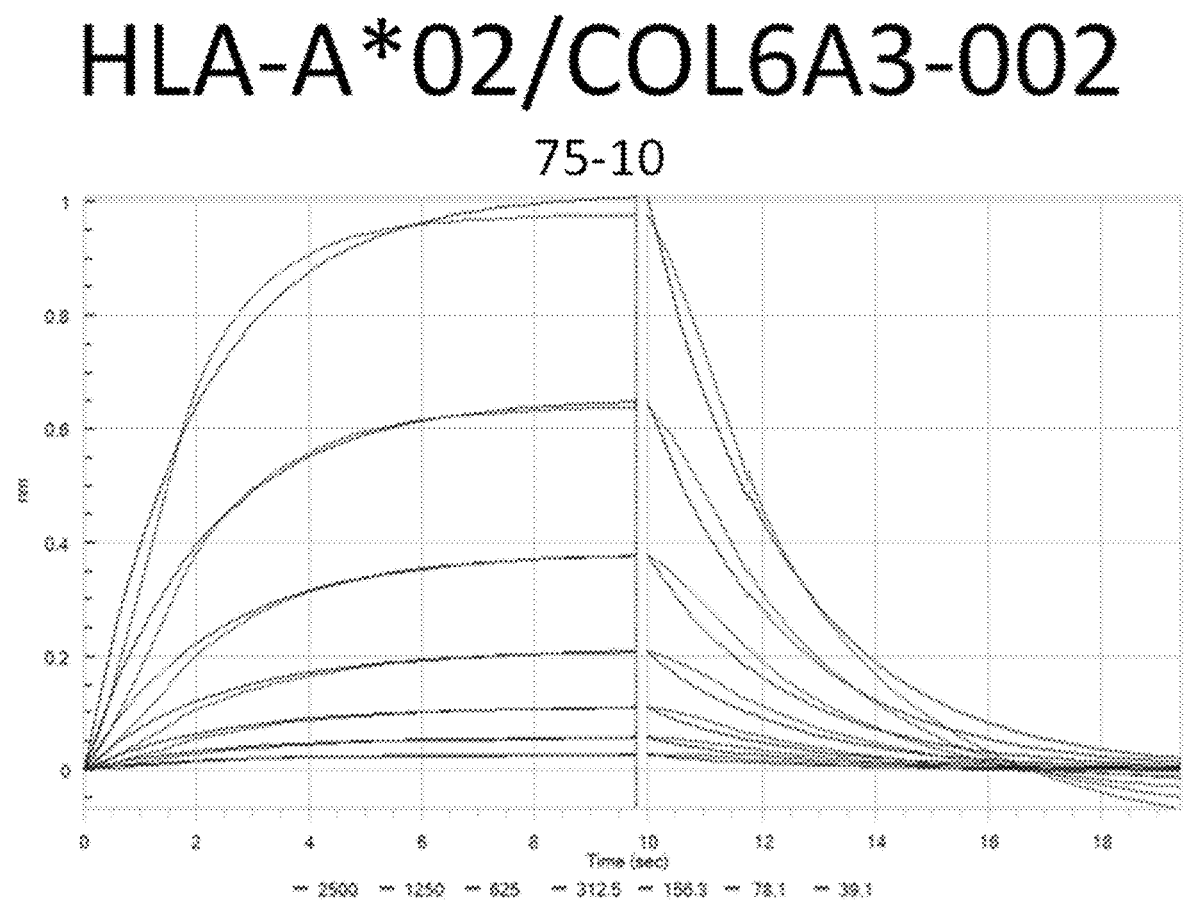
FIG. 6 shows a comparison of HLA-A*02/COL6A3-002 and HLA-A*02/COL6A1-001 (SEQ ID NO: 30) binding kinetics of different anti-CD3 Fab-scTv R4P3F9S fusion variants. Analyzed concentrations of Fab-scTv molecules are indicated.
Figure 6:
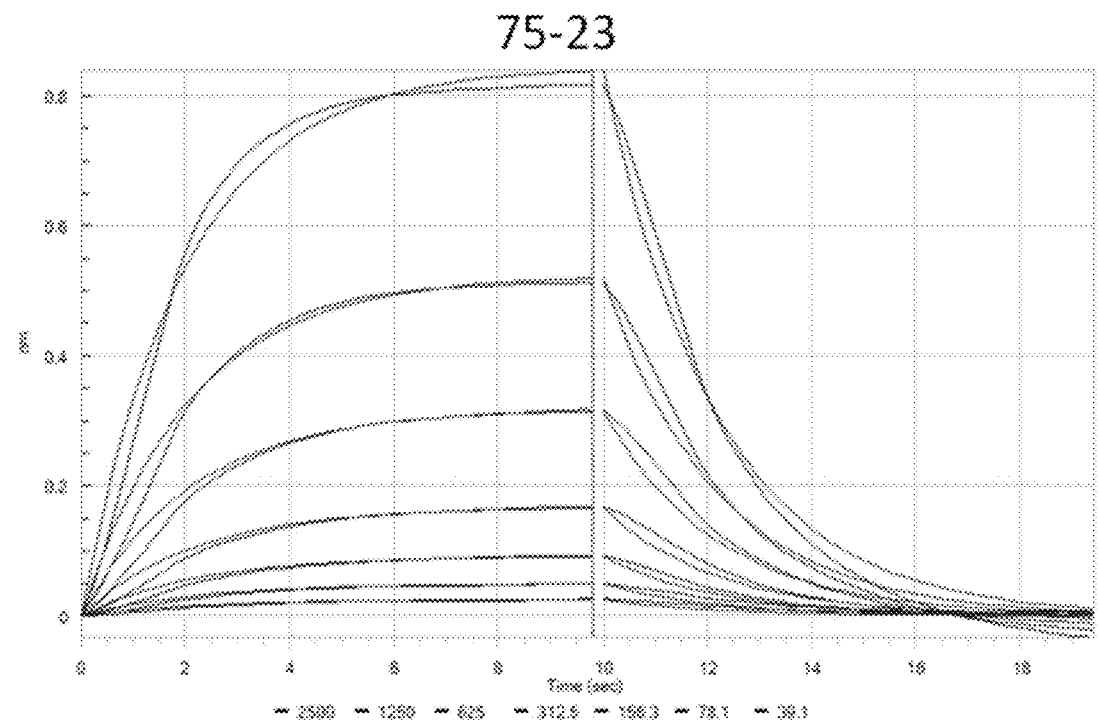

Binding affinity of anti-CD3-scTv R4P3F9S fusion proteins towards HLA-A*02 monomers with COL6A3-002 or different similar peptides was measured by biolayer interferometry. Measurements were done on an Octet RED384 system using settings recommended by the manufacturer. Briefly, purified Fab-scTv molecules were loaded onto biosensors (FAB2G) prior to analyzing serial dilutions of HLA-A*02/COL6A3-002. Compared to variants 75-1 and 75-24 comprising wild-type CDRa1 and wild-type CDRb1 increased binding affinities of up to 40-fold were observed for Fab-scTv variants with maturated CDRa1 and/or CDRb1 sequences (Table 3, FIG. 4). In order to evaluate the selectivity of binding to HLA-A*02/COL6A3-002, purified Fab-scTv molecules loaded onto FAB2G biosensors were screened for binding to 1 µM similar peptides (SEQ ID NOs: 28 to 36), each in complex with HLA-A*02. Except of HLA-A*02/COL6A1-001 (SEQ ID NO: 30), which was bound by most of the Fab-scTv variants containing maturated CDRa1 (SEQ ID NO: 26), Fab-scTv variants showed no binding to similar peptides (FIG. 5) arguing for high binding selectivity. For some Fab-scTv variants the therapeutic window between HLA-A*02/COL6A3-002 and HLA-A*02/COL6A1-001 binding was investigated by loading biotinylated peptide-HLA complexes onto biosensors (SA) and analyzing dilution series of Fab-scTv variants. While variant 75-10 comprising maturated CDRa1 (SEQ ID NO: 26) and wild-type CDRb1 (SEQ ID NO: 13) sequence showed 8-fold increased binding affinity to HLA-A*02/COL6A3-002 over HLA-A*02/COL6A1-001, an up to 57-fold increased binding affinity was detected for Fab-scTv variant 75-13 comprising a maturated CDRb1 (SEQ ID NO: 39) arguing for an improvement in therapeutic window (Table 4, FIG. 6).

Example 5: Use of Affinity-Maturated TCRs for Cellular Expression

Figure 7:
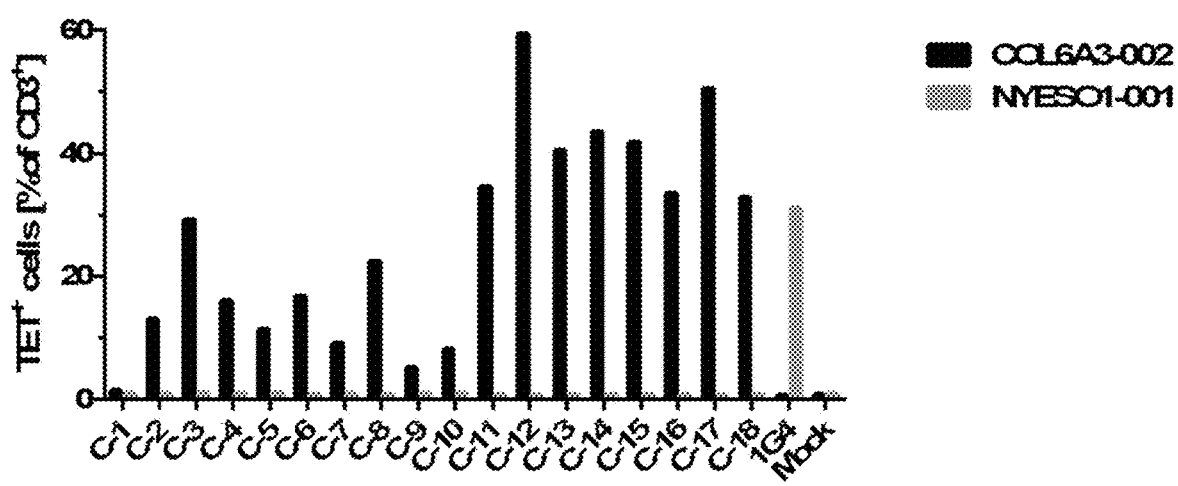
FIG. 7 shows staining of maturated R4P3F9 TCR variant expressing human CD8+ T cells with PE-labeled HLA-A*02/COL6A3-002 tetramers. For control purpose, no TCR (Mock) or the 1G4 TCR specific for NYESO1-001 was expressed and staining with PE-labeled HLA-A*02/NYESO1-001 tetramers was used.
Figure 8:
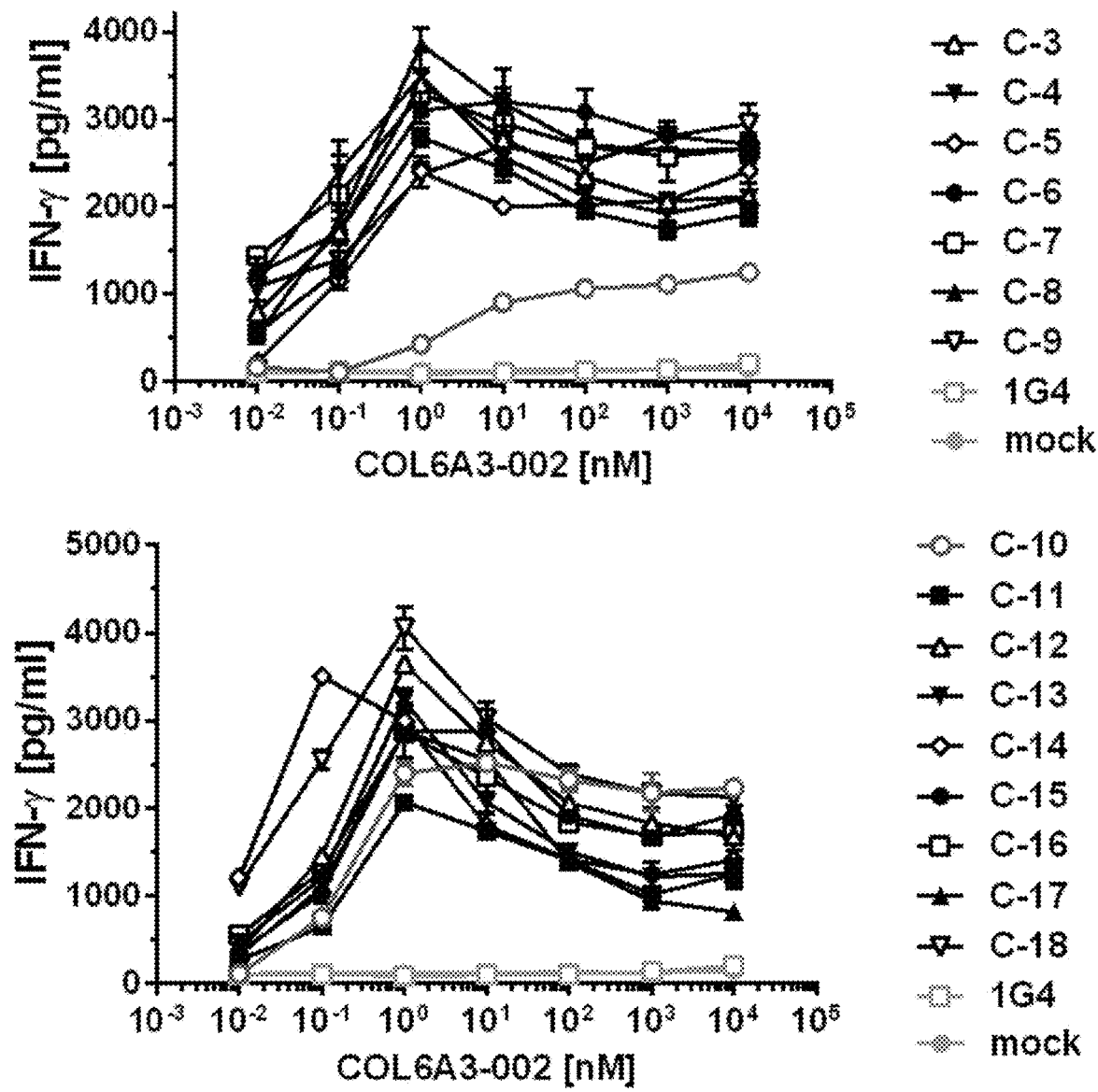
FIG. 8 shows IFN-gamma release of maturated R4P3F9 TCR variant expressing human CD8+ T cells in response to COL6A3-002. For control purpose, no TCR (mock) or the 1G4 TCR specific for NYESO1-001 was expressed. IFN-gamma release was determined by ELISA after co-culture of electroporated CD8+ T cells with T2 cells loaded with a serial dilution of COL6A3-002.
Figure 9:
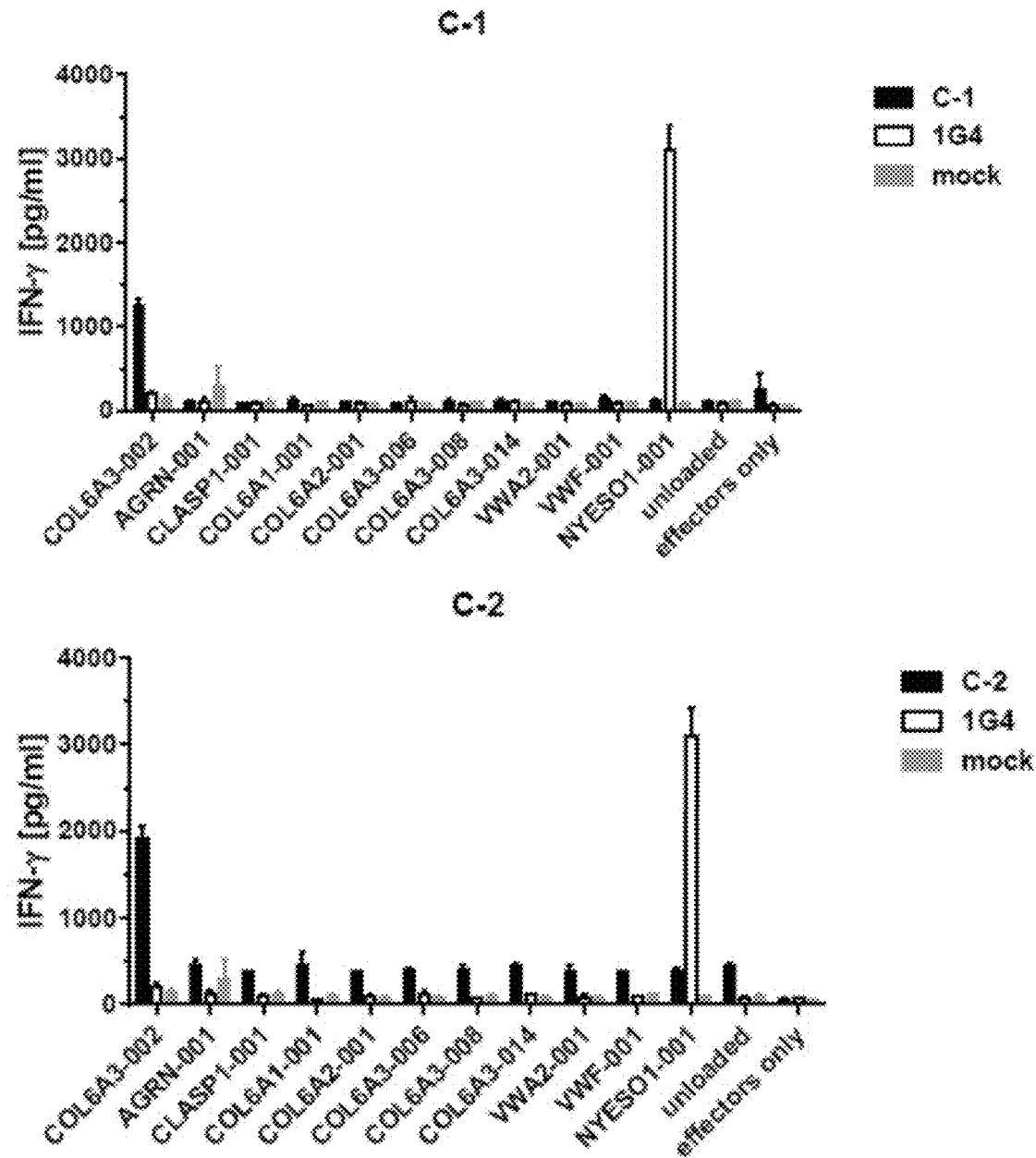
FIG. 9 shows IFN-gamma release of maturated R4P3F9 TCR variant expressing human CD8+ T cells in response to COL6A3-002 and different similar peptides. For control purpose, no TCR (mock) or the 1G4 TCR specific for NYESO1-001 was expressed. IFN-gamma release was determined by ELISA after co-culture of electroporated CD8+ T cells with T2 cells loaded with 10 µM of COL6A3-002 or similar peptides.
Figure 9:
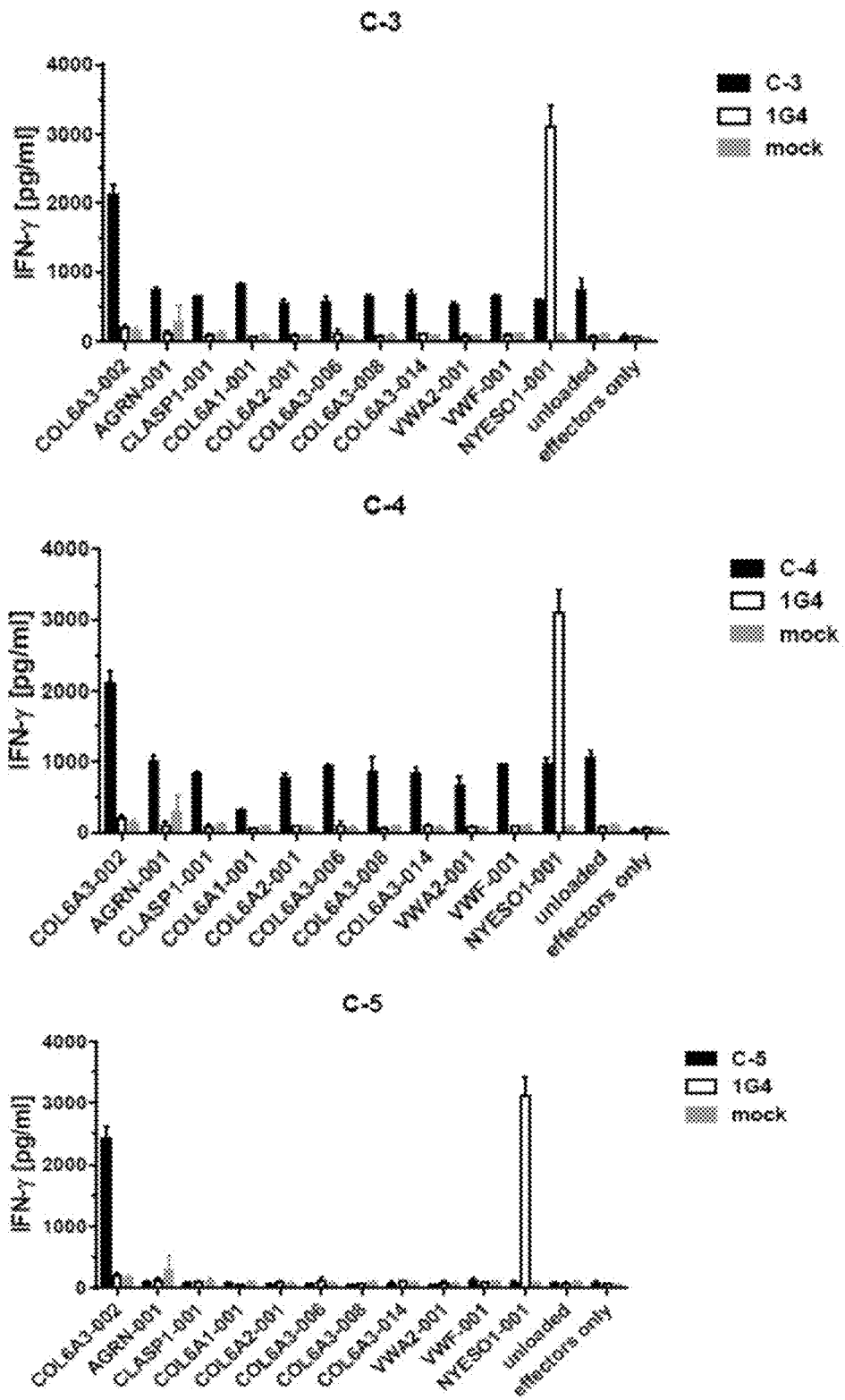
Figure 9:
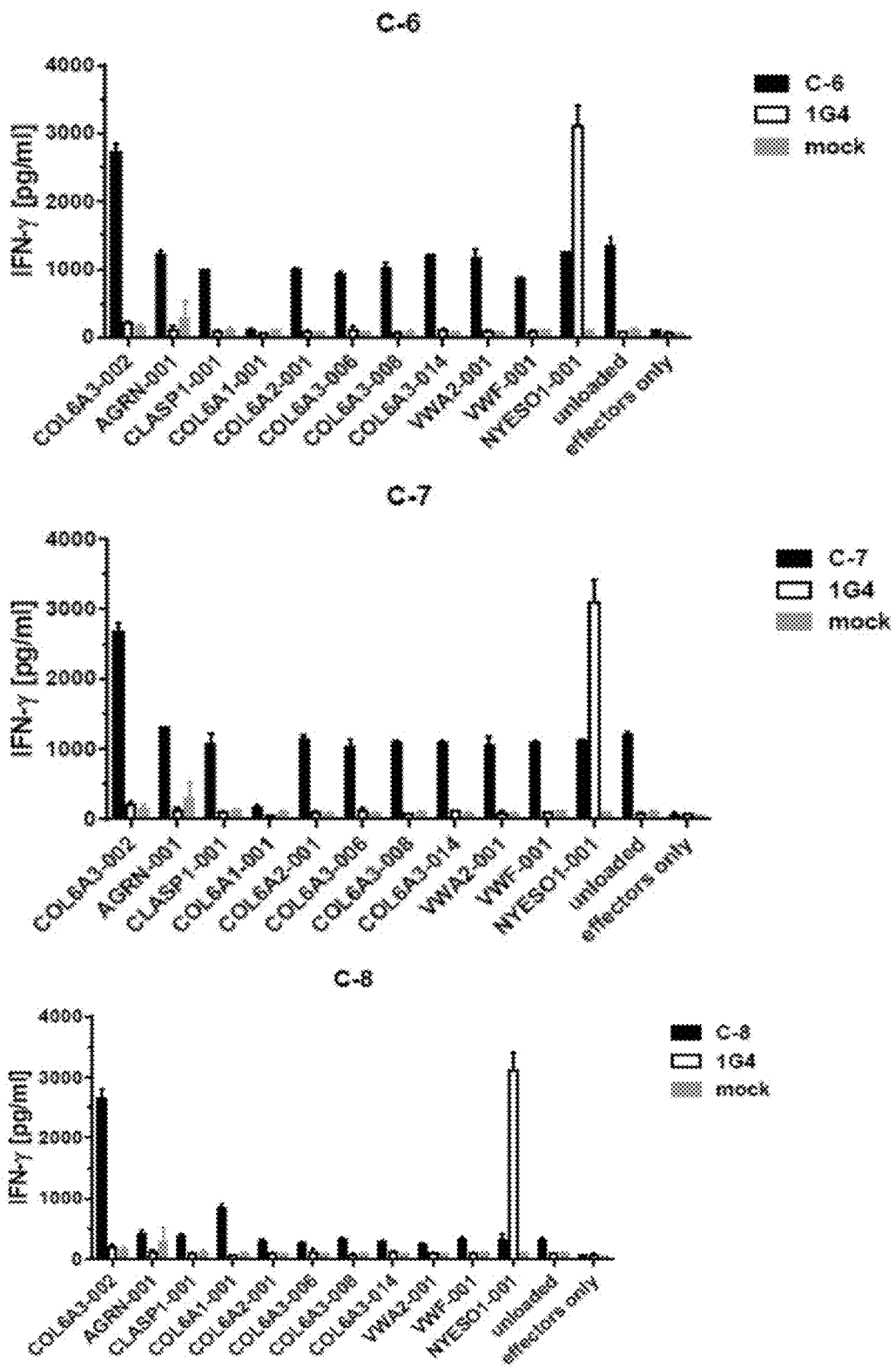
Figure 9:
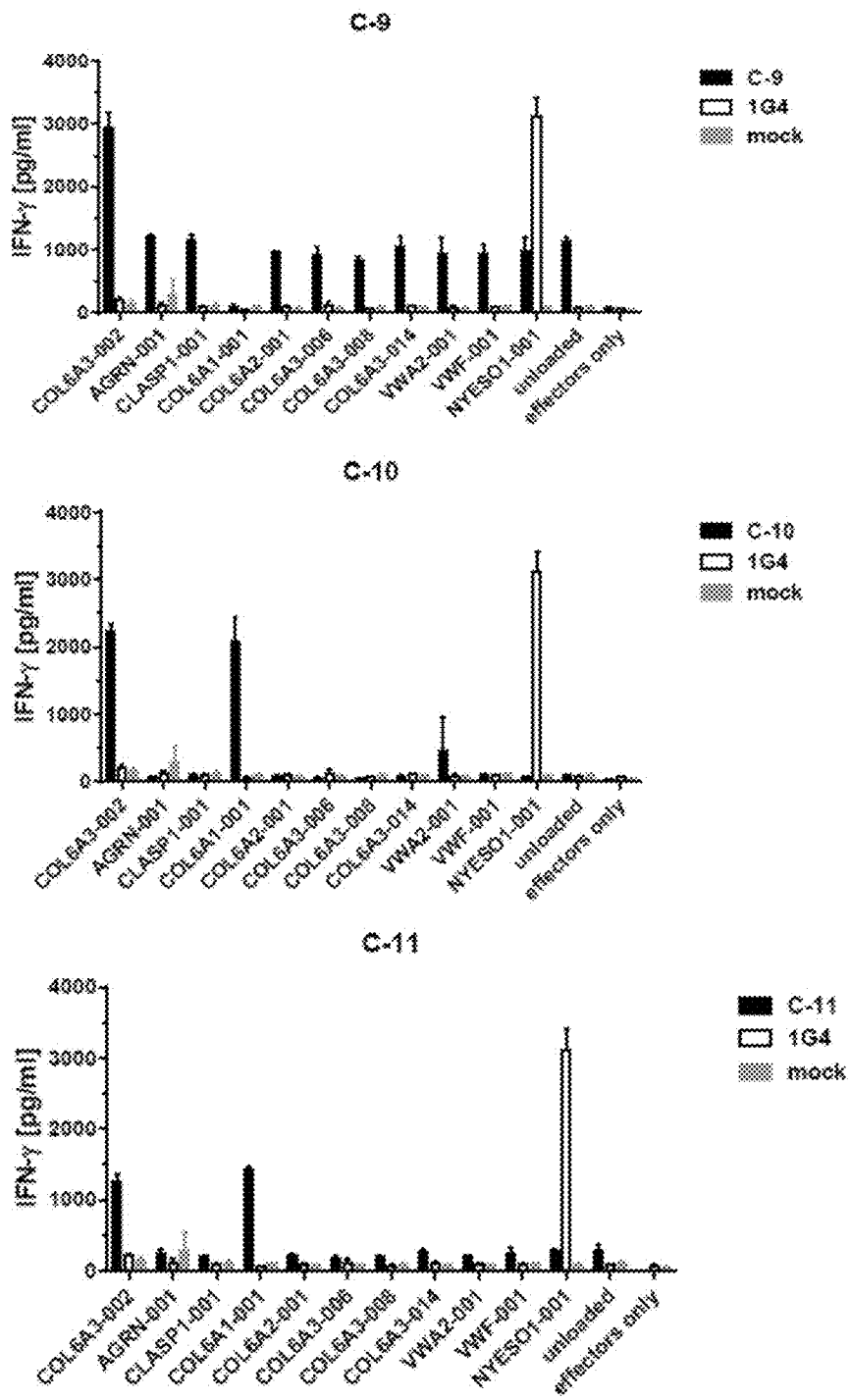
Figure 9:
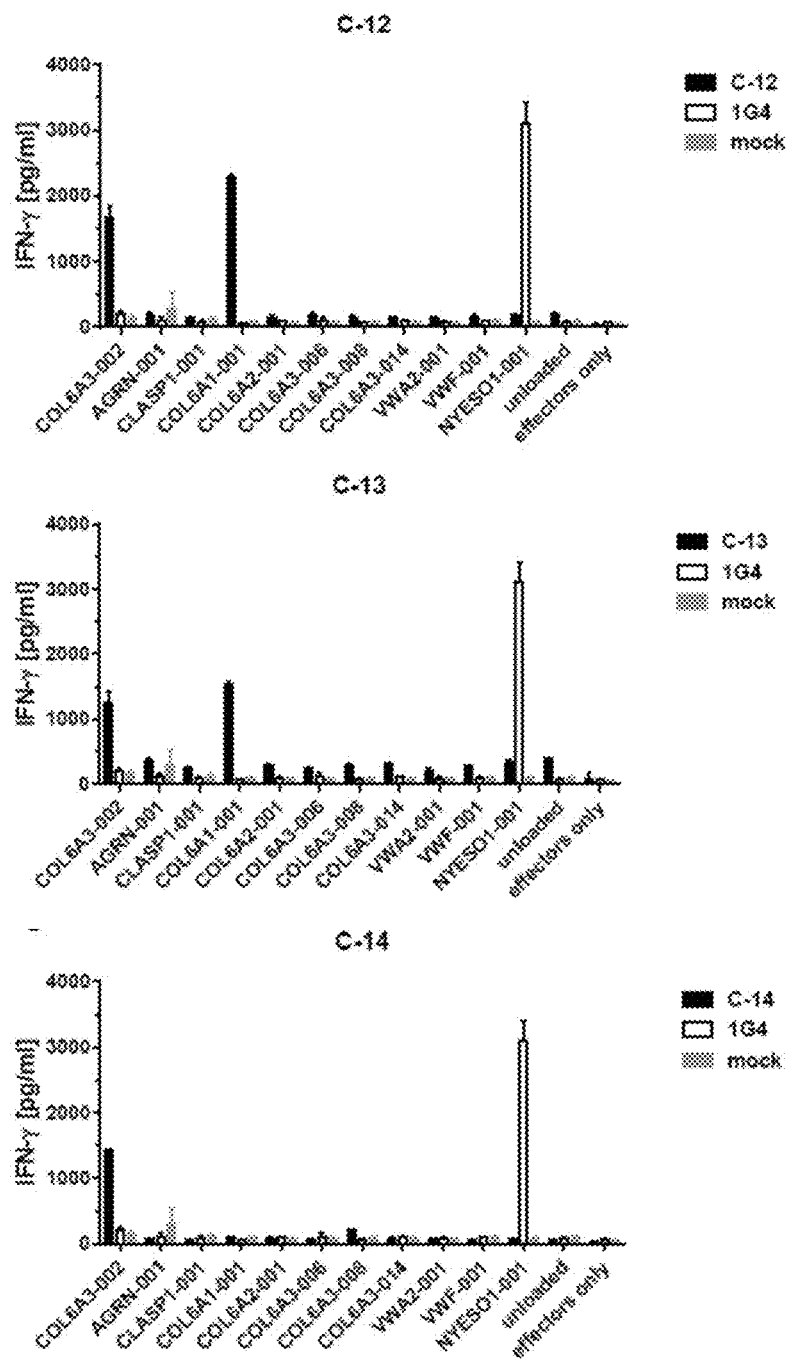
Figure 9:
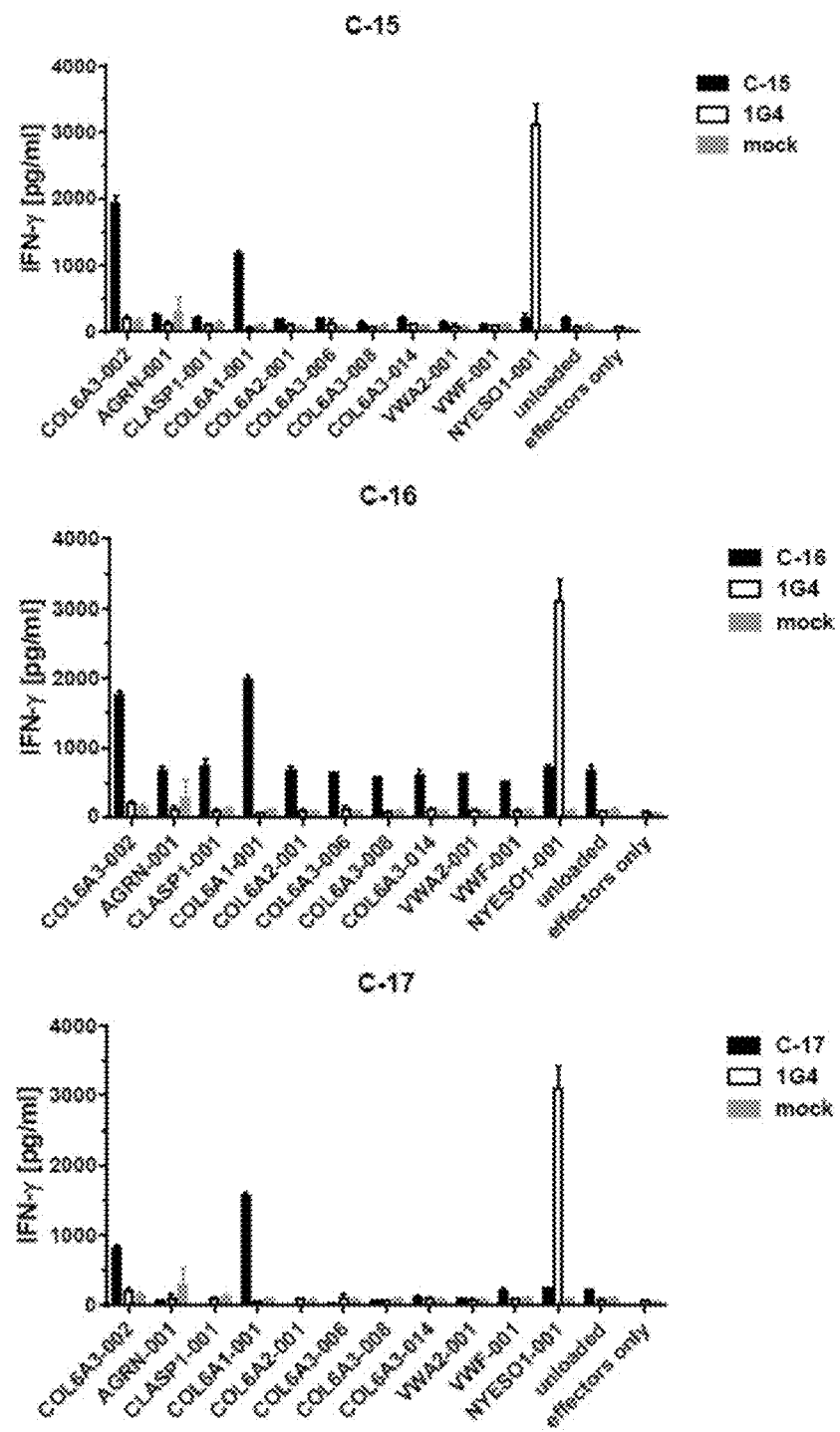
Figure 9:
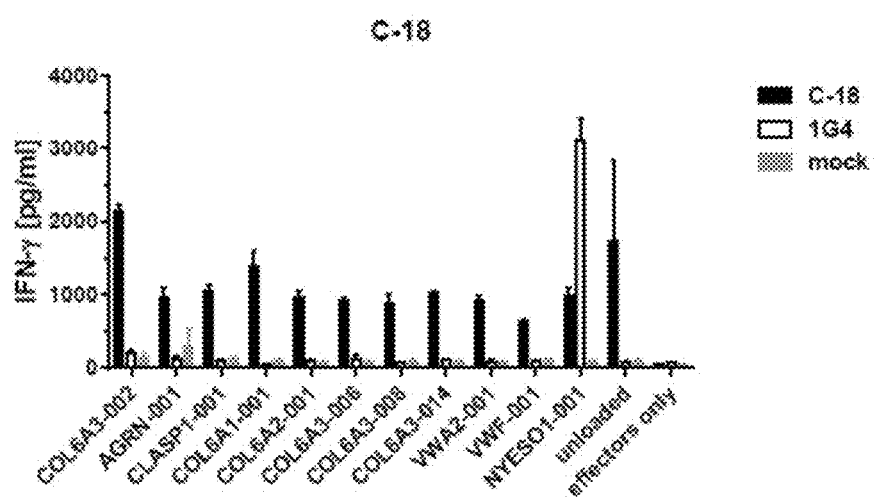

Modification of T cells to express TCRs recognizing a tumor-specific peptide-HLA is a promising alternative of redirecting T cells to cancer cells. As the usage of maturated CDR1 sequences could improve cell-bound TCRs against HLA-A*02/COL6A3-002, the identified CDRa1 and CDRb1 mutant sequences were grafted onto the parental TCR R4P3F9 (SEQ ID NOs: 2 and 10). The resulting mutant TCR variants (C-1 to C-18, Table 5) were expressed in human CD8[+] T cells after electroporation of respective mRNA generated by in vitro transcription of PCR-amplified DNA constructs. For control purpose, the 1G4 TCR (SEQ ID NOs: 53 and 57) against NYESO1-001 peptide (SEQ ID NO: 61) was expressed. After overnight incubation of RNA-electroporated CD8[+] T cells, expression of introduced TCR variants was analyzed by staining with PE-labeled HLA-A*02/COL6A3-002 tetramers or HLA-A*02/NYESO1-001 tetramers. While the parental TCR R4P3F9 variant C-1 showed only minimal staining with HLA-A*02/COL6A3-002 tetramers, the R4P3F9 TCR variants C-2 to C-18 with maturated CDRa1 and/or CDRb1 showed increased tetramer staining (FIG. 7). Functional activation of CD8$^+$ T cells (20,000 cells/well) expressing different maturated R4P3F9 TCR variants was investigated by determining levels of released IFN-gamma upon co-culture with T2 cells (20,000 cells/well) loaded with either a dilution series of COL6A3-002 (SEQ ID NO: 1) or 10 µM of COL6A3-002 and similar peptides (SEQ ID NOs: 28 to 36). Compared to the parental R4P3F9 TCR variant C-1, maturated TCR variants C-2 to C-18 showed increased IFN-gamma release with maximum levels reached already at lower peptide concentrations (FIG. 8). As expected no IFN-gamma release was observed with T cells expressing no TCR or the 1G4 control TCR specific for NYESO1-001. To analyze the selectivity of COL6A3-002 recognition of the maturated R4P3F9 TCR variants, the IFN-gamma release in response to T2 cells loaded with different similar peptides (SEQ ID NOs: 28 to 36) was analyzed and revealed different selectivity profiles for the maturated R4P3F9 TCR variants. Most interestingly, the TCR variants C-5 (SEQ ID Nos 62 and 2) and C-14 (SEQ ID NOs: 62 and 63) comprising the same maturated CDRb1 (SEQ ID NO: 40) did not show any cross-reactivity towards COL6A1-001 or other similar peptides (FIG. 9) making affinity maturated R4P3F9 TCR variants C-5 and C14 most promising candidates for cellular TCR-based tumor targeting.

TABLE 5

Nomenclature of cellular TCR variants. The molecules are based on SEQ ID NOs 2 and 10 and the indicated CDRa1 and CDRb1 variants.

| Variant | CDRa1 | CDRb1 |
|---------|-------|-------|
| C-1 | DRGSQS (SEQ ID NO. 5) | RSGDLS (SEQ ID NO. 13) |
| C-2 | DRGSQS (SEQ ID NO. 5) | ARWHNN (SEQ ID NO. 37) |
| C-3 | DRGSQS (SEQ ID NO. 5) | AKDHLN (SEQ ID NO. 38) |
| C-4 | DRGSQS (SEQ ID NO. 5) | ARWHRN (SEQ ID NO. 39) |
| C-5 | DRGSQS (SEQ ID NO. 5) | AMDHPY (SEQ ID NO. 40) |
| C-6 | DRGSQS (SEQ ID NO. 5) | ATDHYN (SEQ ID NO. 41) |
| C-7 | DRGSQS (SEQ ID NO. 5) | ARYHTN (SEQ ID NO. 42) |
| C-8 | DRGSQS (SEQ ID NO. 5) | APYHLN (SEQ ID NO. 43) |
| C-9 | DRGSQS (SEQ ID NO. 5) | AKDHTN (SEQ ID NO. 44) |
| C-10 | DRRSQS (SEQ ID NO. 26) | RSGDLS (SEQ ID NO. 13) |
| C-11 | DRRSQS (SEQ ID NO. 26) | ARWHNN (SEQ ID NO. 37) |
| C-12 | DRRSQS (SEQ ID NO. 26) | AKDHLN (SEQ ID NO. 38) |
| C-13 | DRRSQS (SEQ ID NO. 26) | ARWHRN (SEQ ID NO. 39) |
| C-14 | DRRSQS (SEQ ID NO. 26) | AMDHPY (SEQ ID NO. 40) |
| C-15 | DRRSQS (SEQ ID NO. 26) | ATDHYN (SEQ ID NO. 41) |
| C-16 | DRRSQS (SEQ ID NO. 26) | ARYHTN (SEQ ID NO. 42) |
| C-17 | DRRSQS (SEQ ID NO. 26) | APYHLN (SEQ ID NO. 43) |
| C-18 | DRRSQS (SEQ ID NO. 26) | AKDHTN (SEQ ID NO. 44) |

Figure 10:
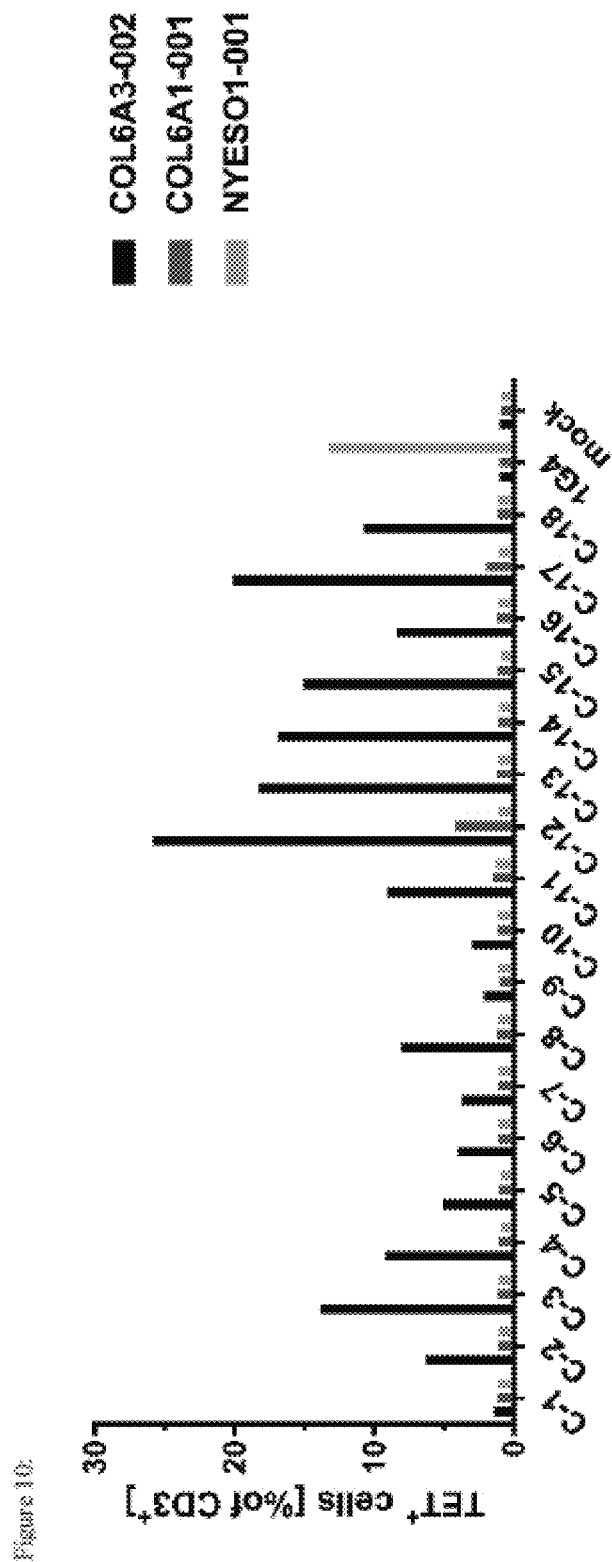
FIG. 10 shows staining of maturated R4P3F9 TCR variant expressing human CD8+ T cells with PE-labeled peptide-HLA-A*02 tetramers. For control purpose, no TCR (Mock) or the 1G4 TCR specific for NYESO1-001 was expressed and staining with PE-labeled HLA-A*02/NYESO1-001 tetramers was used.
Figure 11:
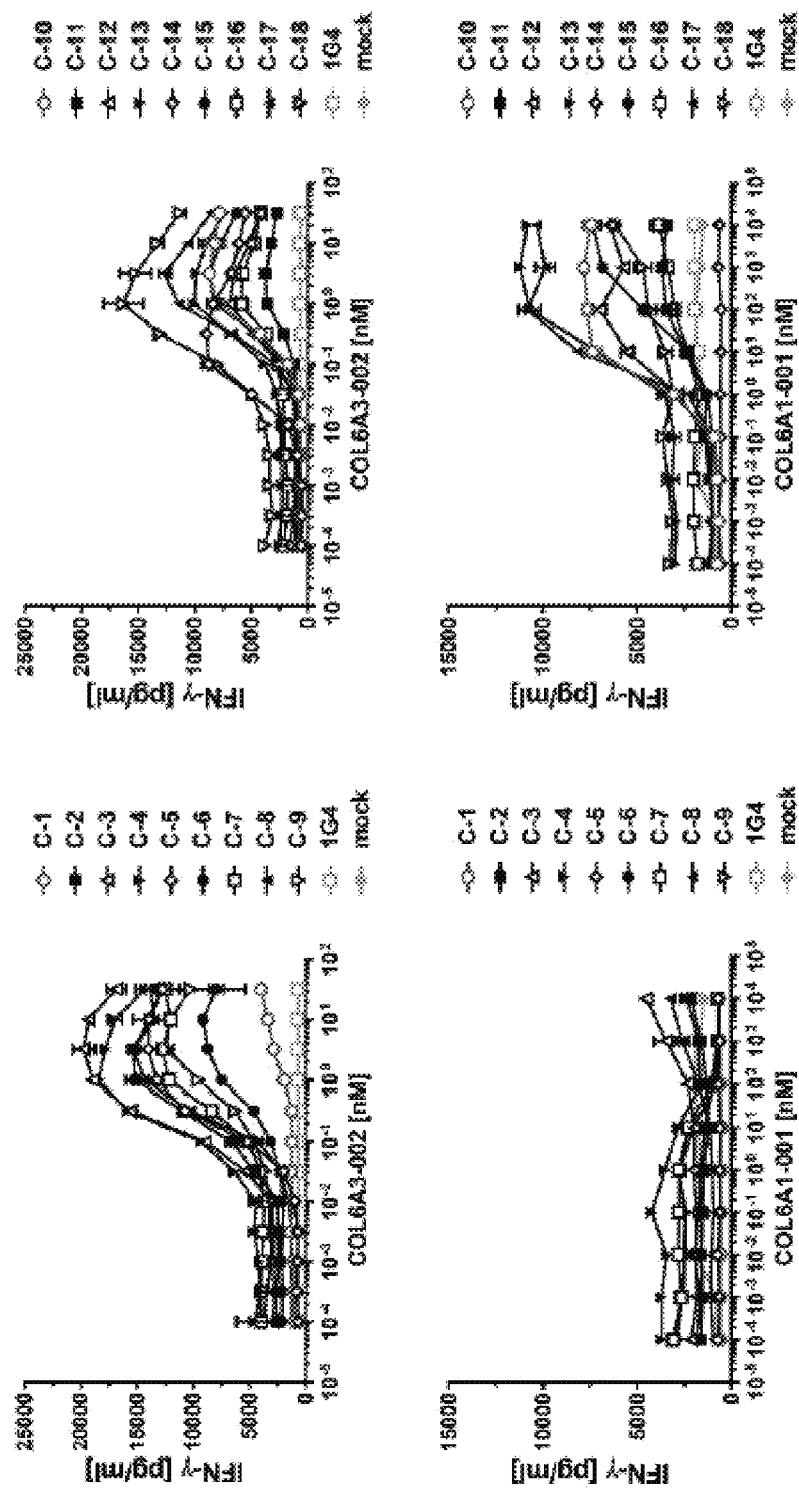
FIG. 11 shows IFN-gamma release of maturated R4P3F9 TCR variant expressing human CD8+ T cells in response to COL6A3-002 or COL6A1-001. For control purpose, no TCR (mock) or the 1G4 TCR specific for NYESO1-001 was expressed. IFN-gamma release was determined by ELISA after co-culture of electroporated CD8+ T cells with T2 cells loaded with a serial dilution of COL6A3-002 or COL6A1-001.

Example 6: Window of COL6A3-002 and COL6A1-001 Recognition of Cellular TCR Variants Cellular expression and analysis of R4P3F9 variants was performed as described above. In accordance with previous experiments (FIG. 7), staining of T cells expressing R4P3F9 TCR variants C-2 to C-18 with PE-labeled HLA-A*02/COL6A3-002 tetramers were increased compared to the parental TCR C-1. Additionally, TCR variants C-12 and C-17 showed binding to HLA-A*02/COL6A1-001 (FIG. 10). Expression of all maturated R4P3F9 variants improved functional activation of CD8$^+$ T cells in response to T2 cells loaded with a dilution series of COL6A3-002 (SEQ ID NO: 1) reaching 5- to 90-fold lower $EC_{50}$ values compared to the parental TCR C-1 (FIG. 11, Table 6). The lowest $EC_{50}$ value was found for variant C-14. Again, TCR variants C-5 (SEQ ID NOs 62 and 2) and C-14 (SEQ ID NOs: 62 and 63) comprising the same maturated CDRb1 (SEQ ID NO: 40) did not show any cross-reactivity towards COL6A1-001, while other variants showed strong recognition with $EC_{50}$ windows (COL6A3-002 vs. COL6A1-001) as low as factor 5.

TABLE 6

$EC_{50}$ values [nM] of IFN-γ release of T cells expressing R4P3F9 variants after coculture with T2 cells loaded with COL6A3-002 or COL6A1-001.

| Variant | $EC_{50}$ COL6A3-002 [nM] | $EC_{50}$ COL6A1-001 [nM] |
|---------|---------------------------|---------------------------|
| C-1 | 2.51 | — |
| C-2 | 0.16 | — |
| C-3 | 0.14 | 871$^a$ |
| C-4 | 0.13 | — |
| C-5 | 0.15 | — |
| C-6 | 0.48 | — |
| C-7 | 0.29 | — |
| C-8 | 0.20 | 350 |
| C-9 | 0.55 | — |
| C-10 | 0.32 | 1.5 |
| C-11 | 0.32 | 8.2 |
| C-12 | 0.20 | 1.9 |
| C-13 | 0.23 | 9.7 |
| C-14 | 0.03 | — |
| C-15 | 0.31 | 69 |
| C-16 | 0.34 | 78 |
| C-17 | 0.33 | 4.1 |
| C-18 | 0.14 | 280089$^a$ |

$^a$plateau not reached

Example 7: Efficacy of Maturated R4P3F9 Variants C-5 and C-14 on Tumor Cell Lines Cellular expression and analysis of R4P3F9 variants was performed as described above.

Figure 12:
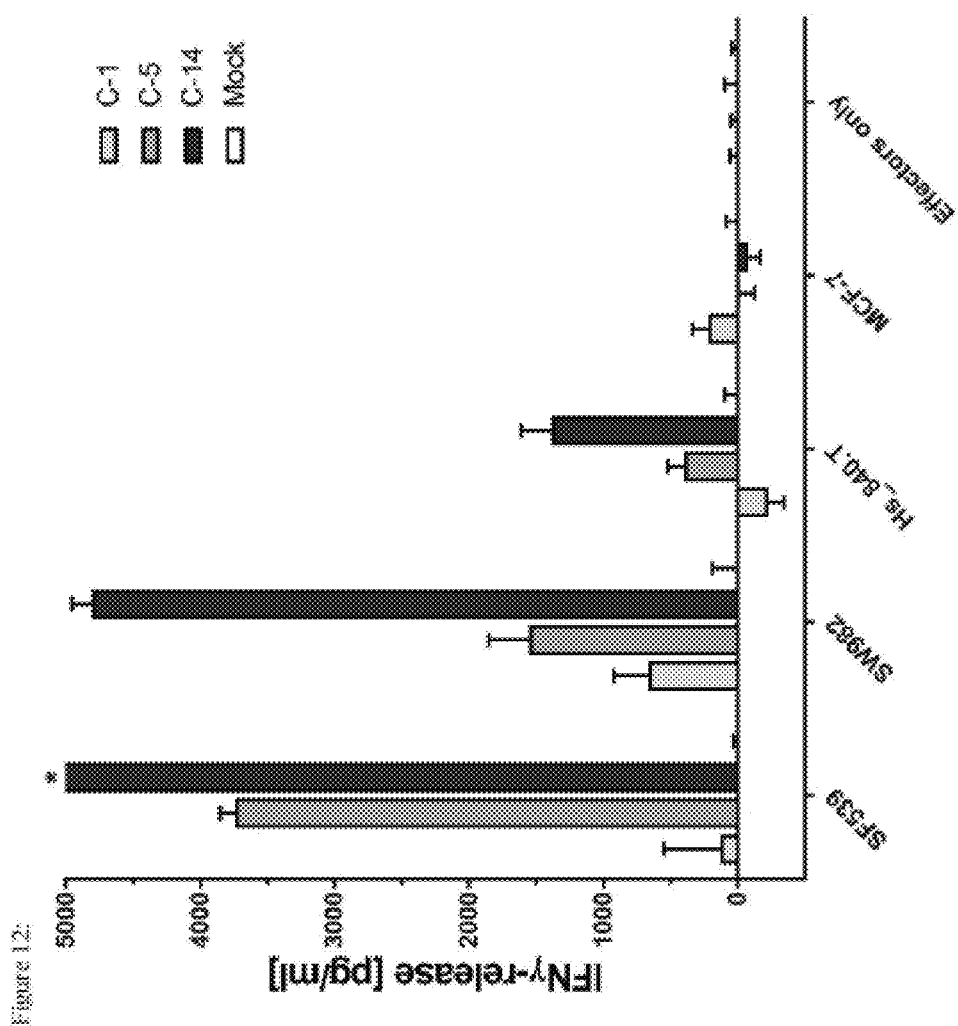
FIG. 12 shows IFN-gamma release of primary human CD8+ T cells expressing R4P3F9 TCR variants upon co-culture with different tumor cell lines. SF539, SW982 and Hs840.T cells present the target peptide at different levels. MCF-7 cells do not present the target peptide. As controls, effector cells without exogenous TCR were analyzed along with cells with TCRs of interest. IFN-gamma release was determined by ELISA. * marks a data point that is out of scale.

Expression of the maturated R4P3F9 variants C-5 (SEQ ID NOs 62 and 2) and C-14 (SEQ ID NOs: 62 and 63) improved functional activation of CD8$^+$ T cells in response to COL6A3-002 (SEQ ID NO: 1)-presenting tumor cell lines as compared to the parental TCR C-1 (FIG. 12). The tumor cell lines used during this study present different amounts of target peptide. SF539 cells carry ~4000 copies of HLA-A*02/COL6A3-002 per cell and SW982 cells carry ~460 copies per cell. Whereas the parental TCR C-1 did not mediate strong T-cell activation upon co-culture with target-positive cell lines, TCR variant C-14 showed even stronger improvement of functional activation than TCR variant C-5. These data are in line with $EC_{50}$ improvements from TCR C-1 to C-5 and to C-14 (table 6). The target-negative tumor cell line MCF-7 was not recognized by any of these TCRs.

REFERENCES

Aleksic et al. 2012: Different affinity windows for virus and cancer-specific T-cell receptors—implications for therapeutic strategies, Eur J Immunol. 2012 December; 42(12):3174-9;

Hickman et al. 2016: Antigen Selection for Enhanced Affinity T-Cell Receptor-Based Cancer Therapies, J Biomol Screen. 2016 September; 21(8):769-85;

Boder and Wittrup 2000: Yeast surface display for directed evolution of protein expression, affinity, and stability, Methods Enzymol. 2000; 328:430-44;

Boder and Wittrup 1997: Yeast surface display for screening combinatorial polypeptide libraries, Nat Biotechnol. 1997 June; 15(6):553-7;

Smith et al. 2015: T Cell Receptor Engineering and Analysis Using the Yeast Display Platform, Methods Mol Biol. 2015; 1319:95-141;

DE102016121899.5

DE102016115246

The invention claimed is:

1. A method of treating a patient who has cancer that presents a peptide consisting of the amino acid sequence of FLLDGSANV (SEQ ID NO: 1) in a complex with HLA-A*02, comprising administering to the patient a population of transformed T cells expressing at least one vector encoding a T cell receptor (TCR),
wherein the TCR comprises SEQ ID NOs: 26, 6, 7, 40, 14, and 15,
wherein the TCR binds to a peptide consisting of the amino acid sequence of FLLDGSANV (SEQ ID NO: 1) in a complex with HLA-A*02, and
wherein the cancer is selected from breast cancer, gallbladder cancer, colon cancer, esophageal cancer, gastrointestinal carcinoid tumor, lung cancer, melanoma, non-Hodgkin lymphoma, pancreatic cancer, rectal cancer, gastric cancer, and urinary bladder cancer.

2. The method of claim 1, wherein the population of transformed cells are produced by a method comprising
isolating a T cell from a subject,
transforming the cell with at least one vector encoding the TCR to produce a transformed cell, and
expanding the transformed cell to produce the population of transformed cells.

3. The method of claim 2, wherein the subject is the patient.

4. The method of claim 1, wherein said T cells are CD8+ T cells.

5. The method of claim 1, wherein the TCR comprises an α chain comprising an amino acid sequence with at least 95% identity to SEQ ID NO: 63 and a β chain comprising an amino acid sequence with at least 95% identity to SEQ ID NO: 62.

6. The method of claim 1, wherein the population of transformed cells are administered in the form of a pharmaceutical composition.

7. The method of claim 6, wherein the pharmaceutical composition comprises a chemotherapeutic agent selected from the group consisting of asparaginase, busulfan, carboplatin, cisplatin, daunorubicin, doxorubicin, fluorouracil, gemcitabine, hydroxyurea, methotrexate, paclitaxel, rituximab, vinblastine, and vincristine.

8. The method of claim 1, wherein the TCR comprises:
a CDR1α chain comprising the amino acid sequence of SEQ ID NO: 26
a CDR2α chain comprising the amino acid sequence of SEQ ID NO: 6,
a CDR3α chain comprising the amino acid sequence of SEQ ID NO: 7,
a CDR1β chain comprising the amino acid sequence of SEQ ID NO: 40,
a CDR2β chain comprising the amino acid sequence of SEQ ID NO: 14, and
a CDR3β chain comprising the amino acid sequence of SEQ ID NO: 15.

9. The method of claim 1, wherein the TCR comprises:
a CDR1α chain consisting of the amino acid sequence of SEQ ID NO: 26
a CDR2α chain comprising the amino acid sequence of SEQ ID NO: 6,
a CDR3α chain comprising the amino acid sequence of SEQ ID NO: 7,
a CDR1β chain consisting of the amino acid sequence of SEQ ID NO: 40,
a CDR2β chain comprising the amino acid sequence of SEQ ID NO: 14, and
a CDR3β chain comprising the amino acid sequence of SEQ ID NO: 15.

10. The method of claim 1, wherein the TCR comprises:
a CDR1α chain comprising the amino acid sequence of SEQ ID NO: 26
a CDR2α chain consisting of the amino acid sequence of SEQ ID NO: 6,
a CDR3α chain comprising the amino acid sequence of SEQ ID NO: 7,
a CDR1β chain comprising the amino acid sequence of SEQ ID NO: 40,
a CDR2β chain consisting of the amino acid sequence of SEQ ID NO: 14, and
a CDR3β chain comprising the amino acid sequence of SEQ ID NO: 15.

11. The method of claim 1, wherein the TCR comprises:
a CDR1α chain comprising the amino acid sequence of SEQ ID NO: 26
a CDR2α chain comprising the amino acid sequence of SEQ ID NO: 6,
a CDR3α chain consisting of the amino acid sequence of SEQ ID NO: 7,
a CDR1β chain comprising the amino acid sequence of SEQ ID NO: 40,
a CDR2β chain comprising the amino acid sequence of SEQ ID NO: 14, and
a CDR3β chain comprising the amino acid sequence of SEQ ID NO: 15.

12. The method of claim 1, wherein the TCR comprises:
a CDR1α chain consisting of the amino acid sequence of SEQ ID NO: 26
a CDR2α chain consisting of the amino acid sequence of SEQ ID NO: 6,
a CDR3α chain comprising the amino acid sequence of SEQ ID NO: 7,
a CDR1β chain comprising the amino acid sequence of SEQ ID NO: 40,
a CDR2β chain consisting of the amino acid sequence of SEQ ID NO: 14, and
a CDR3β chain comprising the amino acid sequence of SEQ ID NO: 15.

13. The method of claim 1, wherein the TCR comprises:
a CDR1α chain consisting of the amino acid sequence of SEQ ID NO: 26
a CDR2α chain comprising the amino acid sequence of SEQ ID NO: 6,
a CDR3α chain consisting of the amino acid sequence of SEQ ID NO: 7,
a CDR1β chain consisting of the amino acid sequence of SEQ ID NO: 40,
a CDR2β chain comprising the amino acid sequence of SEQ ID NO: 14, and
a CDR3β chain consisting of the amino acid sequence of SEQ ID NO: 15.

14. The method of claim 1, wherein the TCR comprises:
a CDR1α chain comprising the amino acid sequence of SEQ ID NO: 26
a CDR2α chain consisting of the amino acid sequence of SEQ ID NO: 6,
a CDR3α chain consisting of the amino acid sequence of SEQ ID NO: 7,
a CDR1β chain comprising the amino acid sequence of SEQ ID NO: 40,
a CDR2β chain consisting of the amino acid sequence of SEQ ID NO: 14, and
a CDR3β chain consisting of the amino acid sequence of SEQ ID NO: 15.

15. The method of claim 1, wherein the TCR comprises:
a CDR1α chain consisting of the amino acid sequence of SEQ ID NO: 26
a CDR2α chain consisting of the amino acid sequence of SEQ ID NO: 6,
a CDR3α chain consisting of the amino acid sequence of SEQ ID NO: 7,
a CDR1β chain consisting of the amino acid sequence of SEQ ID NO: 40,
a CDR2β chain consisting of the amino acid sequence of SEQ ID NO: 14, and
a CDR3β chain consisting of the amino acid sequence of SEQ ID NO: 15.

16. The method of claim 1, wherein the cancer is lung cancer.

17. The method of claim 1, wherein the cancer is breast cancer.

18. The method of claim 1, wherein the cancer is non-Hodgkin lymphoma.

19. The method of claim 2, wherein the subject is a healthy donor.

20. The method of claim 1, wherein the T cells are CD4+ T cells.

* * * * *